United States Patent
Kobayashi et al.

(10) Patent No.: US 6,509,445 B1
(45) Date of Patent: Jan. 21, 2003

(54) CANCEROUS METASTASIS INHIBITOR

(75) Inventors: Hiroshi Kobayashi, Hamamatsu (JP); Toshihiko Terao, Hamamatsu (JP); Dan Sugino, Otsu (JP); Minoru Okushima, Hirakata (JP)

(73) Assignee: Nissin Food Products Co., Ltd., Osaka (JP)

( * ) Notice: Subject to any disclaimer, the term of this patent is extended or adjusted under 35 U.S.C. 154(b) by 0 days.

(21) Appl. No.: 09/101,272

(22) PCT Filed: Jan. 6, 1997

(86) PCT No.: PCT/JP97/00008
§ 371 (c)(1),
(2), (4) Date: Jul. 8, 1998

(87) PCT Pub. No.: WO97/25422
PCT Pub. Date: Jul. 17, 1997

(30) Foreign Application Priority Data

Jan. 8, 1996 (JP) ............................................. 8-001059

(51) Int. Cl.[7] .................................................. C07K 1/00
(52) U.S. Cl. ....................... 530/350; 530/324; 536/23.1; 536/23.5; 435/320.1; 435/69.1
(58) Field of Search ............................... 536/23.5, 23.1; 435/320.1, 69.1, 71.1; 530/350, 324

(56) References Cited

U.S. PATENT DOCUMENTS

| | | |
|---|---|---|
| 5,112,755 A | 5/1992 | Heyneker et al. |
| 5,409,895 A | 4/1995 | Morishita et al. |
| 5,451,659 A | 9/1995 | Morishita et al. |

FOREIGN PATENT DOCUMENTS

| | | |
|---|---|---|
| GB | 2 246 779 | 2/1992 |
| WO | WO 92/02553 | 2/1992 |

OTHER PUBLICATIONS

Kobayashi et al, *J. of Biol. Chem.*, 270(14):8361–8366 (1995).
"Urokinase–type Plasminogen Activator Precursor", Accession No. P00749, Abstract No. XP002170735, Jul. 21, 1986.
"AMBP Protein Precursor", Accession No. P02760, Abstract No. XP002170736, Jul. 21, 1986.
Supplementary Partial European Search Report.
Spitler, Cancer Biotherapy vol. 10 p. 1, 1995.*
Ezzell, J. NIH Research vol. 7 p. 46, 1995.*
Boon, Adv. Can. Res. vol. 58 p. 177, 1992.*
Kobayashi et al., "Inhibitory Effect of a Conjugate between Human Urokinase and Urinary Trypsin Inhibitor on Tumor Cell Invasion in Vitro" *J. Biological Chemistry* 270(14):8361–8366 (1995).
Shinohara et al., "Urinary trypsin inhibitor" *Biotherapy* 10(10):1359–1365 (1996).
Hiroshi Kobayashi, "A bifunctional hybrid molecule of urokinase amino–fragment and bikunin domain II efficiently inhibits tumor cell invasion and metasis" 33(4);324–332 (1996).
Hiroshi Kobayashi, "Mechanism of tumor cell–induced extracellular matrix degradation—Inhibition of cell–surface proteolytic activity might have a therapeutic effect on tumor cell invasion and metastasis" 14(17):2487–2493 (1996).
Hiroshi Kobayashi, "Mechanism of Tumor Cell–induced Extracellular Matrix Degradation Inhibition of Cell–surface Proteolytic Activity Might have a Therapeutic Effect on Tumor Cell Invasion and Metastasis" 48(8) 623–632 (1996).

* cited by examiner

*Primary Examiner*—Sheela Huff
(74) *Attorney, Agent, or Firm*—Sughrue Mion, PLLC

(57) ABSTRACT

A chimeric protein wherein HI-8 which is the C-terminal domain of human urinary trypsin inhibitor (UTI) having a cancer cell metastasis inhibitory effect, is linked to a peptide containing the G domain of urokinase binding specifically to urokinase receptor expressed in a large amount in cancer cells.

21 Claims, 15 Drawing Sheets

FIG. 5

```
                                                    ┌─────┐
                                                    │ Pr-1│
                                                    └─────┘
                                   ─────────────────────────
                                   5'-CGTGAGCGACTCCAAAGGC
ATGAGAGCCCTGCTGGCGCGCCTGCTTCTCTGCGTCCTGGTCGTGAGCGACTCCAAAGGC         60
 M  R  A  L  L  A  R  L  L  L  C  V  L  V  V  S  D  S  K  G
-20           -15           -10           -5
──▶

AGCAATG-3'
AGCAATGAACTTCATCAAGTTCCATCGAACTGTGACTGTCTAAATGGAGGAACATGTGTG        120
 S  N  E  L  H  Q  V  P  S  N  C  D  C  L  N  G  G  T  C  V
 1           5           10           15           20

TCCAACAAGTACTTCTCCAACATTCACTGGTGCAACTGCCCAAAGAAATTCGGAGGGCAG        180
 S  N  K  Y  F  S  N  I  H  W  C  N  C  P  K  K  F  G  G  Q
          25           30           35           40

CACTGTGAAATAGATAAGTCAAAAACCTGCTATGAGGGGAATGGTCACTTTTACCGAGGA        240
 H  C  E  I  D  K  S  K  T  C  Y  E  G  N  G  H  F  Y  R  G
          45           50           55           60

AAGGCCAGCACTGACACCATGGGCCGGCCCTGCCTGCCCTGGAACTCTGCCACTGTCCTT        300
 K  A  S  T  D  T  M  G  R  P  C  L  P  W  N  S  A  T  V  L
          65           70           75           80

CAGCAAACGTACCATGCCCACAGATCTGATGCTCTTCAGCTGGGCCTGGGGAAACATAAT        360
 Q  Q  T  Y  H  A  H  R  S  D  A  L  Q  L  G  L  G  K  H  N
          85           90           95           100

TACTGCAGGAACCCAGACAACCGGAGGCGACCCTGGTGCTATGTGCAGGTGGGCCTAAAG        420
 Y  C  R  N  P  D  N  R  R  R  P  W  C  Y  V  Q  V  G  L  K
          105          110          115          120
                              ◀──────────────────────────────  ┌─────┐
                              3'-CACGTACTGACGCGTCTACCATGGG-5'  │ Pr-3│
                                                               └─────┘
CCGCTTGTCCAAGAGTGCATGGTGCATGACTGCGCAGATGGAAAAAAGCCCTCCTCTCCT        480
 P  L  V  Q  E  C  M  V  H  D  C  A  D  G  K  K  P  S  S  P
          125          130          135          140

CCAGAAGAATTAAAATTTCAGTGTGGCCAAAAGACTCTGAGGCCCCGCTTTAAGATTATT        540
 P  E  E  L  K  F  Q  C  G  Q  K  T  L  R  P  R  F  K  I  I
          145          150          155          160
               ◀─────────────────────────────────  ┌─────┐
               3'-GTGGTGGTAGCTCTTGGTCGGGACCAAA-5'  │ Pr-2│
                                                   └─────┘
GGGGGAGAATTCACCACCATCGAGAACCAGCCCTGGTTTGCGGCCATCTACAGGAGGCAC        600
 G  G  E  F  T  T  I  E  N  Q  P  W  F  A  A  I  Y  R  R  H
          165          165          170          175
```

FIG. 6

```
          ┌──────┐
          │ Pr-4 │
─────────────────────▶
              I  V
5'-GGGTACCGTTGCTGCTTGCAACCTGCCGATTGTCCG-3'
   ACGGTTGCTGCTTGCAACCTGCCGGTTATCCGTGGTCCGTGCCGTGCTTTCATCCAGCTG   60
   T  V  A  A  C  N  L  P  V  I  R  G  P  C  R  A  F  I  Q  L
   1           5           10          15             20

TGGGCTTTCGACGCTGTTAAAGGTAAATGCGTTCTGTTCCCGTATGGTGGTTGCCAGGGT   120
 W  A  F  D  A  V  K  G  K  C  V  L  F  P  Y  G  G  C  Q  G
          25          30          35             40
                                                              ┌──────┐
                                                              │ Pr-5 │
                                      ◀─────────────────────
                                    3'-GGCACTTATAACGCCACAAGGCCCAACTAGTG-5'
AACGGTAACAAATTCTATTCTGAAAAAGAATGCCGTGAATATTGCGGTGTTCCGGGTGAC   180
 N  G  N  K  F  Y  S  E  K  E  C  R  E  Y  C  G  V  P  G  D
          45          50             55             60

GAAGACGAAGAACTGCTGTGATGATCTAGAGCCCAGCCCGCCTAATGAGCGGGCTTTTTT   240
 E  D  E  E  L  L
          65
```

CANCEROUS METASTASIS INHIBITOR

FIELD OF THE INVENTION

The invention relates to a chimeric protein wherein HI-8 which is the C-terminal domain of human urinary trypsin inhibitor (UTI) having a cancer cell metastasis inhibitory effect is linked to a peptide containing the G domain of urokinase binding specifically to an urokinase receptor expressed in large amounts on cancer cells.

BACKGROUND ART

In current cancer therapy, although advances in early diagnosis and therapy increase a therapeutic rate, an effective remedy against cancer metastasis has not been found. Inhibition of metastasis of cancer is a serious problem. Recent active research clarifies a molecular biological mechanism on metastasis of cancer cells. It has been found that invasion of cancer cells into normal tissue requires actions of a variety of proteases (1) (2). Urokinase-type plasminogen activator (uPA), which is one of serine proteases, is noted earlier as a protease increased with canceration of cells (3). It is reported that the amount of uPA extracted from cancer tissue is generally correlated with malignancy of cancer cells (4). In addition, it is believed that secretion of precursor-type enzymes such as uPA and metalloproteases including collagenase and stromelysin, and a proteolysis cascade including an activation process of the precursor-type enzymes are closely related to an invasion process of cancer cells (5). uPA, which is a glycoprotein having a molecular weight of 55 kDa, has a three-domain structure of, from N-terminal, growth factor-like domain (G domain), kringle domain (K domain) and protease domain (P domain) (see, FIG. 1). G domain is a site to be bound to an urokinase receptor (uPAR) which is a specific receptor on cells (6). It is believed that uPA binds to membrane of cancer cells through the domain and plays an important role during invasion (7) (8) (9) (10) (11). Cancer cells also increase a uPA concentration in the direction to be migrated by collecting uPAR capable of binding to uPA on the tip of migration direction (12). The uPAs bound to cell membrane activate a variety of proteases such as plasminogen on the surface of membrane and degrade extracellular matrices (13) (14) (15).

It is known that plasmin activated by uPA on the surface of membrane of endothelial cell activates latent TGF-$\beta$ (transforming growth factor $\beta$) which exists on the surface of mural cell (16). It is known that TGF-$\beta$ induces production of plasminogen activator inhibitor 1 (PAI-1) which is a selective inhibitory factor of uPA and stimulates expression of mRNA of uPA (17). TGF-$\beta$ controls vascularization according to concentration thereof differently.

In view of foregoing, experiments to inhibit metastasis of cancer cell by inhibiting actions of uPA on the membrane of cancer cell have been tried. Reported are inhibition on invasion by antibody (18) or inhibitor (19) against uPA, or, inhibition on invasion by antibody (21) and peptides (22) (23) which inhibit bonding of uPA to uPAR.

An amino terminal fragment (ATF) of uPA (residues 1–135 of uPA) is a polypeptide comprising G domain to be bound to uPAR and adjacent K domain, and competitively inhibits binding of uPA to uPAR. It is reported by Crowley et al. that a chimeric protein comprising a polypeptide containing 137 amino acids from N-terminal including ATF bound to a Fc region of immunoglobulin G is produced and that the protein inhibits metastasis of human cancer cells in vivo (24). Lu et al. prepare a chimeric protein wherein ATF is bound to human serum albumin (HSA) through a spacer consisting of 4 glycines in yeast. They reported that the chimeric protein bound to uPAR in vitro and inhibited binding of uPA to cancer cell membrane (25). These chimeric proteins were produced to stabilize characteristics of ATF having uPA binding inhibitory action in vivo and to increase metastasis inhibitory effects.

Ballance et al. reports a method for producing chimeric proteins in yeast wherein G domain of uPA is bound to plasminogen activator inhibitor-2 (PAI-2) which is an inhibitor of uPA, or, to $\alpha_1$-antitrypsin ($\alpha_1$-AT) which is a plasmin inhibitor (26). The chimeric protein was produced to increase inhibitory properties by combining G domain properties on binding to uPAR with inhibitory properties of enzymes relating to metastasis. However, experimental data relating to the metastasis inhibitory effect of this chimeric protein have not been reported.

Recently, the inventors found that human urinary tripsin inhibitor (UTI) inhibits invasion of cancer cells (27). UTI demonstrated not only invasion inhibitory effect of cancer cell in vitro (28), but also metastasis inhibitory effect in model system in vivo (29). In addition, the inventors found that $\alpha_2$-antiplasmin ($\alpha_2$-AP) and $\alpha_2$-macroglobulin ($\alpha_2$M), which are plasmin inhibitors belonging to a serpin family, do not inhibit a plasmin activity on plasma membrane, and that UTI inhibited a plasmin activity on plasma membrane leading to inhibition of invasion of cancer cell (29).

UTI comprises two Kunitz-type inhibitor domains and sugar chains (FIG. 2). A plasmin inhibitor site is located in HI-8, which is a second domain (residue 78–143 of UTI) on C-terminal side of UTI (30). The inventors demonstrates that HI-8 has a metastasis inhibitory activity (31). Recent research confirmed that HI-8 inhibited invasion and metastasis under mechanisms other than protease inhibitory action. HI-8 inhibits invasion of cancer cell, on the surface of which is not proved to have a plasmin activity. HI-8 is believed to inhibit invasion and metastasis of cancer cells by protease inhibitory action, and also inhibition of influx of calcium ion and regulation of protein kinase C (PKC) activity.

The inventors produced crosslinked compounds wherein ATF was chemically bound to UTI or HI-8 so as to improve an inhibitory effect by collecting UTI or HI-8 on cancer cells. The crosslinked compounds are found to inhibit metastasis of cancer cells in vitro effectively (32). The compounds synthesized by crosslinking agent, however, have a drawback in an industrial applicability that the compounds have crosslinks in a variety of manners leading to difficulty in large-scale production of substances with single structure.

An inhibitor of cancerous metastasis is a drug administered simultaneously in chemotherapy in case that primary tumor is removed by operation or that surgical treatment is difficult. In the cases, patients to be cured having decreased physical fitness can not tolerate drugs with potent toxicity. Recently, chemotherapeutic agents are revaluated in large scale from the viewpoint of decrease of self-healing ability due to side-effects of anti-cancer agents and of quality of life of patients during therapy.

UTI sample purified from human urine is used in medicinal application as curative medicine for acute circulatory failure and pancreatitis. UTI is a protein whose safety has already been confirmed in intravascular administration (33) (34) (35) (36). Since HI-8 is a part of UTI whose safety is confirmed, it is expected that HI-8 should be developed as cancerous metastasis inhibitor with low toxicity to human.

In addition, G domain of uPA which is a region for binding to a receptor (uPAR) expressed in large amounts on metastatic cancer cells has actions of metastasis inhibition by inhibiting binding of uPA to cancer cells and of specific binding molecule to cancer cells. uPA is a substance which has already been developed as drug and has examined safety thereof. In view of foregoing, it is expected that a chimeric protein prepared by linking a polypeptide comprising G domain of uPA with HI-8 should have effective metastasis inhibitory actions based on combined properties of two proteins. In addition, the chimeric protein which utilizes partial sequences concerning specific functions of two drugs whose safety are established will be used as cancerous metastasis inhibitor with lower toxicity. Furthermore, a large scale production of the chimeric protein as substance having single structure of one polypeptide chain according to gene engineering techniques will greatly contribute to research of cancerous metastasis inhibition and development of inhibitor.

BRIEF DESCRIPTION OF THE DRAWINGS

FIG. 5 shows a relationship of positions of cDNA structure of uPA coding for ATF portion (SEQ ID NO: 72) and primer used for cloning (Pr-1—SEQ ID NO: 3; Pr-2—SEQ ID NO: 4; Pr-3—SEQ ID NO: 7).

FIG. 6 shows a HI-8 gene of pCD17R15 (SEQ ID NO: 75) and the primers [a primer] used for obtaining partial DNA of HI-8 according to PCR (Pr-4—SEQ ID NO: 10; Pr-5—SEQ ID NO: 11).

DISCLOSURE OF THE INVENTION

Figure 1:
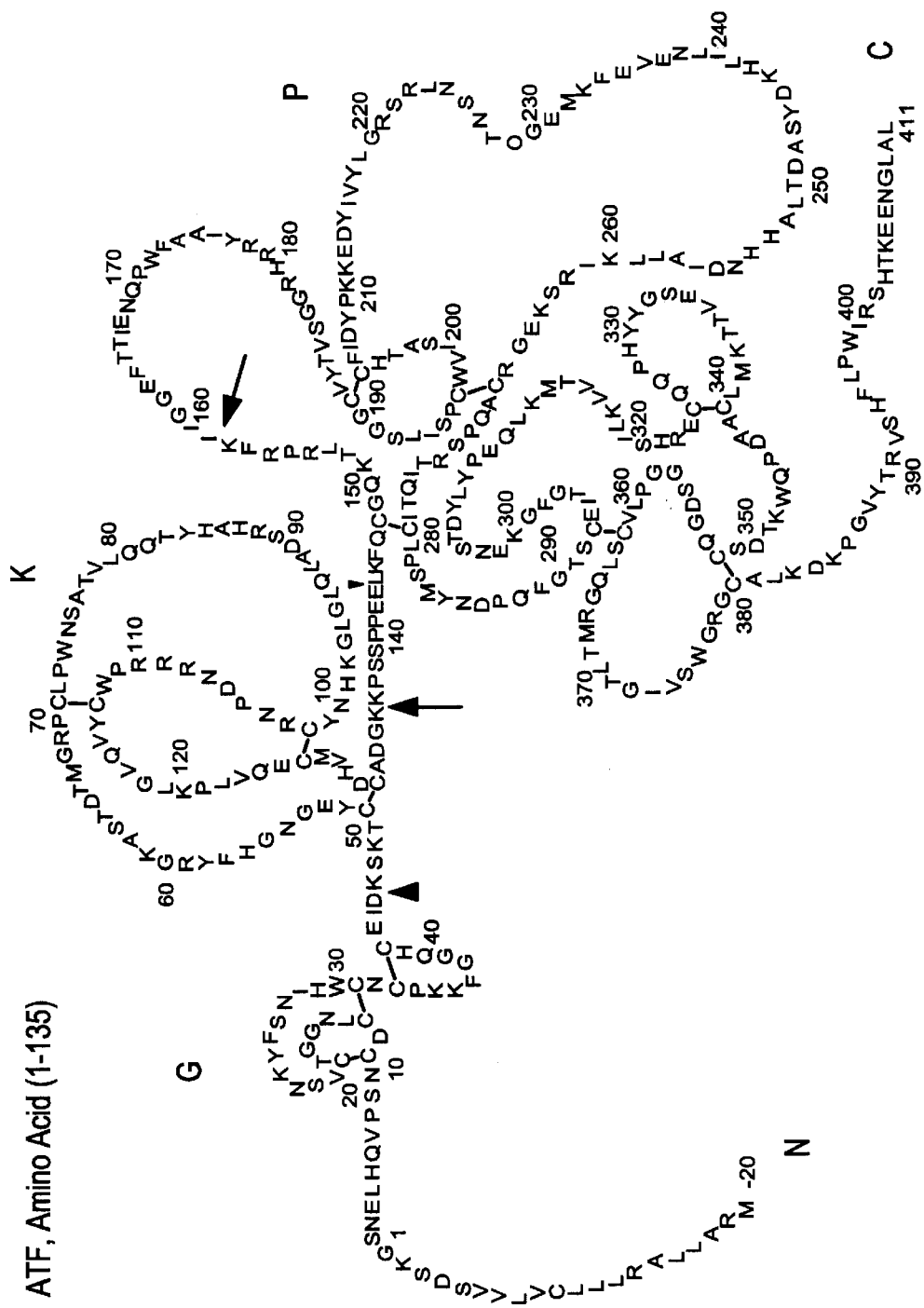
FIG. 1 shows a primary structure of urokinase (uPA) (SEQ ID NO: 1) (from FIG. 7(1), 1712 page of TAKAHASHI Takashi, KO Enki (1991), TANPAKUSITSUKAKUSANKOSO, 36, 1705–1715).
Figure 2:
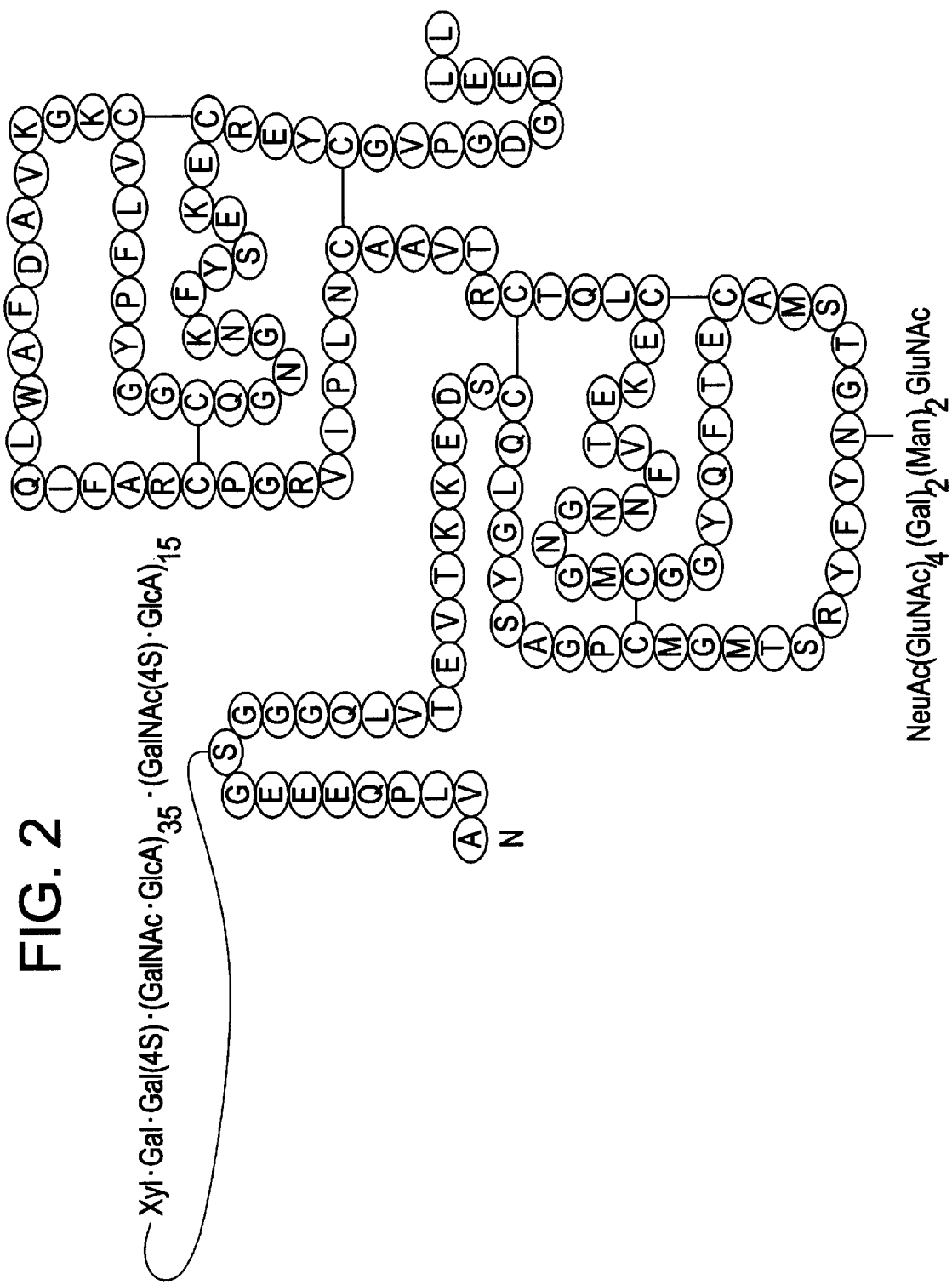
FIG. 2 shows a primary structure of UTI (SEQ ID NO: 2) (partially modified FIG. 1(B) in page 459 of YONEDA Masahiko, KIMATA Koji; SEIKAGAKU, 67:458–465, 1995).
Figure 3:
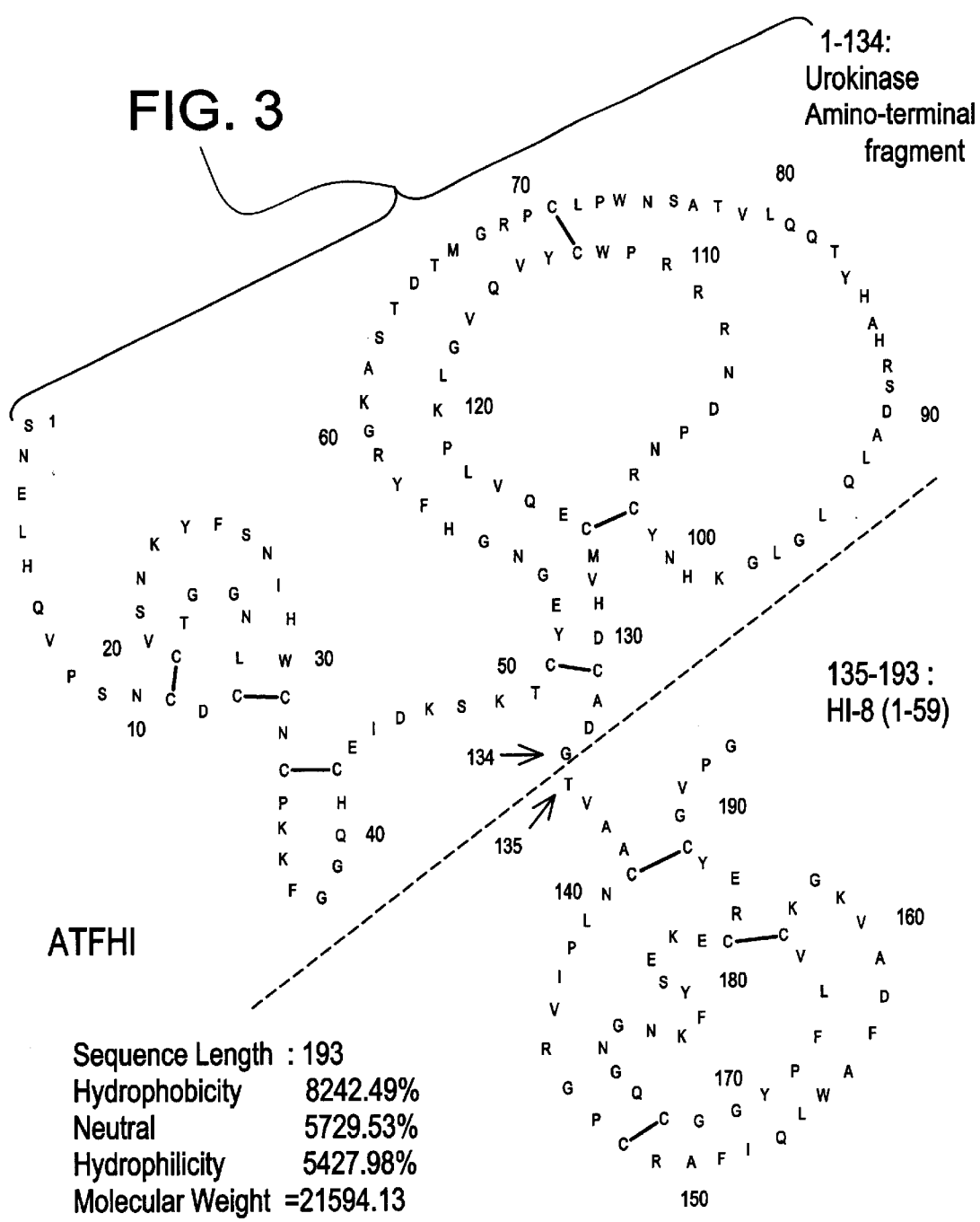
FIG. 3 shows a primary structure of chimeric protein ATFHI (SEQ ID NO: 80).

The inventors worked out a molecular design to maintain a native steric structure of each domain of chimeric protein. The inventors also worked out a design of plasmid to express the chimeric protein in *Escherichia coli* effectively. A chimeric protein expressed in *E. coli* may be accumulated in large amounts in bacterial cell as insoluble inclusion body. A chimeric protein may be collected by refolding treatment followed by purification process as a single substance recovering a steric structure. The chimeric protein maintains both propertied of G domain function binding to uPAR derived from uPA and of plasmin inhibitory function derived from HI-8. Furthermore, it is confirmed from results of cancer cell invasion inhibitory experiment in vitro and of a metastasis inhibition experiment in vivo that the chimeric protein has inhibitory activities of invasion and metastasis higher than ATF and HI-8.

The invention provides a chimeric protein having a cancerous metastasis inhibitory activity, a DNA coding for a chimeric protein, a plasmid comprising the DNA, a transformant maintaining the plasmid, a method for producing the chimeric protein and a method for prophylaxis of cancerous metastasis.

Item 1. A chimeric protein comprising a sequence of the following (formula 1) on N-terminal side and a sequence of the following (formula 2) on C-terminal side:

(Formula 1)
  Cys Asp Cys Leu Asn Gly Gly Thr Cys Val Ser Asn Lys Tyr Phe Ser Asn Ile His Trp Cys Asn Cys Pro Lys Lys Phe Gly Gly Gln His Cys (SEQ ID NO: 18)

(Formula 2)
  Cys Asn Leu Pro Ile Val Arg Gly Pro Cys Arg Ala Phe Ile Gln Leu Trp Ala Phe Asp Ala Val Lys Gly Lys Cys Val Leu Phe Pro Tyr Gly Gly Cys Gln Gly Asn Gly Asn Lys Phe Tyr Ser Glu Lys Glu Cys Arg Glu Tyr Cys (SEQ ID NO: 19)

Item 2. The chimeric protein according to item 1 which further comprises an intervening sequence containing any one of the following 4 sequences between said (formula 1) and said (formula 2):

(formula 3)-Ala Asp Gly Thr Val Ala Ala (SEQ ID NO: 27)

(formula 3)-Ala Asp Gly Lys Lys Pro Ser Ser Pro Pro Glu Glu Leu Lys Phe Gln Gly Thr Val Ala Ala (SEQ ID NO: 38);

Glu Ile Asp Lys Ser Lys Thr Thr Val Ala Ala (SEQ ID NO: 39); and

Glu Ile Asp Lys Ser Lys Thr Val Ala Ala (SEQ ID NO: 40).

Item 3. The chimeric protein according to item 1 comprising a sequence represented by (formula A):

N terminal-(sequence I)-(formula 1)-(sequence II)-(formula 2)-(sequence III)-C terminal (formula A) in (formula A), (formula 1) and (formula 2) are as defined above.

(Sequence I) represents a hydrogen atom or any one of the following amino acid sequences:

Ser Asn Glu Leu His Gln Val Pro Ser Asn (SEQ ID NO:20)

Asn Glu Leu His Gln Val Pro Ser Asn (SEQ ID NO:21)

Glu Leu His Gln Val Pro Ser Asn (SEQ ID NO:22)

Leu His Gln Val Pro Ser Asn (SEQ ID NO:23)

His Gln Val Pro Ser Asn (SEQ ID NO:24)

Gln Val Pro Ser Asn (SEQ ID NO:25)

Val Pro Ser Asn (SEQ ID NO:26)

Pro Ser Asn

Ser Asn (Sequence II) represents any one of sequences selected from a group containing (formula 3) and a group not containing (formula 3)

a group containing (formula 3)

(formula 3)-Ala Asp Gly Thr Val Ala Ala (SEQ ID NO: 27)

(formula 3)-Ala Asp Gly Val Ala Ala (SEQ ID NO: 28)

(formula 3)-Ala Asp Gly Ala Ala (SEQ ID NO: 29)

(formula 3)-Ala Asp Gly Xaa (SEQ ID NO: 30)

(formula 3)-Ala Asp Thr Val Ala Ala (SEQ ID NO: 31)

(formula 3)-Ala Asp Val Ala Ala (SEQ ID NO: 32)

(formula 3)-Ala Asp Ala Ala (SEQ ID NO: 33)

(formula 3)-Ala Asp Xaa (formula 3)-Ala Thr Val Ala Ala (SEQ ID NO: 34)

(formula 3)-Ala Val Ala Ala (SEQ ID NO: 35)

(formula 3)-Xaa Thr Val Ala Ala (SEQ ID NO: 36)

(formula 3)-Xaa Val Ala Ala (SEQ ID NO: 37)

(formula 3)-Xaa Ala Ala (formula 3)-Xaa Xaa (formula 3)-Val Ala Ala (formula 3)-Xaa (Formula 3)-Ala Asp Gly Lys Lys Pro Ser Ser Pro Pro Glu Glu Leu Lys Phe Gln Gly Thr Val Ala Ala (SEQ ID NO: 38)

a group not containing (formula 3)

Glu Ile Asp Lys Ser Lys Thr Thr Val Ala Ala (SEQ ID NO: 39)

Glu Ile Asp Lys Ser Lys Thr Val Ala Ala (SEQ ID NO: 40)

Glu Ile Asp Lys Ser Lys Thr Ala Ala (SEQ ID NO: 41)

Glu Ile Asp Lys Ser Lys Thr Xaa (SEQ ID NO: 42)

Glu Ile Asp Lys Ser Lys Xaa (SEQ ID NO: 43)

Glu Ile Asp Lys Ser Lys Val Ala Ala (SEQ ID NO: 44)

Glu Ile Asp Lys Ser Lys Ala Ala (SEQ ID NO: 45)

Glu Ile Asp Lys Ser Thr Val Ala Ala (SEQ ID NO: 46)

Glu Ile Asp Lys Ser Val Ala Ala (SEQ ID NO: 47)

Glu Ile Asp Lys Ser Ala Ala (SEQ ID NO: 48)

Glu Ile Asp Lys Ser Xaa (SEQ ID NO: 49)

Glu Ile Asp Lys Thr Val Ala Ala (SEQ ID NO: 50)

Glu Ile Asp Lys Val Ala Ala (SEQ ID NO: 51)

Glu Ile Asp Lys Ala Ala (SEQ ID NO: 52)

Glu Ile Asp Lys Xaa (SEQ ID NO: 53)

Glu Ile Asp Thr Val Ala Ala (SEQ ID NO: 54)

Glu Ile Asp Val Ala Ala (SEQ ID NO: 55)

Glu Ile Asp Ala Ala (SEQ ID NO: 56)

Glu Ile Asp Xaa (SEQ ID NO: 57)

Glu Ile Thr Val Ala Ala (SEQ ID NO: 58)

Glu Ile Val Ala Ala (SEQ ID NO: 63)

Glu Ile Ala Ala (SEQ ID NO: 59)

Glu Ile Xaa

Glu Thr Val Ala Ala (SEQ ID NO: 60)

Glu Val Ala Ala (SEQ ID NO: 61)

Glu Ala Ala

Glu Xaa

Xaa

Provided that Xaa represents any amino acid constituting a protein, formula 3 represents the following sequence corresponding to 43–131 of uPA:

(Formula 3)

Glu Ile Asp Lys Ser Lys Thr Cys Tyr Glu Gly Asn Gly His Phe Tyr Arg Gly Lys Ala Ser Thr Asp Thr Met Gly Arg Pro Cys Leu Pro Trp Asn Ser Ala Thr Val Leu Gln Gln Thr Tyr His Ala His Arg Ser Asp Ala Leu Gln Leu Gly Leu Gly Lys His Asn Tyr Cys Arg Asn Pro Asp Asn Arg Arg Arg Pro Trp Cys Tyr Val Gln Val Gly Leu Lys Pro Leu Val Gln Glu Cys Met Val His Asp Cys (SEQ ID NO: 62)

(Sequence III) represents a hydroxyl group (—OH) or any of the following amino acid sequences:

Gly Val Pro Gly Asp Gly Asp Glu Glu Leu Leu (SEQ ID NO: 64)

Gly Val Pro Gly Asp Gly Asp Glu Glu Leu (SEQ ID NO: 65)

Gly Val Pro Gly Asp Gly Asp Glu Glu (SEQ ID NO: 66)

Gly Val Pro Gly Asp Gly Asp Glu (SEQ ID NO: 67)

Gly Val Pro Gly Asp Gly Asp (SEQ ID NO: 68)

Gly Val Pro Gly Asp Gly (SEQ ID NO: 69)

Gly Val Pro Gly Asp (SEQ ID NO: 70)

Gly Val Pro Gly (SEQ ID NO: 71)

Gly Val Pro

Gly Val

Gly

Item 4. The chimeric protein according to item 3 wherein sequence II is (formula 3)-Ala Asp Gly Thr Val Ala Ala (SEQ ID NO: 27) or (formula 3)-Ala Asp Gly Lys Lys Pro Ser Ser Pro Pro Glu Glu Leu Lys Phe Gln Gly Thr Val Ala Ala (SEQ ID NO: 38)

when selected from a group containing (formula 3), and sequence II is

Glu Ile Asp Lys Ser Lys Thr Thr Val Ala Ala (SEQ ID NO: 39) or

Glu Ile Asp Lys Ser Lys Thr Val Ala Ala (SEQ ID NO: 40)

when selected from a group not containing (formula 3).

Item 5. The chimeric protein according to item 3 wherein sequence I is represented by Ser Asn Glu Leu His Gln Val Pro Ser Asn (SEQ ID NO: 20).

Item 6. The chimeric protein according to item 3 wherein sequence I is represented by Ser Asn Glu Leu His Gln Val Pro Ser Asn (SEQ ID NO: 20), and sequence II is (formula 3)-Ala Asp Gly Thr Val Ala Ala (SEQ ID NO: 27) or (formula 3)-Ala Asp Gly Lys Lys Pro Ser Ser Pro Pro Glu Glu Leu Lys Phe Gln Gly Thr Val Ala Ala (SEQ ID NO: 38)

when selected from a group containing (formula 3), and sequence II is

Glu Ile Asp Lys Ser Lys Thr Thr Val Ala Ala (SEQ ID NO: 39) or

Glu Ile Asp Lys Ser Lys Thr Val Ala Ala (SEQ ID NO: 40)

when selected from a group not containing (formula 3).

Item 7. A DNA coding for a chimeric protein comprising a sequence of the following (formula 1) on 5' side and a sequence of the following (formula 2) on 3' side:

(Formula 1)

Cys Asp Cys Leu Asn Gly Gly Thr Cys Val Ser Asn Lys Tyr Phe Ser Asn Ile His Trp Cys Asn Cys Pro Lys Lys Phe Gly Gly Gln His Cys (SEQ ID NO: 18)

(Formula 2)

Cys Asn Leu Pro Ile Val Arg Gly Pro Cys Arg Ala Phe Ile Gln Leu Trp Ala Phe Asp Ala Val Lys Gly Lys Cys Val Leu Phe Pro Tyr Gly Gly Cys Gln Gly Asn Gly Asn Lys Phe Tyr Ser Glu Lys Glu Cys Arg Glu Tyr Cys (SEQ ID NO: 19)

Item 8. The DNA according to item 7 coding for a chimeric protein comprising a sequence represented by (formula A):

N terminal-(sequence I)-(formula 1)-(sequence II)-(formula 2)-(sequence III)-C terminal (formula A) in (formula A), (sequence I), (formula 1), (sequence II), (formula 2) and (sequence III) are as defined above.

Item 9. A plasmid comprising DNA according to item 7 or 8.

Item 10. A tranformant into which the plasmid according to item 9 is introduced.

Item 11. A cancerous metastasis inhibitor comprising the chimeric protein according to any of items 1–6 as active ingredient.

Item 12. A method for producing a chimeric protein comprising introducing into a host cell a plasmid into which the DNA according to item 7 or 8 is integrated to produce a transformant, culturing the transformant and recovering the chimeric protein from a culture.

Item 13. A method for prophylaxis of cancerous metastasis comprising administering a therapeutic amount of the chimeric protein according to any of items 1–6 to a patient of cancer.

Item 14. The transformant according to item 10 wherein said transformant is FERM BP-5293.

Item 15. The transformant according to item 10 wherein said transformant is FERM BP-5745.

Item 16. The transformant according to item 10 wherein said transformant is FERM BP-5746.

Item 17. The protein according to item 1 comprising an amino acid sequence which corresponds to 1–193 of SEQ ID NO: 80.

Item 18. The protein according to item 1 comprising an amino acid sequence which corresponds to 1–200 of SEQ ID NO: 95.

Item 19. The protein according to item 1 comprising an amino acid sequence which corresponds to 1–207 of SEQ ID NO: 97.

Item 20. The DNA according to item 7 comprising a nucleic acid sequence which corresponds to 15–593 of SEQ ID NO: 80.

Item 21. The DNA according to item 7 comprising a nucleic acid sequence which corresponds to 15–614 of SEQ ID NO: 95.

Item 22. The DNA according to item 7 comprising a nucleic acid sequence which corresponds to 15–635 of SEQ ID NO: 97.

Any amino acid represented by Xaa which constitutes a protein indicates any of amino acids constituting a natural protein.

The invention is described below in detail.

The chimeric protein which is a subject of the invention is characterised in that the protein is a molecule having a property (A) of binding to uPAR and a property (B) of plasmin inhibitory activity. In order to express the property (A), maintenance of receptor-binding property of G domain from uPA is necessary. The sequence of G domain (from $Cys^{11}$ to $Cys^{42}$ of uPA) may be modified by replacement, addition or deletion of amino acid as long as the property is maintained.

Therefore, a sequence to express property (A) of the invention comprises the sequence of (formula 1) from $Cys^{11}$ to $Cys^{42}$ of uPA corresponding to G domain of uPA, and a derivative thereof maintaining receptor binding ability of uPA.

Formula 1

Cys Asp Cys Leu Asn Gly Gly Thr Cys Val Ser Asn Lys Tyr Phe Ser Asn Ile His Trp Cys Asn Cys Pro Lys Lys Phe Gly Gly Gln His Cys (SEQ ID NO: 18)

The property (B) is derived from Kunitz-type domain of HI-8. The domain is defined by a sequence (formula 2) from $Cys^5$ to $Cys^{55}$ of HI-8. The Kunitz-type domain exerts a metastasis inhibitory action of cancer cells based on an inhibitory action against trypsin-like enzymes such as plasmin, or a inhibitory action to protein kinase C, or an inhibitory action to influx of calcium ion. The domain may be modified by replacement, addition or deletion of amino acid as long as the metastasis inhibitory action of cancer cell is maintained by retaining at least one of these actions. Therefore, the sequence of (formula 2) comprises derivatives maintaining a metastasis inhibitory action of cancer cell formula 2:

Cys Asn Leu Pro Ile Val Arg Gly Pro Cys Arg Ala Phe Ile Gln Leu Trp Ala Phe Asp Ala Val Lys Gly Lys Cys Val

Leu Phe Pro Tyr Gly Gly Cys Gln Gly Asn Gly Asn Lys Phe Tyr Ser Glu Lys Glu Cys Arg Glu Tyr Cys (SEQ ID NO: 19)

The sequences of (formula 1) and (formula 2) may be directly connected together by a peptide bond. However, with respect to the chimeric protein of the invention, an intervening sequence which have little or no effect on steric structures (biological activities) of sequences of (formula 1) and (formula 2) is preferably inserted between sequences of said (formula 1) and said (formula 2). The intervening sequence is preferably exemplified by a sequence containing any of the following 4 amino acid sequences:

(formula 3)-Ala Asp Gly Thr Val Ala Ala (SEQ ID NO: 27)

(formula 3)-Ala Asp Gly Lys Lys Pro Ser Ser Pro Pro Glu Glu Leu Lys Phe Gln Gly Thr Val Ala Ala (SEQ ID NO: 38);

Glu Ile Asp Lys Ser Lys Thr Thr Val Ala Ala (SEQ ID NO: 39); and

Glu Ile Asp Lys Ser Lys Thr Val Ala Ala (SEQ ID NO: 40).

Any sequence may be further included between said four intervening sequences and said (formula 1) or (formula 2).

The desired chimeric protein of the invention is a polypeptide which has (formula 1) on N-terminal side and (formula 2) on C-terminal side. The polypeptide may be represented by the following (formula A)

(Formula A)

N terminal-(sequence I)-(formula 1)-(sequence II)-(formula 2)-(sequence III)-C terminal.

Sequence I, sequence II and sequence III which are placed at both sides of formula 1 and formula 2 may be any sequence as long as domain structures (steric structures) of formula 1 and formula 2 do not interact with each other and each of formula 1 and formula 2 maintains a functional property thereof. Formula 1 and formula 2 are preferably amino acid sequences existing in proteins from human, which will not give a harmful antigenicity to human body. Sequence I is preferably naturally-occurring N-terminal sequence of human uPA (uPA; $Ser^1$ to $Asn^{10}$). However, amino acid sequences having 9–1 amino acid or amino acids, which are prepared by sequencially deleting one by one amino acid from N terminal thereof, are included in sequence I. In addition, sequence I may represent a hydrogen atom. In this case, N-terminal starts from formula 1. Similarly, sequence III is preferably a native C-terminal sequence of HI-8 (HI-8; $Gly^{56}$ to $Leu^{66}$), but includes amino acid sequences having 10–1 amino acid or amino acids prepared by sequencially deleting one by one amino acid from C-terminal thereof. In addition, sequence III may represent a hydroxyl group (—OH). In this case, C-terminal ends in formula 2.

Sequence II combining formula 1 and formula 2 plays a role as spacer to link two functional domains. Sequence II comprise a sequence having at least one amino acid. In order to exclude an influence between two domain structures, the spacer region is preferably an amino acid sequence with long and flexible structure. In contrast, an extra sequence is not preferable from the viewpoint of antigenicity. Sequence II may be a combined sequence of a native sequence following C-terminal of G domain of formula 1 (sequence II-1: Glu Ile Asp Lys Ser Lys Thr) (SEQ ID NO: 74) and a native N-terminal sequence of HI-8 of formula 2 (sequence II-2: Thr Val Ala Ala) (SEQ ID NO: 76). Sequence II may also be a sequence prepared by combining an amino acid sequence having 7–0 amino acid or acids which are obtained by sequencially deleting one by one amino acid from C-terminal of sequence II-1 with an amino acid sequence having 4–0 amino acid or acids which are obtained by sequencially deleting one by one amino acid from N-terminal of sequence II-2, provided that the number of amino acid of sequence II-1 and the number of amino acid of sequence II-2 are not equal to 0 simultaneously.

Sequence II is preferably a sequence capable of orientating Kunitz-type domain of HI-8 of formula 2 to the outside of plasma membrane, when G domain of formula 1 binds to a receptor. Sequence II may be a sequence including K domain of uPA (formula 3: uPA; $Glu^{43}$ to $Cys^{131}$). Since K domain is reported to bind to negatively-charged molecules such as heparin, said sequence may stabilize a bond of G domain to uPAR and also orientate C-terminal of K domain to the outside of plasma membrane. Example of sequence II containing K domain (formula 3) is a sequence in which formula 3 and a native sequence following C-terminal of formula 3 (sequence II-3: Ala Asp Gly) are linked to N-terminal sequence of HI-8 (sequence II-2: Thr Val Ala Ala) (SEQ ID NO: 76). Sequence II also includes a combined sequence of an amino acid sequence having 3–0 amino acid or acids prepared by sequentially deleting one by one amino acid from C-terminal of sequence II-3 and an amino acid sequence having 4–0 amino acid or acids prepared by sequentially deleting one by one amino acid from N-terminal of sequence II-2 in combination, provided that the number of amino acid of sequence II-3 and the number of amino acid of sequence II-2 are not equal to 0 simultaneously. It is known that uPA is cleaved with plasmin between 135 position and 136 position. C-terminal region including the cleavage position of uPA originally has a function as spacer to connect with protease domain (P domain) of uPA and includes a unique sequence (Lys Lys Pro Ser Ser Pro Pro Glu Glu) (SEQ ID NO: 77). Since the sequence may be useful to express a function as spacer by forming a specific steric structure, sequence II may include sequences wherein a 43–147 sequence of uPA is linked to N-terminal sequence of HI-8 (sequence II-2: Thr Val Ala Ala) (SEQ ID NO: 76) by interposing Gly therebetween.

Preferable (sequence I) is represented by Ser Asn Glu Leu His Gln Val Pro Ser Asn (SEQ ID NO: 20).

Preferable (sequence II) is (formula 3)-Ala Asp Gly Thr Val Ala Ala (SEQ ID NO: 27) or (formula 3)-Ala Asp Gly Lys Lys Pro Ser Ser Pro Pro Glu Glu Leu Lys Phe Gln Gly Thr Val Ala Ala (SEQ ID NO: 38)

when selected from a group containing (formula 3), and is Glu Ile Asp Lys Ser Lys Thr Thr Val Ala Ala (SEQ ID NO: 39) or Glu Ile Asp Lys Ser Lys Thr Val Ala Ala (SEQ ID NO: 40)

when selected from a group not containing (formula 3).

Preferable (sequence III) is represented by

Gly Val Pro Gly Asp Gly Asp Glu Glu Leu Leu (SEQ ID NO: 64) or

Gly Val Pro Gly (SEQ ID NO: 71).

From the foregoing viewpoint, a novel polypeptide consisting of 193 amino acids in total having a 134 amino acid sequence (ATF) derived from uPA on the side of N-terminal and a 59 amino acid sequence derived from HI-8 on the side of C-terminal may be provided as example of chimeric protein which may be designed (FIG. 3). A predictable molecular weight of the chimeric protein is 21,564. The chimeric protein is hereinafter referred to as ATFHI (as shown in SEQ ID NO: 80).

Other preferable chimeric proteins included in the present invention are shown in SEQ ID NOs: 96 and 98.

Analytical calculation of biochemical properties of protein, or analysis on nucleic acid sequence may be done by using analysis software such as GENETYX (SOFTWARE DEVELOPMENT).

A method for producing a protein of the invention is described below taking ATFHI as example. As host cells to prepare the chimeric protein ATFHI in large amounts, yeast, mammalian cells and like eucaryote cells and also *E. coli* and like procaryote cells may be used. In general, when a desired protein is expressed in *E. coli*, there are a method for secretion of the protein to periplasm fraction and a method for direct expression of the protein in cytosol as inclusion body. When secreted into periplasm, a desired substance may be obtained as a soluble protein having a steric structure. However, there are disadvantages that the amount of secreted protein in periplasm is small and that the protein is likely to be cleaved by proteases. In contrast, when directly expressed in cytosol, a steric structure should be reconstructed by solubilizing an inclusion body of accumulated insoluble protein with protein solubilizer, followed by refolding the protein. Since most of the fraction of inclusion body is a desired protein, the direct expression method to cytosol is often used because of easiness of purification and large-scale production. In this case, since a DNA sequence coding for an objective product is directly linked to an initiation methionine codon, it is necessary to remove N-terminal methionine from an expressed objective substance. It is known that N-terminal methionine is removed by methionine aminopeptidase (MAP) with respect to most of newly generated proteins in cytosol. The cleavage by the peptidase is greatly affected by types of amino acids next to initiation methionine (37). N-terminal amino acid of uPA is serine. When amino acids having a short side chain such as serine follows an initiation methionine, methionine is likely to be cleaved by MAP. It is reported that N-terminal methionine is removed in case of direct expression of uPA using *E. coli* (38). Thus, ATFHI may be prepared by a direct expression method using *E. coli*. Methionine may be removed when an amino acid other than serine is selected as amino acid next to methionine.

A method for constructing a plasmid expressing a chimeric protein in *E. coli* is described below. DNA as material may easily be synthesized using a chemical synthesis method because of improvement of performance and spread of a current DNA synthesizer, when DNA sequence is known. Preparation of cDNA by screening a cDNA library may be easily carried out using a commercially available kit. Necessary parts of DNAs of uPA and UTI may be cloned using a DNA cloning kit for PCR and a variety types of gene libraries which are commercially available.

cDNA of uPA has been already cloned. The gene structure thereof is clarified by Heyneker et al (39). Method for producing uPA and analogs thereof using microorganisms and animal cells are also reported (40) (41) (42) (43). Necessary parts of DNA may be chemically synthesized, and cDNA of uPA may be easily obtained by separation from a suitable gene library by referring to the cDNA sequence described in the reports. A partial cDNA of uPA coding for ATF portion may be cloned according to a PCR method as shown below. First, suitable primer regions for PCR amplification are selected from DNA sequence containing a sequence from gene sequence of uPA to around ATF so as to make Tm of primers equal with GC content of about 50%. Subsequently, partial DNA fragment of uPA is amplified according to a PCR method using a cDNA prepared using mRNA derived from human tissue material expressing uPA (for example, kidney) as template. The DNA fragment is cloned in *E. coli* by inserting the fragment into a suitable vector using a commercially available cloning kit. The plasmid thus obtained (for example pPPA) comprising DNA coding for ATF may be used as a starting material to construct an expression plasmid.

Since a gene structure of HI-8 (UTI) was reported (44), DNA as starting material may be obtained according to a similar cloning method. A plasmid (pCD17R15), disclosed in Japanese Unexamined Patent Publication H6-247998, comprising HI-8 DNA sequence suitable for expression in *E. coli* may be used. The plasmid comprises a DNA sequence whose codons are used frequently in *E. coli* to produce HI-8 analogs in *E. coli*. In order to prepare DNA of ATFHI using the plasmids as starting material, it is important to obtain necessary DNA fragments by a PCR method and also to introduce a suitable restriction site previously for the purpose of improving efficiency. It is necessary to obtain a optimum combination of a restriction site and synthetic DNA so as to improve efficiency of expression in *E. coli* as stated below.

Figure 4:
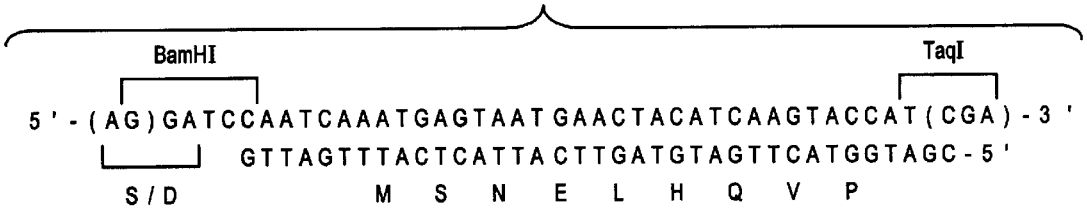
FIG. 4 shows a structure of synthetic DNA adapter BamHI-TaqI DNA (coding sequence—SEQ ID NO: 8; non-coding sequence—SEQ ID NO: 9; amino acid sequence SEQ ID NO: 99).

In order to produce a desired protein in *E. coli* in large amounts, it is important to use a plasmid with high amplification number (copy number) and to use a promoter sequence and a terminator sequence which are optimum for expression. Productivity is affected by a DNA sequence and length of a region from Shine-Dalgarno sequence in ribosome binding site to a translation initiation codon ATG (SD-ATG), or a higher-order structure of mRNA around translation initiation point (38). The higher-order structure of mRNA near translation initiation point is affected by the following DNA sequence coding for a N-terminal amino acid sequence. Therefore, it is important to consider a potential energy value of a higher-order structure of mRNA around N-terminal sequence including SD-ATG region so as to design an expression plasmid. An optimum mRNA structure may be obtained by replacing a natural cDNA sequence with a chemically synthesized DNA coding for SD-ATG region and several amino acids in N-terminal region of an expression plasmid. cDNA of uPA has a cleavage site of restriction enzyme TaqI on codons from N-terminal amino acid to Ser at 9 position. A chemically synthesized DNA located on 5' side from the TaqI site may be replaced with natural DNA sequence. As promoter, a potent taq promoter is often used, and a commercially-available taq promoter sequence (tac promoter GenBlock, Pharmacia) may be used. The promoter has a BamHI cohesive end sequence, a 3' side of which contains a Shine-Dalgarno sequence. Replacement using a chemically synthesized DNA sequence between BamHI and TaqI which is suitable for expression in *E. coli* may be carried out by using the cohesive end and said TaqI site (FIG. 4).

DNA coding for chimeric protein ATFHI may be constructed by ligating two DNA fragments of ATF and HI-8, through recognition sites of restriction enzymes. An amino acid sequence at linkage site corresponds to Gly at 134 position of ATF and Thr at 1 position of HI-8. KpnI recognition site may be created by codons corresponding to Gly-Thr. Since another KpnI recognition site does not exist in chimeric gene of ATFHI, the site may be used as a specific site for cleavage and recognition of linkage site of ATF and HI-8.

A specific procedure of producing a plasmid is shown below. Necessary DNA fragments are prepared according to a PCR method with modified primers by using, as template, said plasmids pPPA and pCD17R15 to be starting materials of ATF and HI-8 DNAs. An expression plasmid may be constructed after preparing the following two intermediate plasmids.

Figure 7:
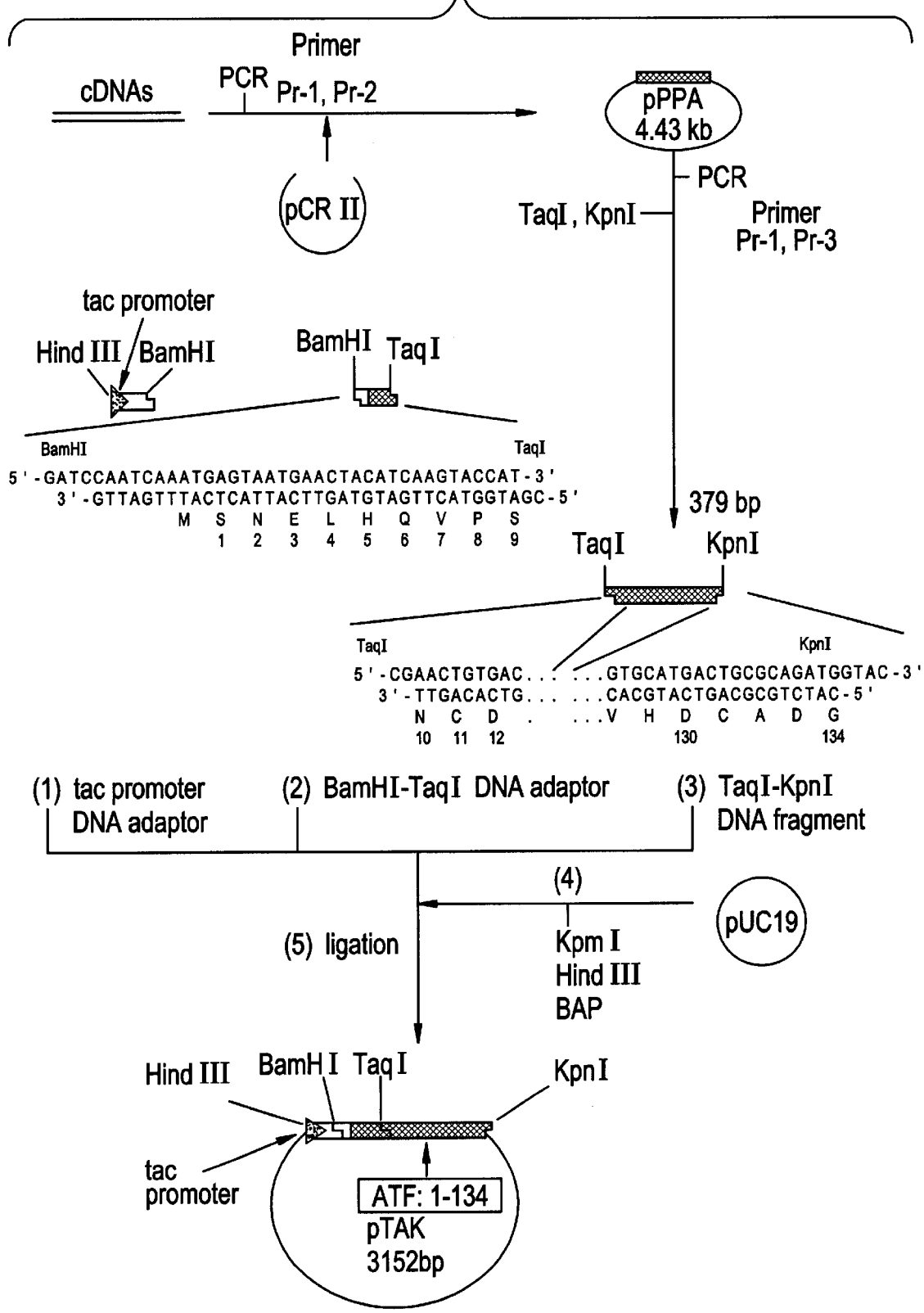
FIG. 7 shows a procedure to construct plasmid pTAK (coding sequence of BamHI-TaqI adapter—SEQ ID NO: 8; non-coding sequence of BamHI-TaqI adapter—SEQ ID NO: 9; amino acids encoded by BamHI-TaqI adapter—SEQ ID NO: 99; 5' coding sequence of TaqI-KpnI adapter—SEQ ID NO: 81; 5' non-coding sequence of TaqI-KpnI adapter—SEQ ID NO: 82; amino acids encoded by 5' end TaqI-KpnI adapter—SEQ ID NO: 100; 3' coding sequence of TaqI-KpnI adapter—SEQ ID NO: 83; 3' non-coding sequence of TaqI-KpnI adapter—SEQ ID NO: 84; amino acids encoded by 3' end TaqI-KpnI adapter—SEQ ID NO: 101).

The intermediate plasmid pTAK comprising a DNA fragment coding for ATF portion (Ser$^1$–Gly$^{134}$) may be produced as shown below. When plasmid pPPA as primer is amplified by PCR, a suitable DNA sequence upstream (5' side) of a TaqI recognition site is selected as primer on 5' side. A primer on 3' side may be used to generate a KpnI recognition site on 3' side of ATF (FIG. 5). The resulting PCR-amplified DNA is cleaved by TaqI and KpnI to obtain a DNA fragment with cohesive ends of the restriction enzymes. This DNA fragment and a HindIII-BamHI adapter having a tac promoter sequence, and BamHI-TaqI adapter chemically synthesized to improve efficiency of translation in *E. coli* are inserted in HindIII-KpnI site of pUC 19 to produce the intermediate plasmid pTAK (FIG. 7).

Figure 8:
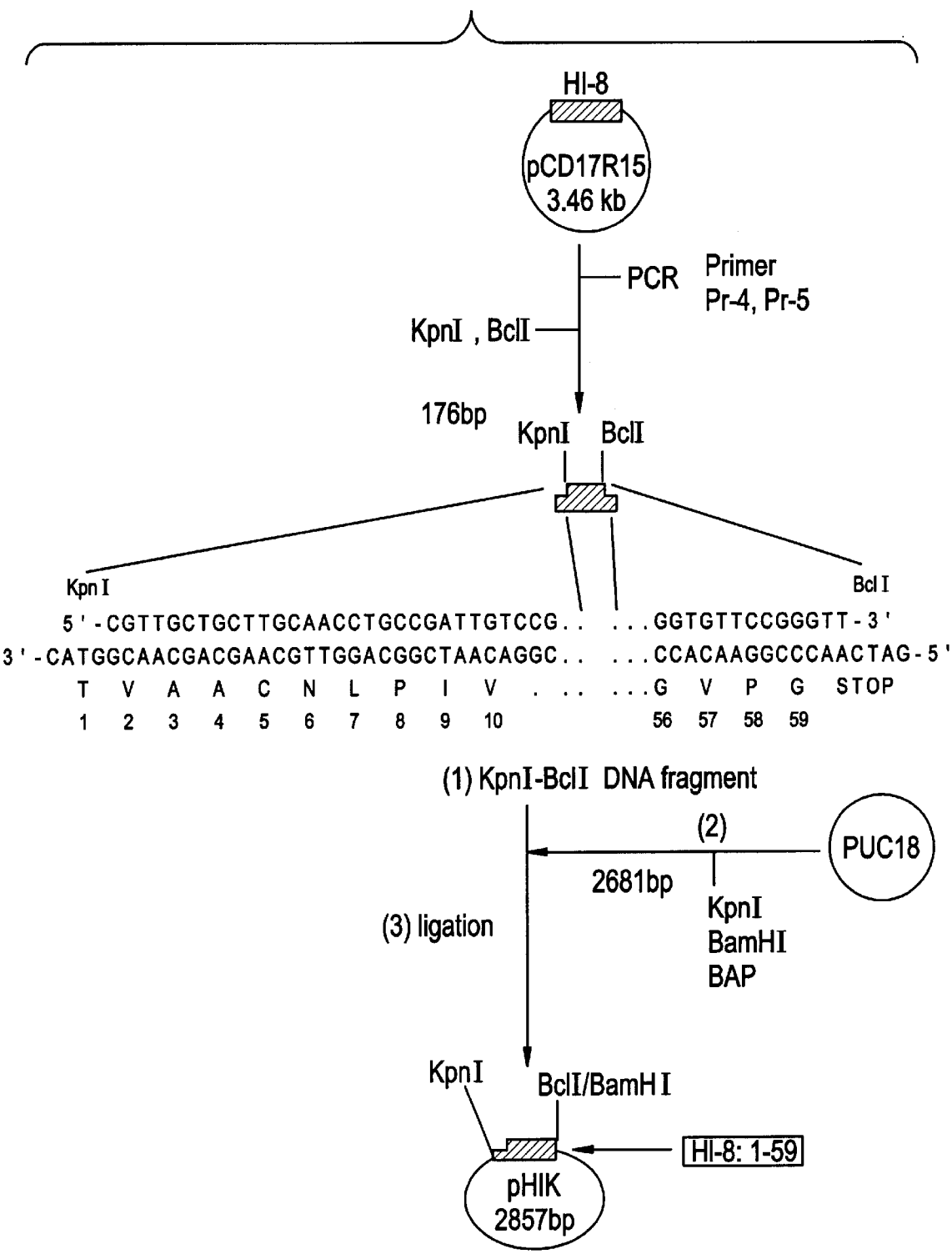
FIG. 8 shows a procedure to construct plasmid pHIK (5' coding sequence of KpnI-BclI adapter—SEQ ID NO: 85; 5' non-coding sequence of KpnI-BclI adapter—SEQ ID NO: 86; amino acids encoded by 5' end KpnI-BclI adapter—SEQ ID NO: 102; 3' coding sequence of KpnI-BclI adapter—SEQ ID NO: 87; 3' non-coding sequence of KpnI-BclI adapter—SEQ ID NO: 88; amino acids encoded by 3' end KpnI-BclI adapter—SEQ ID NO: 103).

An intermediate plasmid pHIK having a DNA fragment coding for HI-8 (Thr$^1$ to Gly$^{59}$) may be produced as follows. The amino acid sequence of HI-8 encoded by pCD17R15 is different from an amino acid sequence predicted from cDNA at 9th position and 10th position. However, the same DNA fragment as cDNA may be obtained by PCR amplification using a primer to change a mutated amino acid Val at 9th position of HI-8 encoded by pCD17R15 to Ile and Ile at 10th position to Val (FIG. 6). A KpnI site is introduced into 5' side thereof to be linked to 3' side of ATF. Furthermore, a termination codon TGA is introduced next to Gly at 59th position of HI-8 using a primer designed to create a recognition site of restriction enzyme BclI on 3' side. The PCR-amplified DNA may be cleaved with KpnI and BclI to obtain a DNA fragment with each cohesive end, which may be inserted in a KpnI-BamHI site of pUC 18 to generate an intermediate plasmid pHIK (FIG. 8).

Figure 9:
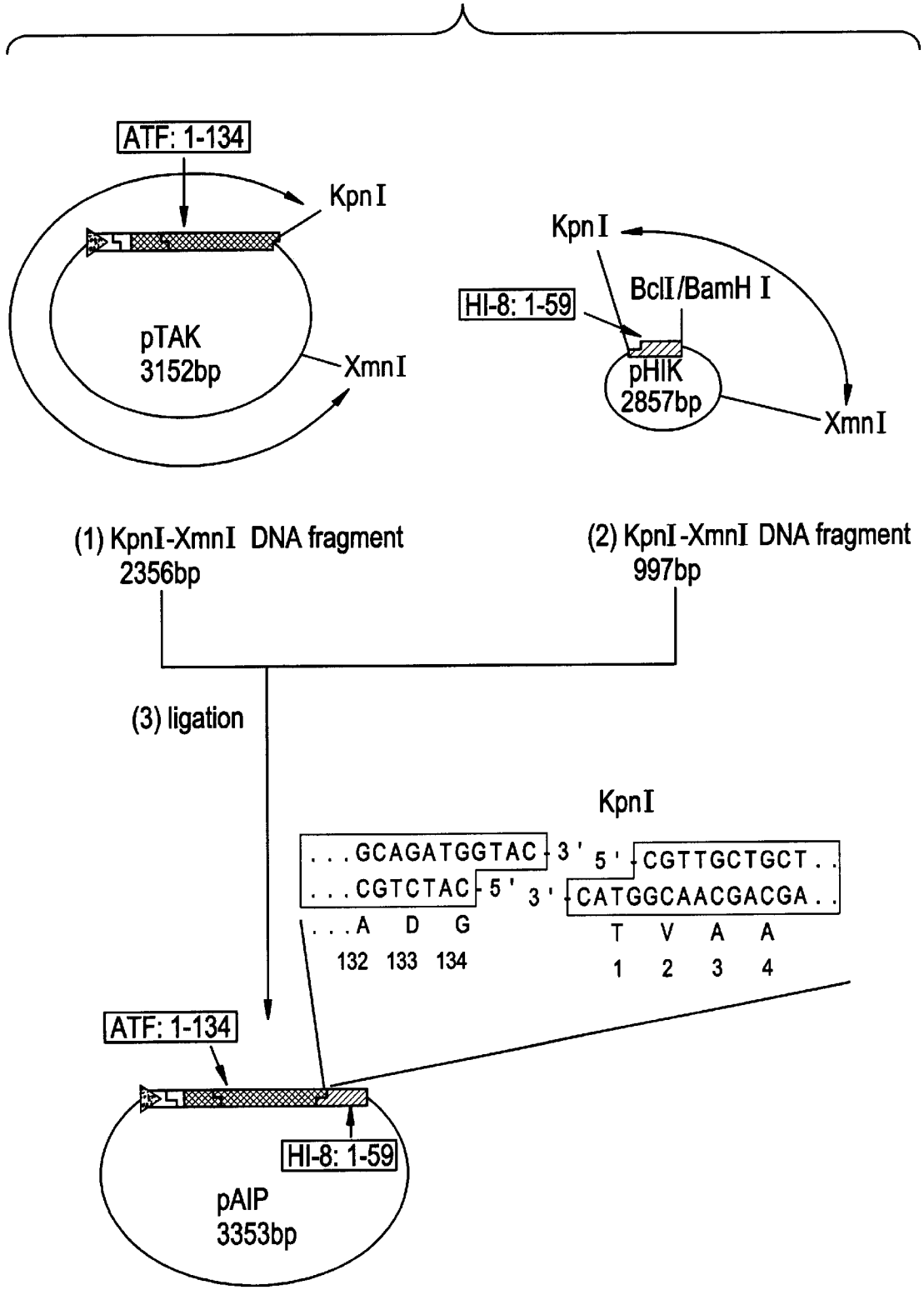
FIG. 9 shows a procedure to construct plasmid pAIP (coding sequence of 3' end of ATF uPA DNA fragment—SEQ ID NO: 89; non-coding sequence of 3' end of ATF uPA DNA fragment—SEQ ID NO: 90; amino acids encoded by 3' end of ATF uPA DNA fragment—SEQ ID NO: 104; coding sequence of 5' end of HI-8 UTI DNA fragment—SEQ ID NO: 91; non-coding sequence of 5' end of HI-8 UTI DNA fragment—SEQ ID NO: 92; amino acids encoded by 5' end of HI-8 UTI DNA fragment—SEQ ID NO: 105).

Two intermediate plasmids pTAK and pHIK are cleaved by KpnI and XmnI to purify necessary DNA fragments. The fragments are combined together by ligation to produce an expression plasmid pAIP for production of chimeric protein ATFHI in *E. coli* (FIG. 9).

A chimeric protein may be produced by using a host cell, for example, *E. Coli* (e.g. JM109) into which the expression plasmid pAIP is introduced to produce a transformant. Production of ATFHI is induced by adding isopropyl β-D-thiogalactopyranoside (IPTG) to a culture of the transformant at a suitable time. *E. coli* produces ATFHI as inclusion body. A steric structure of ATFHI may be reconstructed by well known purification procedure of inclusion body and refolding procedure. A reconstructed ATFHI may be purified by a combination of conventional methods for purifying proteins, such as ion-exchange chromatography and gel filtration.

The chimeric protein of the invention may be used as a cancerous metastasis inhibitor. The chimeric protein may be administered as injections for intravenous, intramuscular, subcutaneous, intracutaneous and intraperitoneal administration, inhalations for intrapulmonary administration, oral medicines, suppositories, plasters, liquids and so on. Carriers added to the preparations are any of conventionally used carriers. The dosage per day is variable with administration route, age, sex, symptoms, types of cancer of the patient, but usually ranges from about 0.1–200 mg for human adult.

Cancers whose metastasis is inhibited include leukemia, cancer of liver, renal cartinoma, pancreatic cancer, esophageal carcinoma, colon cancer, rectum cancer, malignant lymphoma, ovarian cancer, cervical cancer, brain tumor, osteosalcoma, skin carcinoma, breast cancer and prostatic cancer.

A novel cancerous metastasis inhibitor with lower toxicity and potent inhibitory effect of invasion and metastasis of cancer to human may be produced leading to providing a very useful drug for cancer therapy.

BEST MODE FOR CARRYING OUT THE INVENTION

Reference Example 1

Preparation of Plasmid pPPA

DNA encoding ATF from commercially available cDNAs, which was amplified by a PCR method, was cloned in *E. coli*. A PCR reaction was conducted using synthetic primers Pr-1 (5'-CGTGAGCGACTCCAAAGGCAGCAATG-3', SEQ ID NO: 3) and Pr-2 (5'-AAACCAGGGCTGGTTCTCGATGGTGGTG-3', SEQ ID NO: 4) and cDNAs (QUICK-Clone cDNA, CLONTECH) from human kidney as template. In the PCR reaction, a commercially available PCR reaction kit (Gene Amp, Perkin Elmer Cetus) was used in a 100 µl of reaction system including 1 ng of cDNA, 50 pmol of each primer. 30 cycles of PCR was conducted wherein one cycle corresponded to 94° C. for 1 minute, 55° C. for 2 minutes and 72° C. for 3 minutes. The amplified DNA having 538 bp was separated and purified, and then inserted into a vector pCR II (Invitrogen) using PCR product cloning kit (TA Cloning Kit, Invitrogen). According to manual of the kit, a ligation reaction and transformation were conducted. A plasmid retained in the resulting transformed *E. coli* was purified by alkaline method (YODOSHA, IDENSIKOGAKU HANDBOOK, pp.19–26, 1991). It was confirmed that a desired plasmid pPPA was correctly constructed by examining a restriction enzyme cleavage pattern and base sequence of DNA with a DNA sequencer (ALF DNA Sequencer, Pharmacia).

Reference Example 2

Preparation of Plasmid pCD17R15

Figure 10:
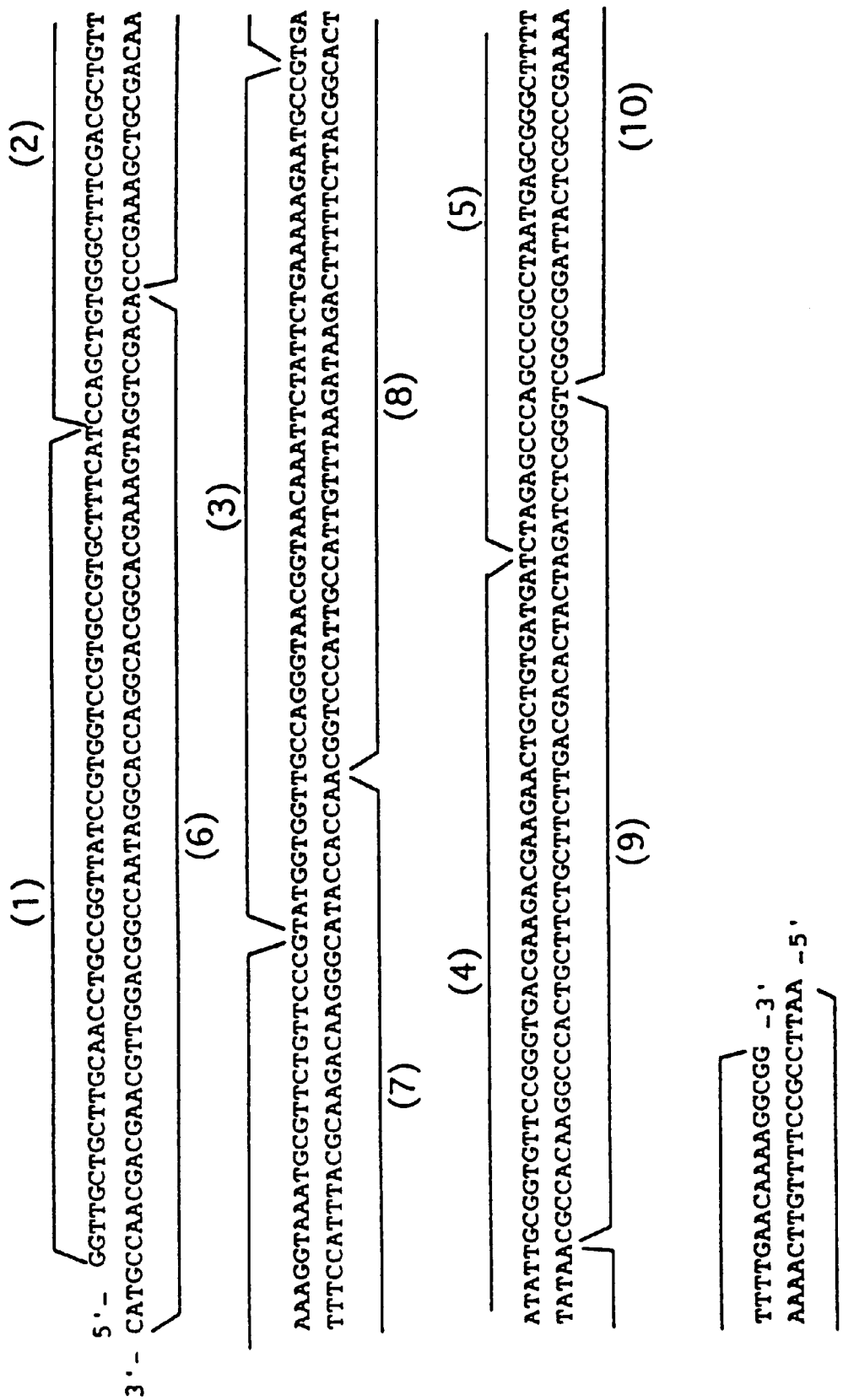
FIG. 10 shows a sequence of synthetic HI-8 DNA to construct plasmid pCD17R15 (SEQ ID NO: 16 and SEQ ID NO: 17).

Each oligonucleotides of base sequences (1) to (10) (SEQ ID NOs: 16 and 17) as shown in FIG. 10 was chemically synthesized by phosphoamidide method with automatic DNA synthesizer (Model 381A, Applied Biosystems). Protective groups of synthesized DNAs were removed by warming at 55° C. overnight in conc. aqueous ammonia. The resulting compound was purified using a reverse phase column for purification of oligonucleotide (OPC Cartridge Column, Applied Biosystems). When necessary, 5' end of synthetic DNAs were phosphorylated by a reaction at 37° C. for 1 hour in solution containing 50 mM Tris-HCl (pH 7.6) with 16 units of polynucleotidekinase (TOYOBO), 1 mM MgCl$_2$, 0.5 mM dithiothreitol (DTT) and 1 mM ATP. The reaction mixture was then separated by polyacrylamide gel electrophoresis (PAGE) with gel concentration of 20% containing 7 M urea. After staining gel with ethydium bromide, a band portion containing desired oligonucleotides was cut out on long wavelength (365 nm) ultraviolet generator. Sliced gel was crashed with 1 mM of DNA eluting solution (20 mM Tris-HCl, pH 8.0, 1.5 mM EDTA), and which was shaken at 37° C. overnight and centrifuged. A supernatant was subjected to a desalting column to obtain a synthetic oligonucleotide solution. Complementary upper and lower chains in FIG. 10, for example, synthetic oligonucleotides of base sequence (1) and base sequence (6) were mixed in equimolar quantity in a solution containing 50 mM Tris-HCl (pH 7.6) and 10 mM MgCl$_2$ and the solution was treated at 90° C. for 5 minutes. Annealing of DNA was conducted by slowly cooling the solution to room temperature by allowing the solution to stand. Annealed synthetic DNA fragment was separated using urea-free PAGE with gel concentration of 10%, and was purified from cut gel.

A plasmid pTV118N (TAKARA) was cleaved by restriction enzymes EcoRI and KpnI. After agarose gel electrophoresis for separation, a desired DNA band was cut. The gel section was frozen at −80° C. for 1 hour and then quickly heated to 37° C. for filtration with centrifugation-type filter (Millipore) having a pore size of 0.1 μm.

Figure 11:
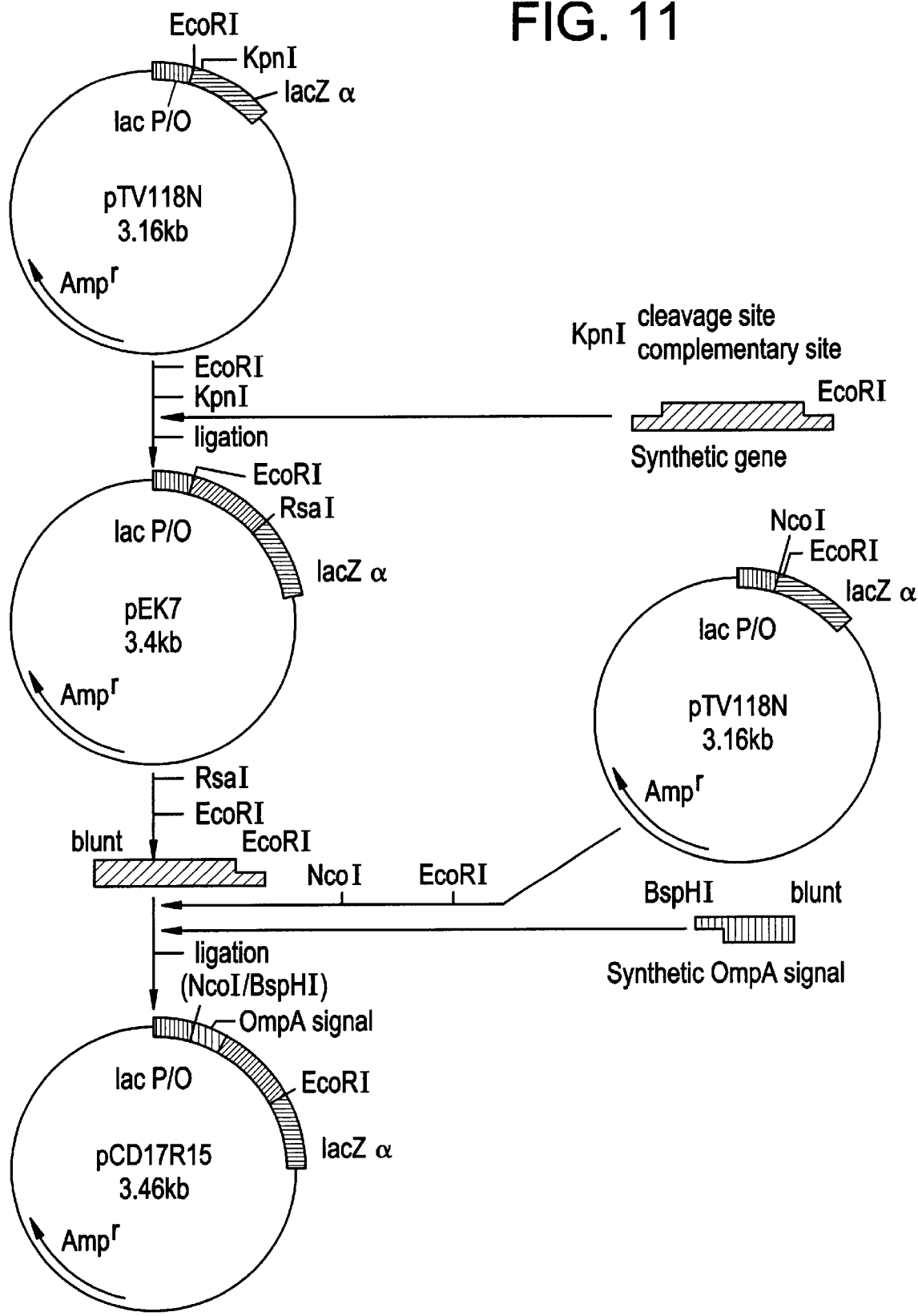
FIG. 11 shows a procedure to construct plasmid pCD17R15.

The filtrate solution was extracted with phenol, and then precipitated with ethanol to purify a DNA fragment. The DNA fragment and annealed sets of synthetic DNA fragments were mixed in a solution containing 50 mM Tris-HCl (pH 7.6), 10 mM MgCl$_2$, 10 mM DTT and 1 mM ATP and then ligated with 10 units of T4 DNA ligase (TAKARA) at 4° C. overnight. Transformation was conducted using a commercially available *E. coli* JM109 competent cell (TAKAPA). A desired plasmid was selected by separation and purification of plasmids from transformed *E. coli*. Structure of the desired plasmid was confirmed by analysis of a restriction enzyme cleavage pattern and DNA base sequence. The plasmid thus obtained was named pEK7 (FIG. 11). The following two synthetic DNAs are complement with each other and form double strand DNA retaining BspHI cohesive end at 5' end and blunt end at 3' end:

5'-CATGAAAAAAACCGCTATCGCTATCGCTGTTGC TCTGGCTGGTTTTGCTACCGTTGCTCAGGCC-3', SEQ ID NO: 5;

5'-GGCCTGAGCAACGGTAGCAAAACCAGCCAGAGC AACAGCGATAGCGATAGCGGTTTTTTT-3', SEQ ID NO: 6

The DNA fragments encode amino acids of signal peptide of *E. coli* outermembrane protein A (OmpA). The DNA fragment prepared according to the above-mentioned method, and a DNA fragment having 0.25 kb generated by cleavage of plasmid pEK7 with restriction enzymes RsaI and EcoRI, were ligated into NcoI-EcoRI site of pTV118N. According to previously described method, transformation of *E. coli* and separation and purification of a plasmid from the transformed *E. coli* were conducted. It was confirmed by analysis of restriction enzyme cleavage pattern and DNA base sequence of plasmid that a desired plasmid pCD17R15 was obtained.

EXAMPLE 1

Construction of Expression Plasmid

1. Construction of pTAK Plasmid (FIG. 7)

Treatments were conducted to obtain a necessary part of DNA by PCR using plasmid pPPA as template. Synthetic primer Pr-3 (5'-GGGTACCATCTGCGCAGTCATGCAC-3', SEQ ID NO: 7) was designed to create a KpnI site on 3' side of DNA coding for ATF (FIG. 5). In a synthetic system (100 μl) containing plasmid pPPA (10 ng), and 100 pmol portions of primers Pr-1 and Pr-3, 25 cycles of PCR reaction were conducted wherein one cycle corresponded to 94° C. for 1 minute, 50° C. for 1 minute and 72° C. for 3 minutes. Amplified PCR product was purified by ethanol precipitation, cleaved by restriction enzymes TaqI and KpnI, and separated by 1.5% agarose gel electrophoresis. A DNA fragment having 379 bp was cut off from gel. DNA was recovered using centrifugation tube with filter for DNA recovery (SpinBind DNA Extraction Units, FMC BioProducts). The DNA fragment having 379 bp encodes 10–134 amino acid sequence of uPA (FIG. 7-(3)).

For the purpose of efficient expression of desired product in *E. coli*, DNA coding for N-terminal 1–9 amino acid sequence of ATF next to initiation Met was chemically synthesized. The following two synthetic DNAs are complement with each other and form BamHI cohesive end on 5' side and TaqI cohesive end on 3' side:

5'-GATCCAATCAAATGAGTAATGAACTACATCAAG TACCAT-3', SEQ ID NO: 8;

5'-CGATGGTACTTGATGTAGTTCATTACTCATTTGA TTG-3', SEQ ID NO: 9

5' ends of the synthetic DNAs were phosphorylated using T4 polynucleotidekinase (TAKAPA) and ATP, and then annealed by boiling at 100° C. for 2 minutes followed by spontaneous cooling to form an adaptor DNA. The BamHI-TaqI adapter encoded 5' non-translation sequence consisting of 11 bases, initiation codon and following 9 amino acid sequence from N-terminal of ATF (FIG. 7-(2)). 100 ng of DNA fragment prepared by cleavage of pUC19 with KpnI and HindIII, followed by dephosphorylation using bacterial alkaline phosphatase (BAP, TAKARA), 20 pmol of tac promoter DNA adaptor (tac promoter GenBlock, Pharmacia), 20 pmol of BamHI-TaqI adapter and 200 ng of Taq-KpnI DNA fragment having 379 bp were ligated using a commercially available DNA ligation kit (DNA Ligation Kit Ver.2, TAKARA). The product was introduced into *E. coli* JM109 competent cells (TAKALRA) to obtain a transformant. A plasmid was prepared from the resulting transformant. It was confirmed that the desired plasmid pTAK was obtained by analysis of restriction enzyme cleavage pattern and DNA base sequence.

2. Construction of pHIK Plasmid (see FIG. 8)

Plasmid pCD17R15 has a DNA sequence of HI-8 variant whose codons are converted into frequently used codons in *E. coli* to improve expression efficiency in *E. coli* (Japanese Unexamined Patent Publication H6-247998, FIG. 11). The amino acid sequence of HI-8 encoded by the plasmid is different from amino acids predicted from reported cDNA sequence in 9th position, 10th position and 61st position. In order to ligate DNAs of ATF and HI-8 with KpnI, a primer Pr-4 (5'-GGGTACCGTTGCTGCTTGCAACCT GCCGATTGTCCG-3', SEQ ID NO: 10) to change Val to Ile at 9th position and Ile to Val at 10th position was designed. A primer Pr-5 (5'-GTGATCAACCCGGAA CACCGCAATATTCACGG-3', SEQ ID NO: 11) for modification of DNA was designed to introduce a termination codon TGA into a position adjacent to Gly at 59th position of HI-8 and to have BclI recognition site simultaneously. In a reaction system (100 μl) containing a plasmid pCD17R15 (10 ng) as template DNA, and each 100 pmol portions of primers Pr-4 and Pr-5, 25 cycles of PCR reaction were conducted wherein one cycle corresponded to 94° C. for 1 minute, 50° C. for 1 minute and 72° C. for 3 minutes. Amplified product was collected by ethanol precipitation, and then cleaved by KpnI and BclI to obtain DNA fragment having 176 bp (FIG. 8-(1)). A vector DNA was prepared by cleaving pUC18 by KpnI and BamHI, followed by dephosphorylation by BAP treatment (FIG. 8-(2)). 100 ng of the vector DNA and 200 ng of DNA fragment having 176 bp were ligated using a ligation kit (FIG. 8-(3)). The product was introduced into *E. coli* JM 109 competent cell to separate a transformant. A plasmid prepared from the transformant was subjected to analysis of DNA base sequence to confirm that the desired plasmid pHIK was constructed as desired.

3. Construction of Expression Plasmid pAIP (FIG. 9)

The plasmids pTAK and pHIK were cleaved by KpnI and XmnI respectively, and then separated by 1.0% agarose gel electrophoresis to purify a DNA fragment having 2356 bp (FIG. 9-(1)) derived from pTAK and a DNA fragment having 997 bp (FIG. 9-(2)) derived from pHIK. Subsequently, 100 ng portions of each DNA fragment were mixed and ligated using a ligation kit (FIG. 9-(3)). The product was introduced into E. coli JM109 competent cell to separate a transformant. A plasmid was prepared from the transformant. It is confirmed by examining base sequence thereof that the expression plasmid pAIP was constructed as designed. The E. coli JM109 strain retaining pAIP was internationally deposited in National Institute of Bioscience and Human-Technology located at 1–3, Higashi 1-chome, Tsukuba-shi, Ibaraki-ken Japan, on Nov. 15, 1995 as FERM BP-5293.

EXAMPLE 2

Expression of Chimeric Protein in E. coli

E. coli JM109 transformant strain retaining a plasmid pAIP was placed on 5 ml of Terrific Broth (TB medium; 1.2% bactotrypton, 2.4% yeast extract, 0.4% glycerol, $KH_2PO_4$ 2.31 g/l, $K_2HPO_4$ 12.54 g/l) containing 100 μg/ml of ampiciline (Amp) and shaken for culture at 37° C. overnight. The culture medium was transferred into 50 ml of fresh TB medium (100 μg/ml of Amp) and precultured for 4 hours. The culture was transferred to 400 ml of TB medium (100 μg/ml of Amp) to maintain cultivation. IPTG was added thereto to a final concentration of 0.5 mM, when $OD_{600}$ (absorbance of culture medium at 600 nm) was reached to about 0.5. The mixture was further cultured overnight.

Bacterial cells were collected by centrifugation (10,000× g, 5 minutes) and washed with lysis buffer (50 mM Tris-HCl, pH 8.0, 50 mM NaCl, 1 mM EDTA). Bacterial cells were collected by centrifugation and resuspended in 50 ml of lysis buffer containing 0.25 mg/ml of lysozyme. After standing at 0° C. for 1 hour, bacterial cells were disrupted with ultrasonic wave. The disrupted lysate was then centrifuged (4,400×g, 5 minutes) to obtain an insoluble precipitation fraction. The precipitation fraction was washed with lysis buffer, and then washed with 0.5% Triton X-100, 10 mM EDTA (pH 8.0) aqueous solution and finally washed with lysis buffer to purify an inclusion body fraction.

The inclusion body fraction was dissolved in 20 ml of 6 M guanidine hydrochloride, 50 mM Tris-HCl (pH 7.0), 1 mM EDTA and 1% 2-mercaptoethanol solution, to which one liter of refolding buffer (1 M guanidine hydrochloride, 50 mM Tris-HCl, pH 7.0, 1 mM EDTA, 2 mM reduced form glutathione, 0.2 mM oxidized form glutathione) was added, and then allowed to stand at room temperature overnight. The refolding solution was sufficiently dialyzed against 20 mM phosphate buffer (pH 6.5) as an outer solution.

Insoluble matter of dialyzed refolding solution was removed with Wattman No. 2 filter paper, and further filtered with a membrane filter of pore size 0.22 μm. The resulting solution was added to a bufferized ion-exchange membrane chromatography cartridge (SP MemSep 1000, MILLIPORE). Adsorbed fractions were eluted by linear concentration gradient using 0 to 1 M sodium chloride (20 mM phosphate buffer, pH 6.5). The fractions were concentrated with centrifugal ultra filter (Centriplus concentrators; fractional molecular weight 3,000, Amicon), and then added to Superdex 75 (HiLoad 26/60, Pharmacia) equilibrated with 0.2 M NaCl and 50 mM phosphate buffer (pH 6.5) for gel filtration. Peak fractions of absorbance at 280 nm were collected and dialyzed against 20 mM phosphate buffer (pH 6.5) as an outer solution. The resulting solution was added to an ion-exchange column (RESOURCE S, Pharmacia) previously equilibrated with 20 mM phosphate buffer (pH 6.5). An adsorbed ATFHI was chromatographically eluted by linear concentration gradient using 0 to 0.5 M sodium chloride solution (20 mM phosphate buffer, pH 6.5).

EXAMPLE 3

Confirmation of Purified ATFHI

Examination of purified ATFHI by 20% SDS-PAGE confirmed a single band corresponding to 21.5 kDa calculated based on the amino acid sequence thereof. In addition, it was confirmed by transferring the protein in electrophoresis gel to membrane according to western blotting method to check a reactivity between the protein and the antiserum that the protein band corresponding to 21.5 kDa strongly reacted with antiserum against HI-8. Furthermore, an expected N-terminal sequence of ATFHI consisting of 14 amino acids, Ser-Asn-Glu-Leu-His-Gln-Val-Pro-Ser-Asn-(Cys)-Asp-(Cys)-Leu (SEQ ID NO: 78), except for Cys was confirmed by checking an N-terminal amino acid sequence thereof with a protein sequencer (Model 477A, Applied Biosystems). The results confirmed that initiation methionine was removed as expected, when ATFHI was directly expressed within E. coli.

EXAMPLE 4

Preparation of Chimeric Protein ATFHI-CL

Figure 12:
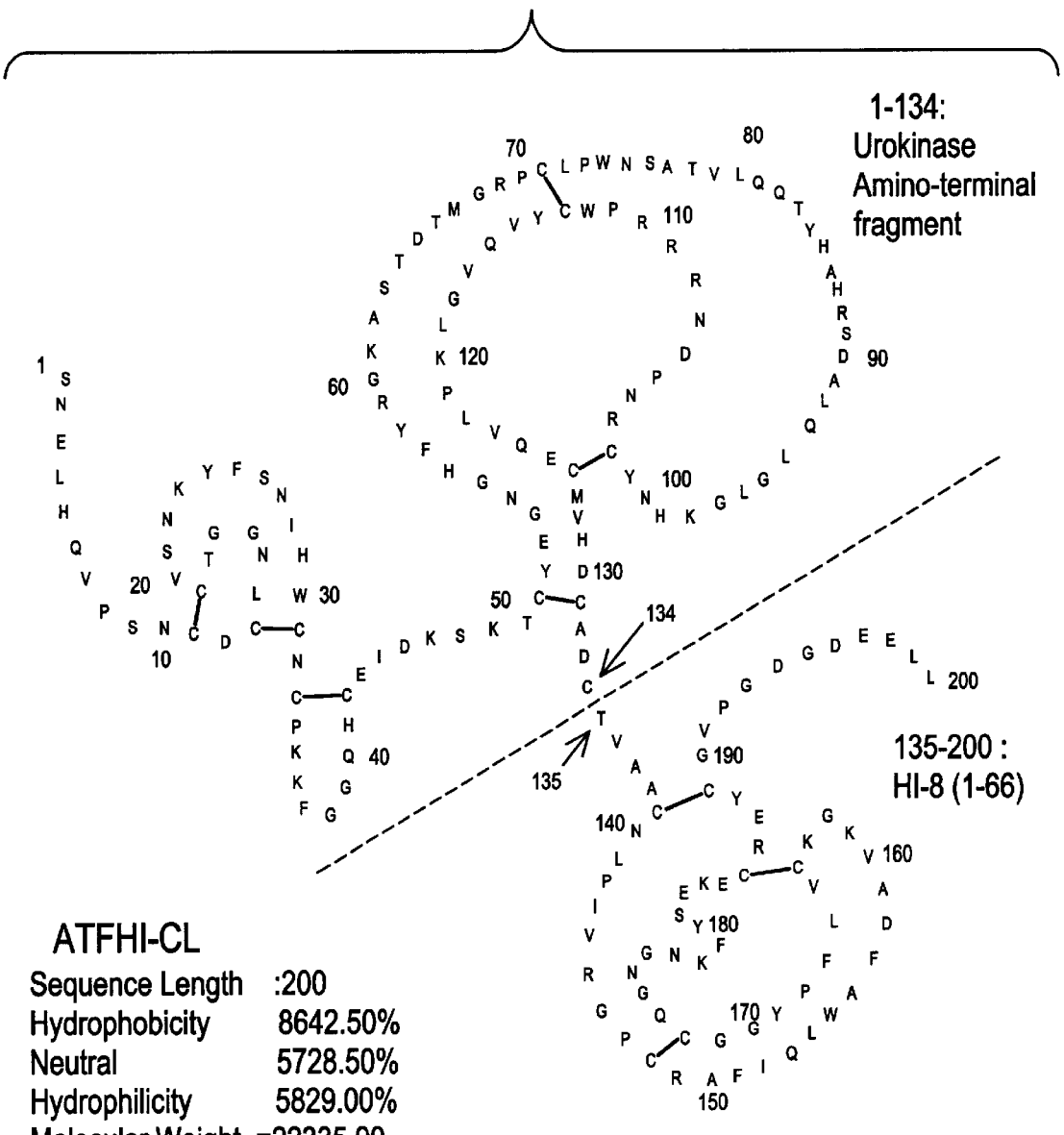
FIG. 12 shows a primary structure of chimeric protein ATFHI-CL (SEQ ID NO: 96).
Figure 13:
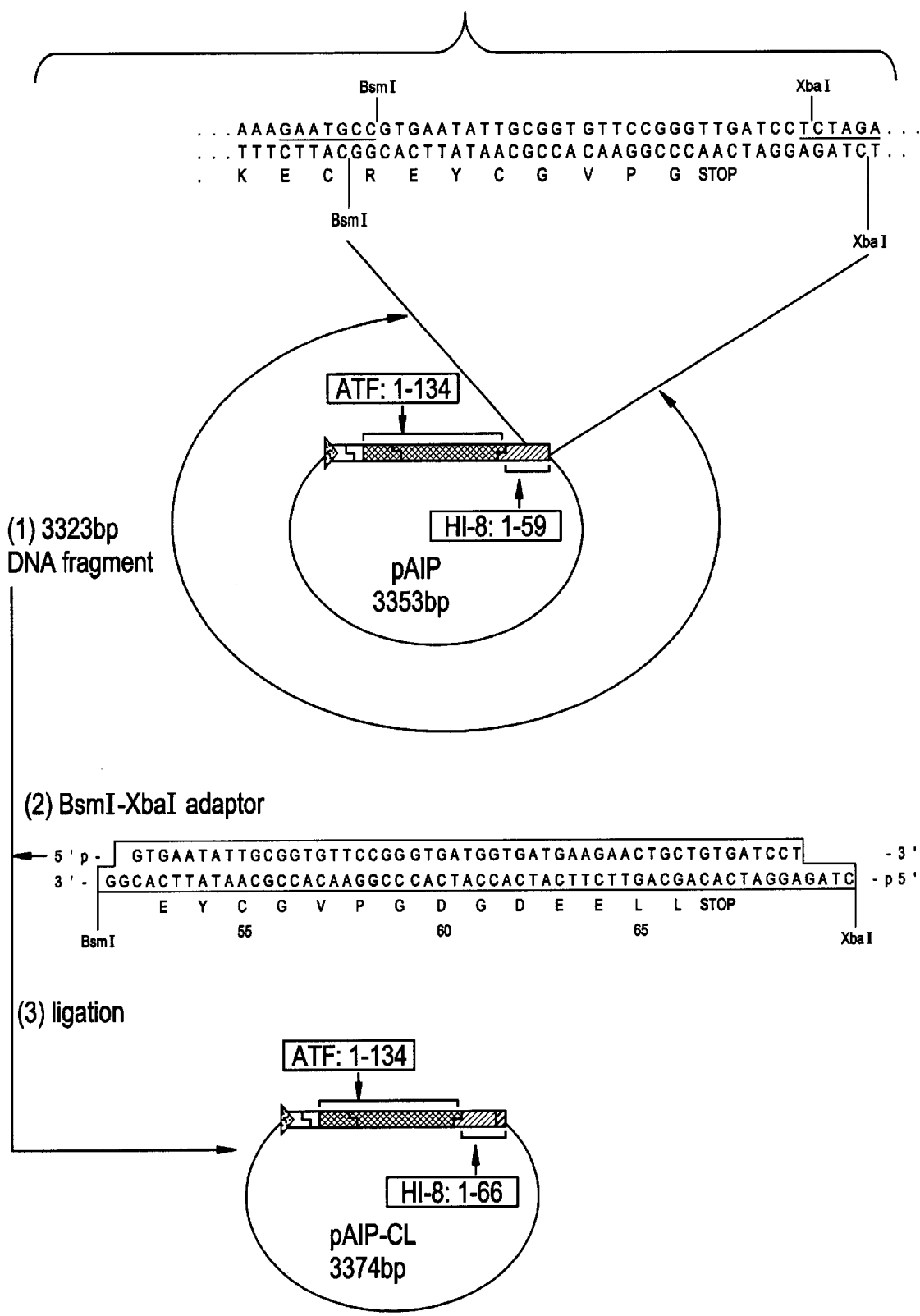
FIG. 13 shows a procedure to construct plasmid pAIP-CL (coding sequence of 3' end of HI-8 UTI DNA fragment—SEQ ID NO: 93; non-coding sequence of 3' end of HI-8 UTI DNA fragment—SEQ ID NO: 94; amino acid sequence of 3' end of HI-8 UTI DNA fragment—SEQ ID NO: 106; coding sequence of BsmI-XbaI HI-8 UTI adapter—SEQ ID NO: 12; non-coding sequence of BsmI-XbaI HI-8 UTI adapter—SEQ ID NO: 13; amino acid sequence of BsmI-XbaI HI-8 UTI adapter—SEQ ID NO: 107).

ATFHI-CL is a chimeric protein having a polypeptide of 1–134 amino acid sequence of uPA ($Ser^1$ to $Gly^{134}$) on the side of N-terminal and a polypeptide of 66 amino acid sequence of HI-8 ($Thr^1$ to $Leu^{66}$) on the side of C-terminal (FIG. 12; SEQ ID NO: 96). An expression plasmid pAIP-CL to prepare the chimeric protein in E. coli was produced according to the following process (FIG. 13). A plasmid pAIP was cleaved with restriction enzymes, BsmI and XbaI, and dephosphorylated by BAP treatment. A DNA fragment having 3323 bp was purified by separating the mixture using 1% agarose gel electrophoresis (FIG. 13-(1)). The following two synthetic DNAs are complementary with each other, and form a BsmI cohesive end on 5' side and a XbaI cohesive end on 3' side:

5'-GTGAATATTGCGGTGTTCCGGGTGATGGTGATG AAGAACTGCTGTGATCCT-3', SEQ ID NO: 12;

5'-CTAGAGGATCACAGCAGTTCTTCATCACCATCA CCCGGAACACCGCAATATTCACGG-3', SEQ ID NO: 13.

5' ends of the chemically synthesized DNAs were phosphorylated with T4 polynucreotidekinase (TAKARA) and ATP, boiled at 100° C. for 2 minutes and then cooled spontaneously for annealing to form adaptor DNA (FIG. 13-(2)). 10 pmol of the BsmI-XbaI adapter DNA and 100 ng of the DNA fragment having 3323 bp were ligated with a ligation kit (FIG. 13-(3)). The product was introduced into E. coli JM109 competent cell to separate a transformant. It is confirmed by checking a base sequence of the plasmid prepared from the transformant thus obtained that a desired plasmid pAIP-CL was constructed as designed. The E. coli JM109 strain retaining pAIP-CL was domestically deposited in National Institute of Bioscience and Human-Technology located at 1–3, Higashi 1-chome, Tsukuba-shi, Ibaraki-ken Japan, on Dec. 22, 1995 as FERM P-15364, and transferred to an international deposition on Nov. 14, 1996 as FERM BP-5746. The E. coli with the plasmid was cultured to purify a chimeric protein ATFHI-CL according to a procedure of example 2. It was confirmed by 20% SDS-PAGE that the purified ATFHI-CL was a single band corresponding to a molecular weight of 22.3 kDa as determined by calculation. It was confirmed that the protein band corresponding to 22.3k Da strongly reacted with antiserum against HI-8, by transferring the protein in electrophoresis gel to membrane according to western blotting method, followed by examining a reactivity of the protein to antiserum against HI-8.

EXAMPLE 5

Preparation of Chimeric Protein ATFHI-ML

Figure 14:
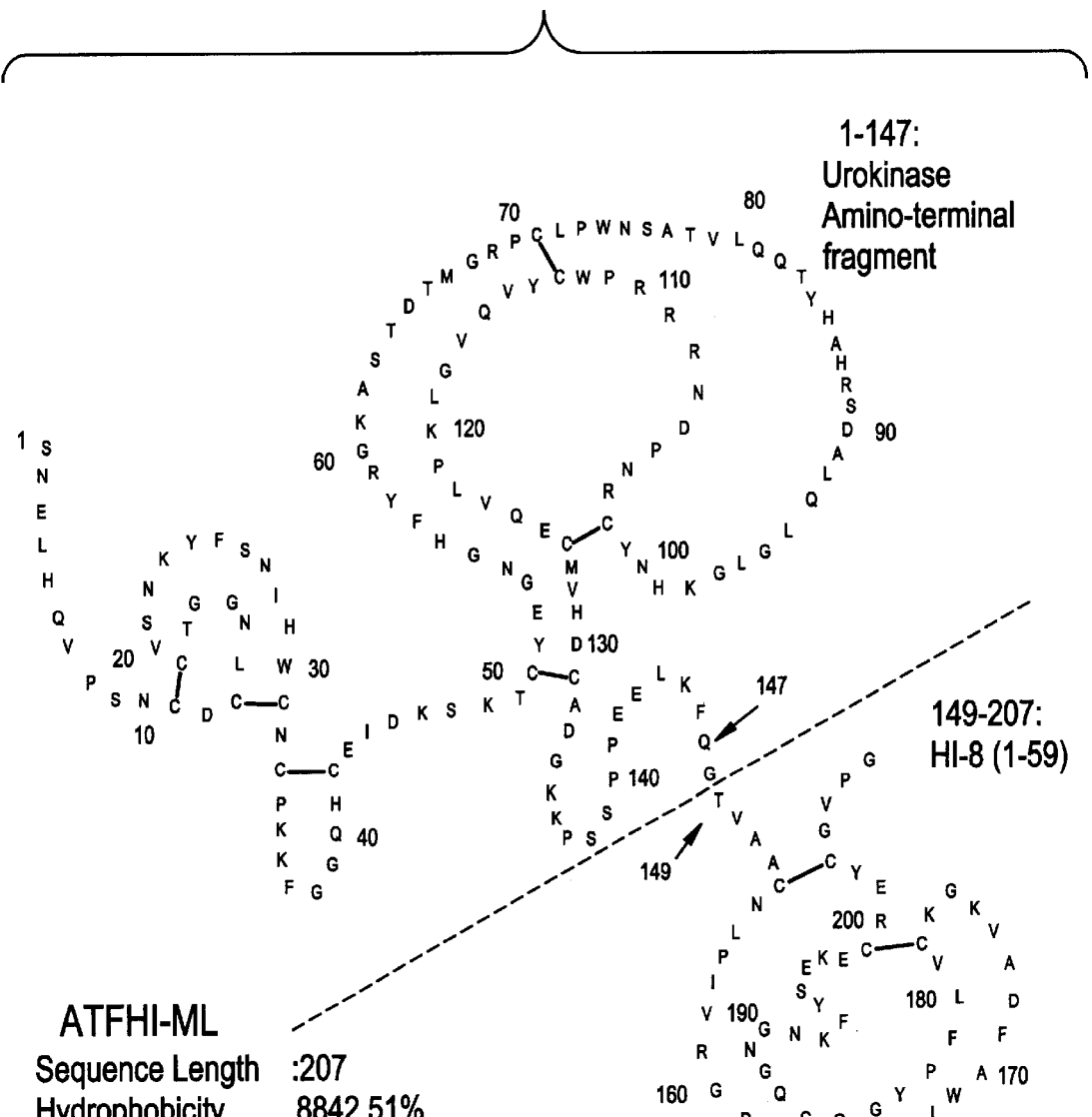
FIG. 14 shows a primary structure of chimeric protein ATFHI-ML (SEQ ID NO: 98).
Figure 15:
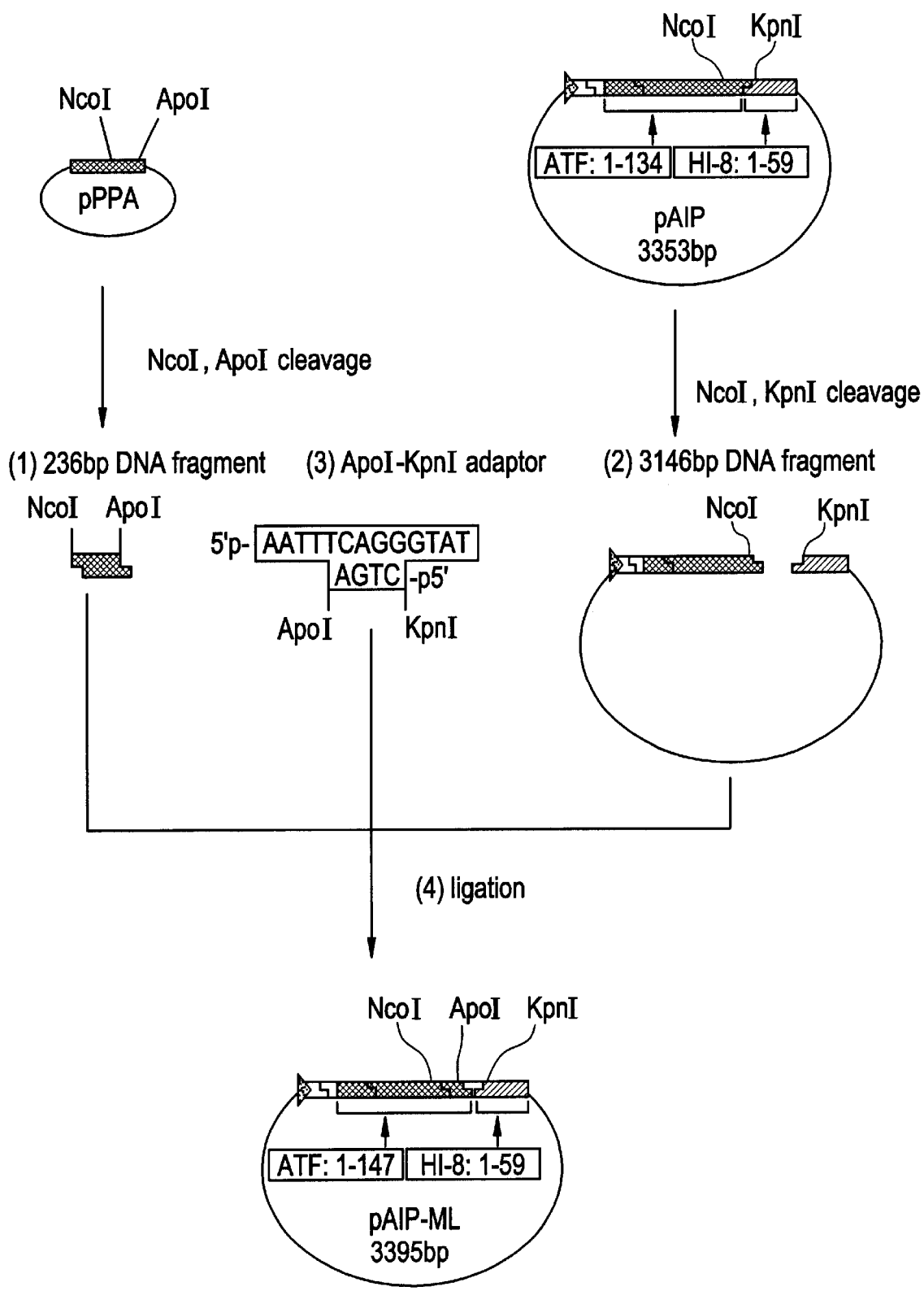
FIG. 15 shows a procedure to construct plasmid pAIP-ML (coding sequence of ApoI-KpnI adapter—SEQ ID NO: 14; non-coding sequence of ApoI-KpnI adapter—SEQ ID NO: 15).

ATFHI-ML is a chimeric protein having a polypeptide of 1–147 amino acid sequence of uPA (Ser$^1$ to Gln$^{147}$) on the side of N-terminal and a polypeptide of 1–59 amino acid sequence of HI-8 (Thr$^1$ to Gly$^{59}$) on the side of C-terminal (FIG. 14; SEQ ID NO: 98). An expression plasmid pAIP-ML to prepare the chimeric protein in *E. coli* was prepared according to the following process (FIG. 15). A plasmid pPPA was cleaved with restriction enzymes ApoI and NcoI and then separated by 3% agarose gel electrophoresis. A DNA fragment having 236 bp was cut and purified from the gel (FIG. 15-(1)). A plasmid pAIP was cleaved with NcoI and KpnI and separated by 1% agarose gel electrophoresis to purify a DNA fragment having 3146 bp (FIG. 15-(2)). The following two synthetic DNAs are complementary with each other, and form a ApoI cohesive end on 5' side and a KpnI cohesive end on 3' side. 5' ends of the chemically synthesized DNAs, 5'-AATTTCAGGGTAT-3' (SEQ ID NO: 14) and 5'-CCTGA-3' (SEQ ID NO: 15) were phosphorylated with T4 polynucleotidekinase (TAKAPA) and ATP, boiled at 1 00° C. for 2 minutes and then cooled spontaneously for annealing to form adaptor DNA (FIG. 15-(3)). 30 pmol of the ApoI-KpnI adapter DNA and 100 ng portions of each DNA fragments having 236 bp and 3146 bp were ligated with a ligation kit (FIG. 15-(4)). The product was introduced into *E. coli* JM109 competent cell to separate a transformant. It is confirmed by checking a base sequence of a plasmid prepared from the transformant thus obtained that a desired plasmid pAIP-ML was constructed as designed. The *E. coli* JM109 strain retaining pAIP-ML was domestically deposited in National Institute of Bioscience and Human-Technology located at 1-3, Higashi 1-chome, Tsukuba-shi, Ibaraki-ken Japan, on Dec. 22, 1995 as FERM P-15363, and transferred to an international deposition on Nov. 14, 1996 as FERM BP-5745.

The *E. coli* with the plasmid was cultured to purify a chimeric protein ATFHI-ML according to a procedure of example 2. It was confirmed by 20% SDS-PAGE that the purified ATFHI-ML was a single band corresponding to a molecular weight of 23.1 kDa as determined by calculation. It was confirmed that the protein band corresponding to 23.1 kDa strongly reacted with antiserum against HI-8, by transferring the protein in electrophoresis gel to membrane according to western blotting method, followed by examining a reactivity of the protein to antiserum against HI-8.

EXAMPLE 6

Plasmin Inhibition Experiment

Figure 16:
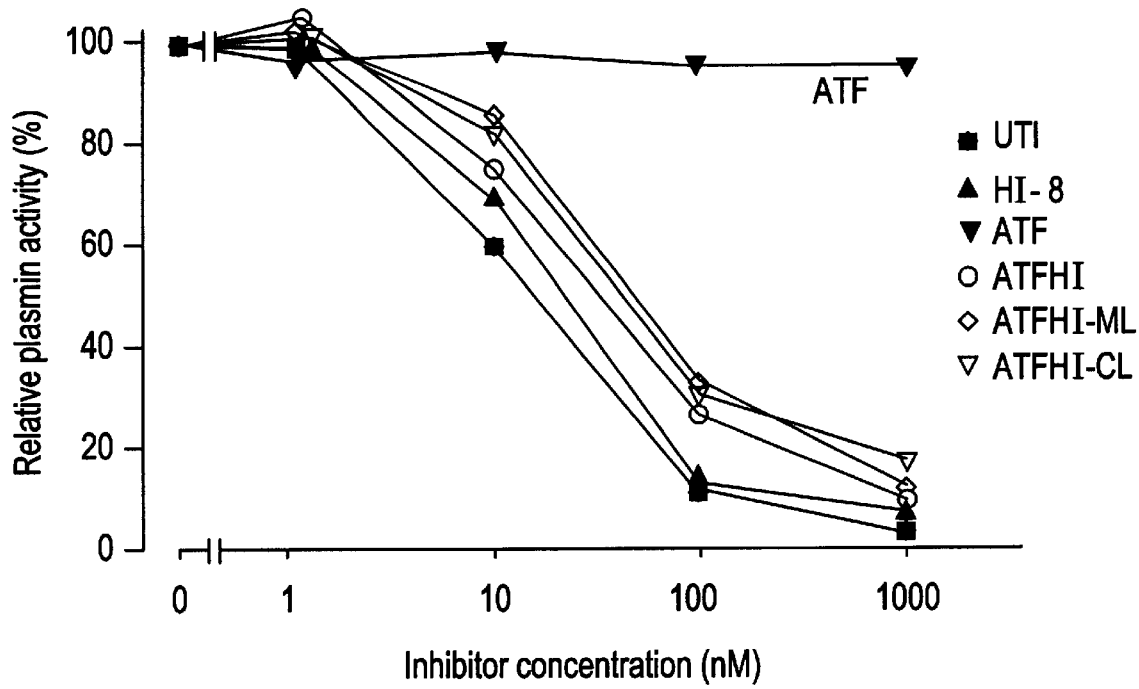
FIG. 16 shows a plasmin inhibition ($IC_{50}$) effect of chimeric proteins.

140 μl of PBS, 20 μl of a 6.25 μM plasmin aqueous solution and 20 μL of 0–10 μM sample were added to each well of 96-well microtiter plate in this sequence. After maintaining temperature at 23° C. for 5 minutes, 20 μl of a synthetic substrate S-2251 solution (1 mg/ml) was added thereto to start a reaction. After 30 minutes, 20 μl of 20% acetic acid was added to stop the rection. Absorbance at 405 nm was determined to graphically indicate a relative ratio of the absorbance to an absorbance without addition of an inhibitor (FIG. 16). As a result, although the chimeric protein was weaker than UTI and HI-8 (½ to ⅓ of IC$_{50}$), the chimeric proteiti had a similar types of plasmin inhibitory activity, which confirmed that the chimeric protein maintained characteristics of HI-8.

EXAMPLE 7

Experiment on Inhibition of uPAR Binding

Figure 17:
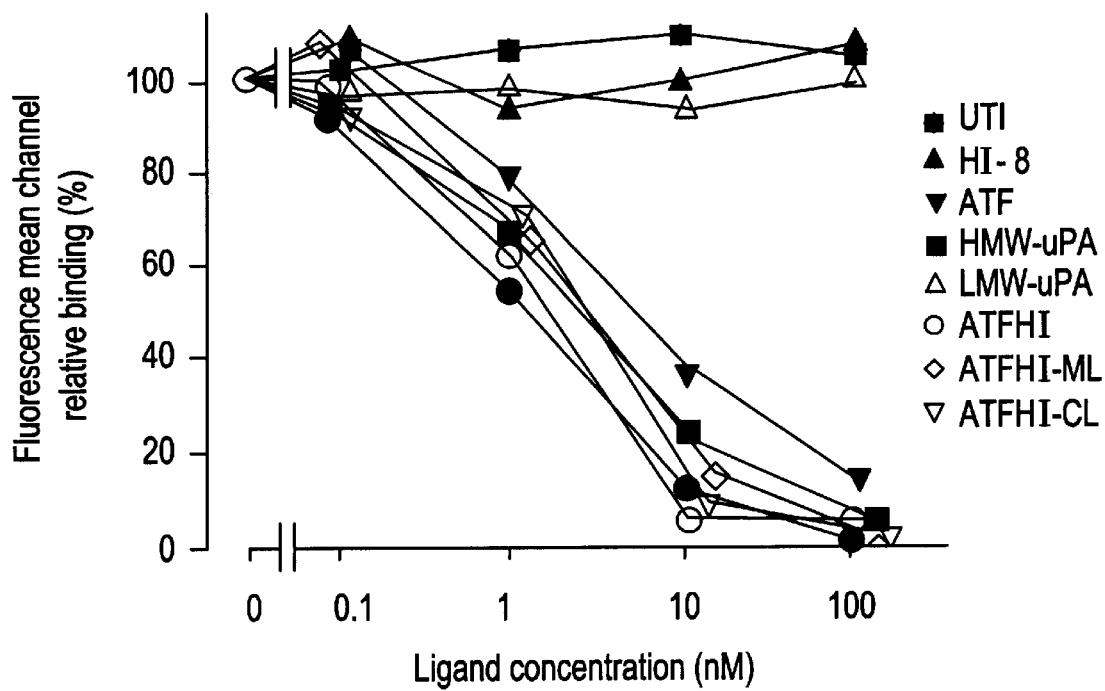
FIG. 17 shows a binding effect of chimeric proteins to U937 cell.

An experiment on inhibition of uPA binding to a receptor (uPAR) by a chimeric protein was conducted using human histocytic lymphoma strain U937. A fluorescein isothiocyanate (FITC)-labelled uPA as ligand was prepared as follows. 10 mg of uPA was dissolved in 2 ml of 0.1 M NaHCO$_3$ (pH 9.0). A solution of 1 mg FITC in 1 ml of dimethylsulphoxide (DMSO) was added to the solution and mixed. After stirring and mixing the solution at room temperature for 3 hours, the mixture was subjected to a gel filtration column for desalting (PD-10, Pharmacia) to purify FITC-labelled uPA. U937 cells stimulated by phorbol 12-myristate 13-acetate (PMA, Sigma) was collected, acid-treated with 50 mM glycine-HCl and 0.5 M NaCl (pH 3.0), and then neutralized with 0.5 M HEPES buffer and 0.1 M NaCl (pH 7.5). Endogenous uPA bound to uPAR may be removed by the treatment. PBS (398 μl) containing 0–1,000 nM of sample (100 μl), 2 μl of 1 mg/ml FITC-labeled uPA and 0.1% BSA was added to 500 μl of U937 cell, which was adjusted to 1×10$^6$ cells/ml (0.1% BSA, PBS). The mixture was allowed to stand at 4° C. for 30 minutes. The amount of FITC-labelled uPA bound to the cell was determined with EPICS PROFILE flow cytometry. The results confirmed that the chimetic protein ATFHI had an inhibitory effects on binding of labelled uPA similar to unlabelled uPA. (FIG. 17). The results confirmed that the chimeric protein maintained a G domain function of uPA.

EXAMPLE 8

Experiment on Inhibition of Cancer Cell Invasion in vitro

In the experiment on inhibition of invasion, culture cells of human ovarian cancer cell line HOC-1, human choriocarcinoma cell line SMT-ccl, human breast cancer cell line MDA-MB-435, human malignant melanoma cell line A375, human prostatic cancer cell line PC-3, DU-145, human colon cancer cell line GE0 and mouse Lewis lung tumor cell line 3LL were used.

100 μl of Matrigel diluted 20-fold with PBS was added to a cup provided with polycarbonate filter (8 μm pore size) (Transwell, COSTER), and dried for coating the filter surface. 600 μl of RPMI 1640 and 0.1% BSA was added to a lower side of modified Boyden chamber. 100 μl of sample whose concentration was adjusted variously with serum-free medium was added to an upper side of chamber (cup provided with filter). After maintaining temperature at 23° C. for 1 hour, 100 μl of cancer cell suspension (2×10$^6$ cells/ml) was added to an upper side of chamber. Fibroblast conditioned-medium as chemotactic substance was added to a lower side of chamber. The chamber was transferred to 5% CO$_2$ incubator for culture at 37° C. for 12 hours. Cells remained on upper side of filter were swabbed and then the filter was stained. The number of cells invaded into lower side of filter was counted under microscope to determine a sample concentration (ID$_{50}$) at which the number of invasion cells were half (table 1). The experiment was independently repeated 3 times under the same conditions, respectively. The amount of uPAR expressed on each culture cell was determined by calculation of Scatchard plot using iode-labelled uPA.

The results demonstrate that the chimeric protein has similar effects on a cancer cell derived from mouse 3LL to UTI and HI-8 and more potent invasion inhibitory effects on human cancer cells than UTI and HI-8. This confirms that the chimeric protein specifically binds to human uPAR and that the chimeric protein has more potent effects than a crosslinked compound (ATF+HI-8 conjugate on table 1) prepared by combining ATF and HI-B by a crosslinking agent (N-succinimidyl-3-(2-pyridyldithio)propionate) (32). The inhibitory effect of chimeric protein is proportional to the amount uPAR expressed on each cell. The chimeric protein indicates a higher inhibitory effect on SMT-ccl and DU-145 and like cells having an increased amount of expressed uPAR.

TABLE 1

Invasion inhibitory effect on each culture cell $ID_{50}$ (nM)

| cell | UTI | HI-8 | ATF | ATF + HI-8 conjugate | ATFHI | ATFHI-CL | ATFHI-ML | uPAR site/cell |
|---|---|---|---|---|---|---|---|---|
| H0C-I | 200 | 180 | 1000 | 70 | 10 | 20 | 50 | 76000 |
| SMT-ccl | 100 | 220 | 500 | 10 | 1.2 | 1 | 10 | 108000 |
| A375 | 80 | 100 | 1000 | 80 | 50 | 100 | 120 | 12000 |
| MDA-MB-435 | 70 | 110 | 800 | 30 | 3.5 | 20 | 5.6 | 87000 |
| GE0 | 300 | 200 | >1000 | 150 | 110 | 200 | 20 | 5000 |
| PC-3 | 50 | 50 | >1000 | 20 | 20 | 20 | 50 | 20000 |
| DU-145 | 260 | 150 | 300 | 30 | 0.5 | 5 | 2.9 | 96000 |
| 3LL | 250 | 200 | >1000 | 200 | 300 | 300 | 200 | N.D. |

EXAMPLE 9

Experiment on Metastasis Inhibition of Human Cancer Cell in Nude Mouse

Nude mice (Balb/c nu/nu, Charles River Japan) were fed in sterilized room giving sterilized food and water. A suspension of $1 \times 10^7$ prostatic cancer PC-3 cells in 0.2 ml of Dullbecco's modified Eagle medium (DMEM) was transplanted to 5-week-aged male mouse subcutaneously. 50 μg of ATFHI or physiological saline was injected subcutaneously after 0, 7 and 14 days from transplanted day, respectively. After 6 weeks from transplantation of HOC-1 tumor, subcutaneous tumor was removed by operation, and metastasized tumor in lymph node was observed. In the experiment, as shown in table 2, metastasis in lymph node was observed in about half tumor-inoculated mouse (16/31), and ATFHI inhibited the metastasis significantly (3/20).

TABLE 2

| Sample | Cell | Method of Inoculation | Cell Number | Metastasis Population |
|---|---|---|---|---|
| Saline | PC3 | s.c. | $1 \times 10^7$ | 16/31 |
| ATFHI | PC3 | s.c. | $1 \times 10^7$ | 3/20 |

EXAMPLE 10

Cytotoxicity in vitro

Cytotoxicity of ATFHI to uPAR expressing cells was examined by observation of growth inhibition of culture cells. $2 \times 10^4$ of culture cells (HOC-1, SMT-cc1, PC-3, 3LL) were cultured overnight in 96-well plate. Medium was changed to a leucine (-) medium containing a various concentration of ATFHI, ATF or HI-8. After culture at 37° C. for 20 hours, 1 μCi of ($^3$H) leucine was added thereto, and then the cells were cultured for further 6 hours. The cells collected were disrupted by freeze and thawing, to determine radioactive leucine incorporated during protein synthesis with Betaplate scintillation counter, Pharmacia. The results indicate that ATFHI does not kill cells at concentration of 20 μg/ml (about 1 μM) and does not affect protein synthesis.

EXAMPLE 11

Activation of Cell Growth in vitro 1 ml of cell solution containing 1,000 cancer cells (HOC-1, SMT-cc1, PC-3LL) was placed in each well of 24-well plate and cultured. After 24 hours, a variety concentrations of ATFHI diluted with PBS containing 0.2% human serum albumin was added thereto. After culture for further 7 days, cells were stained and observed under microscope. The results confirm that the chimeric protein do not activate growth of cancer cells.

References (1) to (44) are Shown Below (1) Naohiko Koshikawa, Kaoru Miyazaki: JIKKENIGAKU, 12: 8, 71–76, 1994;
(2) Motoo Nakajima: JIKKENIGAKU, 12: 8, 77–85, 1994;
(3) Unkeless, J., Dano, K., Kellerman, G. M. and Reich, E.: J. Biol. Chem., 249: 4295–4305, 1994;
(4) Hasui, Y., Suzumiya, J., Marutsuka, K., Sumiyoshi, A., Hashida, S. and Ishikawa, E.: Cancer Res., 49: 1067–1070, 1989;
(5) Mignatti, P., Robbins, E. and Rifkin, D. B. :Cell, 47: 487–498, 1986;
(6) Appella, E., Robinson, E. A., Ullrich, S. J., Stoppelli, M. P., Corti, A., Cassanni, G. and Blasi, F.: J. Biol. Chem., 262: 4437–4440, 1987;
(7) Ossowski, L.: Cancer Res., 52: 6754–6760, 1992
(8) Bruckner, A., Filderman, A. E., Kirchheimer, J. C., Binder, B. R. and Remold, H. G.: Cancer Res., 52: 3043–3047, 1992;
(9) Pyke, C., Graem, N., Ralfkiaer, E., Ronne, E., Hoyer-Hansen, G., Brunner, N. and Dano, K.: Cancer Res., 53: 1911–1915, 1993;
(10) Stahl, A. and Mueller, B. M.: Cancer Res., 54: 3066–3071, 1994;
(11) Behrendt, N., Ronne, E. and Dano, K.: Biol. Chem. Hoppe-Seyler, 376: 269–279, 1995;
(12) Estreicher, A., Muhlhauser, J., Carpentier, J.-L., Orci, L. and Vassalli, J.-D.: J. Cell Biol., 111:783–792, 1990;
(13) Blasi, F. and Verde, P.: Seminar in Cancer Biology, 1:117–126, 1990;
(14) Mackay, A. R., Corbitt, R. H., Hartzler, J. L. and Thorgeirsson, U. P.: Cancer Res., 50: 5997–6001, 1990;
(15) Motoo, Nakajima: JIKKENIGAKU, 10: 4, 37–43, 1992;

(16) Yasushi Sato: JIKKENIGAKU, 13: 2, 25–28, 1995;
(17) Falcone, D. J., McCaffrey, T. A., Haimovitz-Friedman, A. and Garcia, M.: J. Cell Physiol., 155: 595–605, 1993;
(18) Kobayashi, H., Gotoh, J., Shinohara, H., Moniwa, N. and Terao, T.: Thrombosis and Haemostasis, 71: 4, 474–480, 1994.
(19) Laug, W. E., Cao, X. R., Yu, Y. B., Shimada, H. and Kruithof, E. K. O.: Cancer Res., 53: 6051–6057, 1993;
(21) Mohanam, S, Sawaya, R., McCutcheon, I., Ali-Osman, F., Boyd, D. and Rao, J. S.: Cancer Res., 53: 4143–4147, 1993;
(22) Kobayashi, H., Ohi, H., Shinohara, H., Sugimura, M., Fujii, T., Terao, T., Schmitt, M., Goretzki, L., Chucholowski, N., Janicke, F. and Graeff, H.: Br. J.Cancer, 67: 537–544, 1993;
(23) Kobayashi, H., Gotoh, J., Fujie, M., Shinohara, H., Moniwa, N. and Terao, T.: Int. J. Cancer, 57: 727–733, 1994;
(24) Crowley, C. W., Cohen R. L., Lucas, B. K., Liu, G., Shuman, M. A. and Levinson, A. D.: Proc. Natl. Acad. Sci. USA, 90: 5021–5025, 1993;
(25) Lu, H., Yeh, P., Guitton, J.-D., Mabilat, C., Desanlis, F., Maury, I., Legrand, Y., Soria, J. and Soria C.: FEBS Letters, 356: 56–59, 1994;
(26) GB Patent No. 2,246,779 B;
(27) Kobayashi, H., Fujie, M., Shinohara, H., Ohi, H., Sugimura, M. and Terao, T.: Int. J. Cancer, 57: 378–384, 1994;
(28) Kobayashi, H., Shinohara, H., Ohi, H., Sugimura, M., Terao, T. and Fujie M.: Clin. Exp. Metastasis, 12:117–128, 1994;
(29) Kobayashi, H., Shinohara, H., Takeuchi, K., Itoh, M., Fujie, M., Saitoh, M. and Terao, T.: Cancer Res., 54: 844–849, 1994;
(30) Wachter, E. and Hochstrasser, K.: Hoppe-Seyler's Z. Physiol. Chem., 362:1351–1355, 1981;
(31) Kobayashi, H., Gotoh, J., Kanayama, N., Hirashima, Y., Terao, T. and Sugino, D.: Cancer Res., 55: 1847–1852, 1995;
(32) Kobayashi, H., Gotoh, J., Hirashima, Y., Fujie, M., Sugino, D. and Terao, T.: J. Biol. Chem., 270: 8361–8366, 1995;
(33) Ohnishi, H., Kosuzume, H., Ashida, Y., Kato, K. and Honjo, I.: Dig. Dis. Sci., 29: 26–32, 1984;
(34) Ohnishi, H., Suzuki, K., Niho, T., Ito, C. and Yamaguchi, K.: Jpn. J. Pharmacol., 39:13–144, 1985;
(35) Hashimoto, Masakatsu, et al.: IGAKUTOYAKUGAKU, 13:1091–1096, 1985;
(36) Kojyaku, Koji, et al.: IGAKUNOAYUMI, 125:187–190, 1983;
(37) Tsunazawa Susumu: TANPAKUSHITSUKAKUSANKOSO, 40: 389–398, 1995;
(38) Hibino, Y., Miyaku, T., Kobayashi, Y., Ohinori, M., Miki, T., Matsumoto, R., Numao, N. and Kondo, K.: Agric. Biol. Chem., 52: 329–336, 1988;
(39) U.S. Pat. No. 5,112,755;
(40) Japanese Examined Patent Publication H5-52189;
(41) Japanese Unexamined Patent Publication H5-30970;
(42) Japanese Unexamined Patent Publication H5-91877;
(43) Japanese Unexamined Patent Publication H5-336965;
(44) Kaumeyer, J. F., Polazzi, J. O. and Kotick, M. P.: Nucl. Acids Res., 14: 7839–7850, 1986.

---

What is claimed is:

1. A chimeric protein comprising a sequence of the following formula 1 on N-terminal side and a sequence of the following formula 2 on C-terminal side:

formula 1:
  Cys Asp Cys Leu Asn Gly Gly Thr Cys Val Ser Asn Lys Tyr Phe Ser Asn Ile His Trp Cys Asn Cys Pro Lys Lys Phe Gly Gly Gln His Cys (SEQ ID NO: 18)

formula 2:
  Cys Asn Leu Pro Ile Val Arg Gly Pro Cys Arg Ala Phe Ile Gln Leu Trp Ala Phe Asp Ala Val Lys Gly Lys Cys Val Leu Phe Pro Tyr Gly Gly Cys Gln Gly Asn Gly Asn Lys Phe Tyr Ser Glu Lys Glu Cys Arg Glu Tyr Cys (SEQ ID NO: 19), wherein an intervening sequence having between about one and 110 amino acids, and having little or no effect on the steric structure of either the sequence of formula 1 or the sequence of formula 2, is inserted.

2. The chimeric protein according to claim 1 which further comprises an intervening sequence containing any one of the following 4 sequences between said formula 1 and said formula 2:

(formula 3)-Ala Asp Gly Thr Val Ala Ala (SEQ ID NO: 27)
  (formula 3)-Ala Asp Gly Lys Lys Pro Ser Ser Pro Pro Glu Glu Leu Lys Phe Gln Gly Thr Val Ala Ala (SEQ ID NO: 38);
  Glu Ile Asp Lys Ser Lys Thr Thr Val Ala Ala (SEQ ID NO: 39); and
  Glu Ile Asp Lys Ser Lys Thr Val Ala Ala (SEQ ID NO: 40)

wherein formula 3 is as follows:

Formula 3:
  Glu Ile Asp Lys Ser Lys Thr Cys Tyr Glu Gly Asn Gly His Phe Tyr Arg Gly Lys Ala Ser Thr Asp Thr Met Gly Arg Pro Cys Leu Pro Trp Asn Ser Ala Thr Val Leu Gln Gln Thr Tyr His Ala His Arg Ser Asp Ala Leu Gln Leu Gly Leu Gly Lys His Asn Tyr Cys Arg Asn Pro Asp Asn Arg Arg Arg Pro Trp Cys Tyr Val Gln Val Gly Leu Lys Pro Leu Val Gln Glu Cys Met Val His Asp Cys (SEQ ID NO: 62).

3. The chimeric protein according to claim 1 comprising a sequence represented by formula A:

N terminal-sequence I-formula 1-sequence II-formula 2-sequence III-C terminal in which formula 1 and formula 2 are as defined above, and sequence I represents a hydrogen atom or any one of the following amino acid sequences:

(SEQ ID NO:20)
Ser Asn Glu Leu His Gln Val Pro Ser Asn (SEQ ID NO:21)
Asn Glu Leu His Gln Val Pro Ser Asn (SEQ ID NO:22)
Glu Leu His Gln Val Pro Ser Asn (SEQ ID NO:23)
Leu His Gln Val Pro Ser Asn (SEQ ID NO:24)
His Gln Val Pro Ser Asn (SEQ ID NO:25)
Gln Val Pro Ser Asn (SEQ ID NO:26)
Val Pro Ser Asn

Pro Ser Asn

Ser Asn

Asn sequence II represents any one of the sequences selected from a group containing formula 3 and a group not containing formula 3 a group containing formula 3:
  (formula 3)-Ala Asp Gly Thr Val Ala Ala (SEQ ID NO: 27)
  (formula 3)-Ala Asp Gly Val Ala Ala (SEQ ID NO: 28)
  (formula 3)-Ala Asp Gly Ala Ala (SEQ ID NO: 29)
  (formula 3)-Ala Asp Gly Xaa (SEQ ID NO: 30)
  (formula 3)-Ala Asp Thr Val Ala Ala (SEQ ID NO: 31)
  (formula 3)-Ala Asp Val Ala Ala (SEQ ID NO: 32)
  (formula 3)-Ala Asp Ala Ala (SEQ ID NO: 33)
  (formula 3)-Ala Asp Xaa (formula 3)-Ala Thr Val Ala Ala (SEQ ID NO: 34)
(formula 3)-Ala Val Ala Ala (SEQ ID NO: 35)
(formula 3)-Xaa Thr Val Ala Ala (SEQ ID NO: 36)
(formula 3)-Xaa Val Ala Ala (SEQ ID NO: 37)
(formula 3)-Xaa Ala Ala
(formula 3)-Xaa Xaa
(formula 3)-Val Ala Ala
(formula 3)-Xaa
(formula 3)-Ala Asp Gly Lys Lys Pro Ser Ser Pro Pro Glu Glu Leu Lys Phe Gln Gly Thr Val Ala Ala (SEQ ID NO: 38)

a group not containing formula 3:
Glu Ile Asp Lys Ser Lys Thr Thr Val Ala Ala (SEQ ID NO: 39)
Glu Ile Asp Lys Ser Lys Thr Val Ala Ala (SEQ ID NO: 40)
Glu Ile Asp Lys Ser Lys Thr Ala Ala (SEQ ID NO: 41)
Glu Ile Asp Lys Ser Lys Thr Xaa (SEQ ID NO: 42)
Glu Ile Asp Lys Ser Lys Xaa (SEQ ID NO: 43)
Glu Ile Asp Lys Ser Lys Val Ala Ala (SEQ ID NO: 44)
Glu Ile Asp Lys Ser Lys Ala Ala (SEQ ID NO: 45)
Glu Ile Asp Lys Ser Thr Val Ala Ala (SEQ ID NO: 46)
Glu Ile Asp Lys Ser Val Ala Ala (SEQ ID NO: 47)
Glu Ile Asp Lys Ser Ala Ala (SEQ ID NO: 48)
Glu Ile Asp Lys Ser Xaa (SEQ ID NO: 49)
Glu Ile Asp Lys Thr Val Ala Ala (SEQ ID NO: 50)
Glu Ile Asp Lys Val Ala Ala (SEQ ID NO: 51)
Glu Ile Asp Lys Ala Ala (SEQ ID NO: 52)
Glu Ile Asp Lys Xaa (SEQ ID NO: 53)
Glu Ile Asp Thr Val Ala Ala (SEQ ID NO: 54)
Glu Ile Asp Val Ala Ala (SEQ ID NO: 55)
Glu Ile Asp Ala Ala (SEQ ID NO: 56)
Glu Ile Asp Xaa (SEQ ID NO: 57)
Glu Ile Thr Val Ala Ala (SEQ ID NO: 58)
Glu Ile Val Ala Ala (SEQ ID NO: 63)
Glu Ile Ala Ala (SEQ ID NO: 59)
Glu Ile Xaa
Glu Thr Val Ala Ala (SEQ ID NO: 60)
Glu Val Ala Ala (SEQ ID NO: 61)
Glu Ala Ala
Glu Xaa
Xaa provided that Xaa represents any amino acid constituting a protein, formula 3 represents the following sequence:
Formula 3:
Glu Ile Asp Lys Ser Lys Thr Cys Tyr Glu Gly Asn Gly His Phe Tyr Arg Gly Lys Ala Ser Thr Asp Thr Met Gly Arg Pro Cys Leu Pro Trp Asn Ser Ala Thr Val Leu Gln Gln Thr Tyr His Ala His Arg Ser Asp Ala Leu Gln Leu Gly Leu Gly Lys His Asn Tyr Cys Arg Asn Pro Asp Asn Arg Arg Arg Pro Trp Cys Tyr Val Gln Val Gly Leu Lys Pro Leu Val Gln Glu Cys Met Val His Asp Cys (SEQ ID NO: 62)

sequence III represents a hydroxyl group (—OH) or any of the following amino acid sequences:
Gly Val Pro Gly Asp Gly Asp Glu Glu Leu Leu (SEQ ID NO: 64)
Gly Val Pro Gly Asp Gly Asp Glu Glu Leu (SEQ ID NO: 65)
Gly Val Pro Gly Asp Gly Asp Glu Glu (SEQ ID NO: 66)
Gly Val Pro Gly Asp Gly Asp Glu (SEQ ID NO: 67)
Gly Val Pro Gly Asp Gly Asp (SEQ ID NO: 68)
Gly Val Pro Gly Asp Gly (SEQ ID NO: 69)
Gly Val Pro Gly Asp (SEQ ID NO: 70)
Gly Val Pro Gly (SEQ ID NO: 71)
Gly Val Pro
Gly Val
Gly.

4. The chimeric protein according to claim 3 wherein sequence II is (formula 3)-Ala Asp Gly Thr Val Ala Ala (SEQ ID NO: 27) or
(formula 3)-Ala Asp Gly Lys Lys Pro Ser Ser Pro Pro Glu Glu Leu Lys Phe Gln Gly Thr Val Ala Ala (SEQ ID NO: 38)
when selected from a group containing formula 3, and sequence II is
Glu Ile Asp Lys Ser Lys Thr Thr Val Ala Ala (SEQ ID NO: 39) or
Glu Ile Asp Lys Ser Lys Thr Val Ala Ala (SEQ ID NO: 40) when selected from a group not containing formula 3.

5. The chimeric protein according to claim 3 wherein sequence I is represented by Ser Asn Glu Leu His Gln Val Pro Ser Asn (SEQ ID NO: 20).

6. The chimeric protein according to claim 3 wherein sequence I is represented by Ser Asn Glu Leu His Gln Val Pro Ser Asn (SEQ ID NO: 20), and sequence II is
(formula 3)-Ala Asp Gly Thr Val Ala Ala (SEQ ID NO: 27) or
(formula 3)-Ala Asp Gly Lys Lys Pro Ser Ser Pro Pro Glu Glu Leu Lys Phe Gln Gly Thr Val Ala Ala (SEQ ID NO: 38)
when selected from a group containing formula 3, and sequence II is
Glu Ile Asp Lys Ser Lys Thr Thr Val Ala Ala (SEQ ID NO: 39) or
Glu Ile Asp Lys Ser Lys Thr Val Ala Ala (SEQ ID NO: 40) when selected from a group not containing formula 3.

7. A DNA coding for a chimeric protein comprising a sequence of the following formula 1 on 5' side and a sequence of the following formula 2 on 3' side: formula 1:
Cys Asp Cys Leu Asn Gly Gly Thr Cys Val Ser Asn Lys Tyr Phe Ser Asn Ile His Trp Cys Asn Cys Pro Lys Lys Phe Gly Gly Gln His Cys (SEQ ID NO: 18)

Formula 2
Cys Asn Leu Pro Ile Val Arg Gly Pro Cys Arg Ala Phe Ile Gln Leu Trp Ala Phe Asp Ala Val Lys Gly Lys Cys Val Leu Phe Pro Tyr Gly Gly Cys Gln Gly Asn Gly Asn Lys Phe Tyr Ser Glu Lys Glu Cys Arg Glu Tyr Cys (SEQ ID NO: 19).

8. The DNA according to claim 7 coding for a chimeric protein comprising a sequence represented by formula A:
N terminal-sequence I-formula 1-sequence II-formula 2-sequence Ill-C terminal in which sequence I, formula 1, sequence II, formula 2 and sequence III are as defined in claim 3 above.

9. A plasmid comprising DNA according to claim 7 or 8.

10. A tranformant into which the plasmid according to claim 9 is introduced.

11. A cancerous metastasis inhibitor comprising the chimeric protein according to any of claims 1–6 as active ingredient.

12. A method for producing a chimeric protein comprising introducing into a host cell a plasmid into which the DNA according to claim 7 or 8 is integrated to produce a transformant, culturing the transformant and recovering the chimeric protein from a culture.

13. The transformant according to claim 10 wherein said transformant is FERM BP-5293.

14. The transformant according to claim 10 wherein said transformant is FERM BP-5745.

15. The transformant according to claim 10 wherein said transformant is FERM BP-5746.

16. The protein according to claim 1 comprising an amino acid sequence which corresponds to 1–193 of SEQ ID NO: 80.

17. The protein according to claim 1 comprising an amino acid sequence which corresponds to 1–200 of SEQ ID NO: 96.

18. The protein according to claim 1 comprising an amino acid sequence which corresponds to 1–207 of SEQ ID NO: 98.

19. The DNA according to claim 7 comprising a nucleic acid sequence which corresponds to 15–593 of SEQ ID NO: 80.

20. The DNA according to claim 7 comprising a nucleic acid sequence which corresponds to 15–614 of SEQ ID NO: 96.

21. The DNA according to claim 7 comprising a nucleic acid sequence which corresponds to 15–635 of SEQ ID NO: 98.

* * * * *

SEQUENCE LISTING

```
<160> NUMBER OF SEQ ID NOS: 107

<210> SEQ ID NO 1
<211> LENGTH: 431
<212> TYPE: PRT
<213> ORGANISM: Homo sapiens
<220> FEATURE:
<221> NAME/KEY: mat_peptide
<222> LOCATION: (21)..()
<223> OTHER INFORMATION:
<221> NAME/KEY: misc_feature
<222> LOCATION: (20)..()
<223> OTHER INFORMATION: Urokinase-type plasminogen activator (uPA)

<400> SEQUENCE: 1

Met Arg Ala Leu Leu Ala Arg Leu Leu Leu Cys Val Leu Val Val Ser
-20                 -15                 -10                  -5

Asp Ser Lys Gly Ser Asn Glu Leu His Gln Val Pro Ser Asn Cys Asp
            -1  1                   5                      10

Cys Leu Asn Gly Gly Thr Cys Val Ser Asn Lys Tyr Phe Ser Asn Ile
             15                  20                  25

His Trp Cys Asn Cys Pro Lys Lys Phe Gly Gln His Cys Glu Ile
         30                  35                  40

Asp Lys Ser Lys Thr Cys Tyr Glu Gly Asn Gly His Phe Tyr Arg Gly
 45                  50                  55                  60

Lys Ala Ser Thr Asp Thr Met Gly Arg Pro Cys Leu Pro Trp Asn Ser
                 65                  70                  75

Ala Thr Val Leu Gln Gln Thr Tyr His Ala His Arg Ser Asp Ala Leu
             80                  85                  90
```

```
Gln Leu Gly Leu Gly Lys His Asn Tyr Cys Arg Asn Pro Asp Asn Arg
             95                 100                 105

Arg Arg Pro Trp Cys Tyr Val Gln Val Gly Leu Lys Pro Leu Val Gln
        110                 115                 120

Glu Cys Met Val His Asp Cys Ala Asp Gly Lys Lys Pro Ser Ser Pro
125                 130                 135                 140

Pro Glu Glu Leu Lys Phe Gln Cys Gly Gln Lys Thr Leu Arg Pro Arg
                145                 150                 155

Phe Lys Ile Ile Gly Gly Glu Phe Thr Thr Ile Glu Asn Gln Pro Trp
            160                 165                 170

Phe Ala Ala Ile Tyr Arg Arg His Arg Gly Gly Ser Val Thr Tyr Val
        175                 180                 185

Cys Gly Gly Ser Leu Ile Ser Pro Cys Trp Val Ile Ser Ala Thr His
190                 195                 200

Cys Phe Ile Asp Tyr Pro Lys Lys Glu Asp Tyr Ile Val Tyr Leu Gly
205                 210                 215                 220

Arg Ser Arg Leu Asn Ser Asn Thr Gln Gly Glu Met Lys Phe Glu Val
                225                 230                 235

Glu Asn Leu Ile Leu His Lys Asp Tyr Ser Ala Asp Thr Leu Ala His
            240                 245                 250

His Asn Asp Ile Ala Leu Leu Lys Ile Arg Ser Lys Glu Gly Arg Cys
        255                 260                 265

Ala Gln Pro Ser Arg Thr Ile Gln Thr Ile Cys Leu Pro Ser Met Tyr
    270                 275                 280

Asn Asp Pro Gln Phe Gly Thr Ser Cys Glu Ile Thr Gly Phe Gly Lys
285                 290                 295                 300

Glu Asn Ser Thr Asp Tyr Leu Tyr Pro Glu Gln Leu Lys Met Thr Val
                305                 310                 315

Val Lys Leu Ile Ser His Arg Glu Cys Gln Gln Pro His Tyr Tyr Gly
            320                 325                 330

Ser Glu Val Thr Thr Lys Met Leu Cys Ala Ala Asp Pro Gln Trp Lys
        335                 340                 345

Thr Asp Ser Cys Gln Gly Asp Ser Gly Gly Pro Leu Val Cys Ser Leu
350                 355                 360

Gln Gly Arg Met Thr Leu Thr Gly Ile Val Ser Trp Gly Arg Gly Cys
365                 370                 375                 380

Ala Leu Lys Asp Lys Pro Gly Val Tyr Thr Arg Val Ser His Phe Leu
                385                 390                 395

Pro Trp Ile Arg Ser His Thr Lys Glu Glu Asn Gly Leu Ala Leu
            400                 405                 410

<210> SEQ ID NO 2
<211> LENGTH: 143
<212> TYPE: PRT
<213> ORGANISM: Homo sapiens
<220> FEATURE:
<221> NAME/KEY: misc_feature
<223> OTHER INFORMATION: Urinary trypsin inhibitor (UTI)

<400> SEQUENCE: 2

Ala Val Leu Pro Gln Glu Glu Gly Ser Gly Gly Gly Gln Leu Val
1               5                  10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
```

```
                  35                  40                  45
Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
            115                 120                 125

Arg Glu Tyr Cys Gly Val Pro Gly Asp Gly Asp Glu Glu Leu Leu
        130                 135                 140

<210> SEQ ID NO 3
<211> LENGTH: 26
<212> TYPE: DNA
<213> ORGANISM: Artificial Sequence
<220> FEATURE:
<223> OTHER INFORMATION: Pr-1 primer

<400> SEQUENCE: 3
cgtgagcgac tccaaaggca gcaatg                                        26

<210> SEQ ID NO 4
<211> LENGTH: 28
<212> TYPE: DNA
<213> ORGANISM: Artificial Sequence
<220> FEATURE:
<223> OTHER INFORMATION: Pr-2 primer

<400> SEQUENCE: 4
aaaccagggc tggttctcga tggtggtg                                      28

<210> SEQ ID NO 5
<211> LENGTH: 64
<212> TYPE: DNA
<213> ORGANISM: Artificial Sequence
<220> FEATURE:
<223> OTHER INFORMATION: portion of gene encoding E. coli OmpA protein
      (coding strand)

<400> SEQUENCE: 5
catgaaaaaa accgctatcg ctatcgctgt tgctctggct ggttttgcta ccgttgctca   60
ggcc                                                                64

<210> SEQ ID NO 6
<211> LENGTH: 60
<212> TYPE: DNA
<213> ORGANISM: Artificial Sequence
<220> FEATURE:
<223> OTHER INFORMATION: portion of gene encoding E. coli OmpA protein
      (non-coding strand)

<400> SEQUENCE: 6
ggcctgagca acggtagcaa aaccagccag agcaacagcg atagcgatag cggttttttt   60

<210> SEQ ID NO 7
<211> LENGTH: 25
<212> TYPE: DNA
<213> ORGANISM: Artificial Sequence
<220> FEATURE:
<223> OTHER INFORMATION: Pr-3 primer
```

```
<400> SEQUENCE: 7
gggtaccatc tgcgcagtca tgcac                                             25

<210> SEQ ID NO 8
<211> LENGTH: 39
<212> TYPE: DNA
<213> ORGANISM: Artificial Sequence
<220> FEATURE:
<223> OTHER INFORMATION: coding strand of synthetic BamHI-TaqI DNA
      adaptor

<400> SEQUENCE: 8
gatccaatca aatgagtaat gaactacatc aagtaccat                              39

<210> SEQ ID NO 9
<211> LENGTH: 37
<212> TYPE: DNA
<213> ORGANISM: Artificial Sequence
<220> FEATURE:
<223> OTHER INFORMATION: non-coding strand of synthetic BamHI-TaqI DNA
      adaptor

<400> SEQUENCE: 9
cgatggtact tgatgtagtt cattactcat ttgattg                                37

<210> SEQ ID NO 10
<211> LENGTH: 36
<212> TYPE: DNA
<213> ORGANISM: Artificial Sequence
<220> FEATURE:
<223> OTHER INFORMATION: Pr-4 primer

<400> SEQUENCE: 10
gggtaccgtt gctgcttgca acctgccgat tgtccg                                 36

<210> SEQ ID NO 11
<211> LENGTH: 32
<212> TYPE: DNA
<213> ORGANISM: Artificial Sequence
<220> FEATURE:
<223> OTHER INFORMATION: Pr-5 primer

<400> SEQUENCE: 11
gtgatcaacc cggaacaccg caatattcac gg                                     32

<210> SEQ ID NO 12
<211> LENGTH: 51
<212> TYPE: DNA
<213> ORGANISM: Artificial Sequence
<220> FEATURE:
<223> OTHER INFORMATION: coding strand of BsmI-XbaI HI-8 UTI adaptor

<400> SEQUENCE: 12
gtgaatattg cggtgttccg ggtgatggtg atgaagaact gctgtgatcc t                51

<210> SEQ ID NO 13
<211> LENGTH: 57
<212> TYPE: DNA
<213> ORGANISM: Artificial Sequence
<220> FEATURE:
<223> OTHER INFORMATION: non-coding strand of BsmI-XbaI HI-8 UTI adaptor

<400> SEQUENCE: 13
ctagaggatc acagcagttc ttcatcacca tcacccggaa caccgcaata ttcacgg          57
```

<210> SEQ ID NO 14
<211> LENGTH: 13
<212> TYPE: DNA
<213> ORGANISM: Artificial Sequence
<220> FEATURE:
<223> OTHER INFORMATION: coding strand of ApoI-KpnI adaptor

<400> SEQUENCE: 14
aatttcaggg tat                                                          13

<210> SEQ ID NO 15
<211> LENGTH: 5
<212> TYPE: DNA
<213> ORGANISM: Artificial Sequence
<220> FEATURE:
<223> OTHER INFORMATION: non-coding strand of ApoI-KpnI adaptor

<400> SEQUENCE: 15 cctga                                                                    5

<210> SEQ ID NO 16
<211> LENGTH: 253
<212> TYPE: DNA
<213> ORGANISM: Homo sapiens
<220> FEATURE:
<221> NAME/KEY: misc_feature
<223> OTHER INFORMATION: coding strand of HI-8 UTI DNA fragment

<400> SEQUENCE: 16
ggttgctgct tgcaacctgc cggttatccg tggtccgtgc cgtgctttca tccagctgtg        60
ggctttcgac gctgttaaag gtaaatgcgt tctgttcccg tatggtggtt gccagggtaa       120
cggtaacaaa ttctattctg aaaaagaatg ccgtgaatat tgcggtgttc cgggtgacga       180
agacgaagaa ctgctgtgat gatctagagc ccagcccgcc taatgagcgg gcttttttttt     240 gaacaaaagg cgg                                                         253

<210> SEQ ID NO 17
<211> LENGTH: 261
<212> TYPE: DNA
<213> ORGANISM: Homo sapiens
<220> FEATURE:
<221> NAME/KEY: misc_feature
<223> OTHER INFORMATION: non-coding strand of HI-8 UTI DNA fragment

<400> SEQUENCE: 17
aattccgcct tttgttcaaa aaaaagcccg ctcattaggc gggctgggct ctagatcatc        60
acagcagttc ttcgtcttcg tcacccggaa caccgcaata ttcacggcat tcttttttcag     120 aatagaattt gttaccgtta ccctggcaac caccatacgg gaacagaacg catttacctt      180
taacagcgtc gaaagcccac agctggatga agcacggca cggaccacgg ataaccggca       240
ggttgcaagc agcaaccgta c                                                261

<210> SEQ ID NO 18
<211> LENGTH: 32
<212> TYPE: PRT
<213> ORGANISM: Homo sapiens
<220> FEATURE:
<221> NAME/KEY: misc_feature
<223> OTHER INFORMATION: residues 11-42 of ATF domain of uPA (formula I)

<400> SEQUENCE: 18

Cys Asp Cys Leu Asn Gly Gly Thr Cys Val Ser Asn Lys Tyr Phe Ser
1               5                   10                  15

```
Asn Ile His Trp Cys Asn Cys Pro Lys Lys Phe Gly Gly Gln His Cys
            20                  25                  30
```

<210> SEQ ID NO 19
<211> LENGTH: 51
<212> TYPE: PRT
<213> ORGANISM: Homo sapiens
<220> FEATURE:
<221> NAME/KEY: misc_feature
<223> OTHER INFORMATION: residues 5-55 of HI-8 domain of UTI
      (formula II)

<400> SEQUENCE: 19

```
Cys Asn Leu Pro Ile Val Arg Gly Pro Cys Arg Ala Phe Ile Gln Leu
1               5                   10                  15

Trp Ala Phe Asp Ala Val Lys Gly Lys Cys Val Leu Phe Pro Tyr Gly
            20                  25                  30

Gly Cys Gln Gly Asn Gly Asn Lys Phe Tyr Ser Glu Lys Glu Cys Arg
            35                  40                  45

Glu Tyr Cys
    50
```

<210> SEQ ID NO 20
<211> LENGTH: 10
<212> TYPE: PRT
<213> ORGANISM: Homo sapiens
<220> FEATURE:
<221> NAME/KEY: misc_feature
<223> OTHER INFORMATION: residues 1-10 of the ATF domain of uPA

<400> SEQUENCE: 20

```
Ser Asn Glu Leu His Gln Val Pro Ser Asn
1               5                   10
```

<210> SEQ ID NO 21
<211> LENGTH: 9
<212> TYPE: PRT
<213> ORGANISM: Homo sapiens
<220> FEATURE:
<221> NAME/KEY: misc_feature
<223> OTHER INFORMATION: residues 2-10 of the ATF domain of uPA

<400> SEQUENCE: 21

```
Asn Glu Leu His Gln Val Pro Ser Asn
1               5
```

<210> SEQ ID NO 22
<211> LENGTH: 8
<212> TYPE: PRT
<213> ORGANISM: Homo sapiens
<220> FEATURE:
<221> NAME/KEY: misc_feature
<223> OTHER INFORMATION: residues 3-10 of the ATF domain of uPA

<400> SEQUENCE: 22

```
Glu Leu His Gln Val Pro Ser Asn
1               5
```

<210> SEQ ID NO 23
<211> LENGTH: 7
<212> TYPE: PRT
<213> ORGANISM: Homo sapiens
<220> FEATURE:
<221> NAME/KEY: misc_feature
<223> OTHER INFORMATION: residues 4-10 of the ATF domain of uPA

```
<400> SEQUENCE: 23

Leu His Gln Val Pro Ser Asn
1               5

<210> SEQ ID NO 24
<211> LENGTH: 6
<212> TYPE: PRT
<213> ORGANISM: Homo sapiens
<220> FEATURE:
<221> NAME/KEY: misc_feature
<223> OTHER INFORMATION: residues 5-10 of the ATF domain of uPA

<400> SEQUENCE: 24

His Gln Val Pro Ser Asn
1               5

<210> SEQ ID NO 25
<211> LENGTH: 5
<212> TYPE: PRT
<213> ORGANISM: Homo sapiens
<220> FEATURE:
<221> NAME/KEY: misc_feature
<223> OTHER INFORMATION: residues 6-10 of the ATF domain of uPA

<400> SEQUENCE: 25

Gln Val Pro Ser Asn
1               5

<210> SEQ ID NO 26
<211> LENGTH: 4
<212> TYPE: PRT
<213> ORGANISM: Homo sapiens
<220> FEATURE:
<221> NAME/KEY: misc_feature
<223> OTHER INFORMATION: residues 7-10 of the ATF domain of uPA

<400> SEQUENCE: 26

Val Pro Ser Asn
1

<210> SEQ ID NO 27
<211> LENGTH: 7
<212> TYPE: PRT
<213> ORGANISM: Artificial Sequence
<220> FEATURE:
<223> OTHER INFORMATION: intervening sequence between formula 1 and
      formula 2

<400> SEQUENCE: 27

Ala Asp Gly Thr Val Ala Ala
1               5

<210> SEQ ID NO 28
<211> LENGTH: 6
<212> TYPE: PRT
<213> ORGANISM: Artificial Sequence
<220> FEATURE:
<223> OTHER INFORMATION: intervening sequence between formula 1 and
      formula 2

<400> SEQUENCE: 28

Ala Asp Gly Val Ala Ala
1               5

<210> SEQ ID NO 29
<211> LENGTH: 5
<212> TYPE: PRT
```

```
<213> ORGANISM: Artificial Sequence
<220> FEATURE:
<223> OTHER INFORMATION: intervening sequence between formula 1 and
      formula 2

<400> SEQUENCE: 29

Ala Asp Gly Ala Ala
1               5

<210> SEQ ID NO 30
<211> LENGTH: 4
<212> TYPE: PRT
<213> ORGANISM: Artificial Sequence
<220> FEATURE:
<223> OTHER INFORMATION: intervening sequence between formula 1 and
      formula 2
<221> NAME/KEY: misc_feature
<222> LOCATION: (4)..(4)
<223> OTHER INFORMATION: "Xaa" may be any amino acid

<400> SEQUENCE: 30

Ala Asp Gly Xaa
1

<210> SEQ ID NO 31
<211> LENGTH: 6
<212> TYPE: PRT
<213> ORGANISM: Artificial Sequence
<220> FEATURE:
<223> OTHER INFORMATION: intervening sequence between formula 1 and
      formula 2

<400> SEQUENCE: 31

Ala Asp Thr Val Ala Ala
1               5

<210> SEQ ID NO 32
<211> LENGTH: 5
<212> TYPE: PRT
<213> ORGANISM: Artificial Sequence
<220> FEATURE:
<223> OTHER INFORMATION: intervening sequence between formula 1 and
      formula 2

<400> SEQUENCE: 32

Ala Asp Val Ala Ala
1               5

<210> SEQ ID NO 33
<211> LENGTH: 4
<212> TYPE: PRT
<213> ORGANISM: Artificial Sequence
<220> FEATURE:
<223> OTHER INFORMATION: intervening sequence between formula 1 and
      formula 2

<400> SEQUENCE: 33

Ala Asp Ala Ala
1

<210> SEQ ID NO 34
<211> LENGTH: 5
<212> TYPE: PRT
<213> ORGANISM: Artificial Sequence
<220> FEATURE:
<223> OTHER INFORMATION: intervening sequence between formula 1 and
      formula 2

<400> SEQUENCE: 34
```

```
Ala Thr Val Ala Ala
1               5

<210> SEQ ID NO 35
<211> LENGTH: 4
<212> TYPE: PRT
<213> ORGANISM: Artificial Sequence
<220> FEATURE:
<223> OTHER INFORMATION: intervening sequence between formula 1 and
      formula 2

<400> SEQUENCE: 35

Ala Val Ala Ala
1

<210> SEQ ID NO 36
<211> LENGTH: 5
<212> TYPE: PRT
<213> ORGANISM: Artificial Sequence
<220> FEATURE:
<223> OTHER INFORMATION: intervening sequence between formula 1 and
      formula 2
<221> NAME/KEY: misc_feature
<222> LOCATION: (1)..(1)
<223> OTHER INFORMATION: "Xaa" may be any amino acid

<400> SEQUENCE: 36

Xaa Thr Val Ala Ala
1               5

<210> SEQ ID NO 37
<211> LENGTH: 4
<212> TYPE: PRT
<213> ORGANISM: Artificial Sequence
<220> FEATURE:
<223> OTHER INFORMATION: intervening sequence between formula 1 and
      formula 2
<221> NAME/KEY: misc_feature
<222> LOCATION: (1)..(1)
<223> OTHER INFORMATION: "Xaa" may be any amino acid

<400> SEQUENCE: 37

Xaa Val Ala Ala
1

<210> SEQ ID NO 38
<211> LENGTH: 21
<212> TYPE: PRT
<213> ORGANISM: Artificial Sequence
<220> FEATURE:
<223> OTHER INFORMATION: intervening sequence between formula 1 and
      formula 2

<400> SEQUENCE: 38

Ala Asp Gly Lys Lys Pro Ser Ser Pro Pro Glu Glu Leu Lys Phe Gln
1               5                   10                  15

Gly Thr Val Ala Ala
            20

<210> SEQ ID NO 39
<211> LENGTH: 11
<212> TYPE: PRT
<213> ORGANISM: Artificial Sequence
<220> FEATURE:
<223> OTHER INFORMATION: intervening sequence between formula 1 and
      formula 2

<400> SEQUENCE: 39
```

```
Glu Ile Asp Lys Ser Lys Thr Thr Val Ala Ala
1               5                   10
```

<210> SEQ ID NO 40
<211> LENGTH: 10
<212> TYPE: PRT
<213> ORGANISM: Artificial Sequence
<220> FEATURE:
<223> OTHER INFORMATION: intervening sequence between formula 1 and
      formula 2

<400> SEQUENCE: 40

```
Glu Ile Asp Lys Ser Lys Thr Val Ala Ala
1               5                   10
```

<210> SEQ ID NO 41
<211> LENGTH: 9
<212> TYPE: PRT
<213> ORGANISM: Artificial Sequence
<220> FEATURE:
<223> OTHER INFORMATION: intervening sequence between formula 1 and
      formula 2

<400> SEQUENCE: 41

```
Glu Ile Asp Lys Ser Lys Thr Ala Ala
1               5
```

<210> SEQ ID NO 42
<211> LENGTH: 8
<212> TYPE: PRT
<213> ORGANISM: Artificial Sequence
<220> FEATURE:
<223> OTHER INFORMATION: intervening sequence between formula 1 and
      formula 2
<221> NAME/KEY: misc_feature
<222> LOCATION: (8)..(8)
<223> OTHER INFORMATION: "Xaa" may be any amino acid

<400> SEQUENCE: 42

```
Glu Ile Asp Lys Ser Lys Thr Xaa
1               5
```

<210> SEQ ID NO 43
<211> LENGTH: 7
<212> TYPE: PRT
<213> ORGANISM: Artificial Sequence
<220> FEATURE:
<223> OTHER INFORMATION: intervening sequence between formula 1 and
      formula 2
<221> NAME/KEY: misc_feature
<222> LOCATION: (7)..(7)
<223> OTHER INFORMATION: "Xaa" may be any amino acid

<400> SEQUENCE: 43

```
Glu Ile Asp Lys Ser Lys Xaa
1               5
```

<210> SEQ ID NO 44
<211> LENGTH: 9
<212> TYPE: PRT
<213> ORGANISM: Artificial Sequence
<220> FEATURE:
<223> OTHER INFORMATION: intervening sequence between formula 1 and
      formula 2

<400> SEQUENCE: 44

```
Glu Ile Asp Lys Ser Lys Val Ala Ala
1               5
```

```
<210> SEQ ID NO 45
<211> LENGTH: 8
<212> TYPE: PRT
<213> ORGANISM: Artificial Sequence
<220> FEATURE:
<223> OTHER INFORMATION: intervening sequence between formula 1 and
      formula 2

<400> SEQUENCE: 45

Glu Ile Asp Lys Ser Lys Ala Ala
1               5

<210> SEQ ID NO 46
<211> LENGTH: 9
<212> TYPE: PRT
<213> ORGANISM: Artificial Sequence
<220> FEATURE:
<223> OTHER INFORMATION: intervening sequence between formula 1 and
      formula 2

<400> SEQUENCE: 46

Glu Ile Asp Lys Ser Thr Val Ala Ala
1               5

<210> SEQ ID NO 47
<211> LENGTH: 8
<212> TYPE: PRT
<213> ORGANISM: Artificial Sequence
<220> FEATURE:
<223> OTHER INFORMATION: intervening sequence between formula 1 and
      formula 2

<400> SEQUENCE: 47

Glu Ile Asp Lys Ser Val Ala Ala
1               5

<210> SEQ ID NO 48
<211> LENGTH: 7
<212> TYPE: PRT
<213> ORGANISM: Artificial Sequence
<220> FEATURE:
<223> OTHER INFORMATION: intervening sequence between formula 1 and
      formula 2

<400> SEQUENCE: 48

Glu Ile Asp Lys Ser Ala Ala
1               5

<210> SEQ ID NO 49
<211> LENGTH: 6
<212> TYPE: PRT
<213> ORGANISM: Artificial Sequence
<220> FEATURE:
<223> OTHER INFORMATION: intervening sequence between formula 1 and
      formula 2
<221> NAME/KEY: misc_feature
<223> OTHER INFORMATION: "Xaa" may be any amino acid
<221> NAME/KEY: misc_feature
<222> LOCATION: (6)..(6)
<223> OTHER INFORMATION: "Xaa" may be any amino acid

<400> SEQUENCE: 49

Glu Ile Asp Lys Ser Xaa
1               5

<210> SEQ ID NO 50
<211> LENGTH: 8
```

```
<212> TYPE: PRT
<213> ORGANISM: Artificial Sequence
<220> FEATURE:
<223> OTHER INFORMATION: intervening sequence between formula 1 and
      formula 2

<400> SEQUENCE: 50

Glu Ile Asp Lys Thr Val Ala Ala
1               5

<210> SEQ ID NO 51
<211> LENGTH: 7
<212> TYPE: PRT
<213> ORGANISM: Artificial Sequence
<220> FEATURE:
<223> OTHER INFORMATION: intervening sequence between formula 1 and
      formula 2

<400> SEQUENCE: 51

Glu Ile Asp Lys Val Ala Ala
1               5

<210> SEQ ID NO 52
<211> LENGTH: 6
<212> TYPE: PRT
<213> ORGANISM: Artificial Sequence
<220> FEATURE:
<223> OTHER INFORMATION: intervening sequence between formula 1 and
      formula 2

<400> SEQUENCE: 52

Glu Ile Asp Lys Ala Ala
1               5

<210> SEQ ID NO 53
<211> LENGTH: 5
<212> TYPE: PRT
<213> ORGANISM: Artificial Sequence
<220> FEATURE:
<223> OTHER INFORMATION: intervening sequence between formula 1 and
      formula 2
<221> NAME/KEY: misc_feature
<222> LOCATION: (5)..(5)
<223> OTHER INFORMATION: "Xaa" may be any amino acid

<400> SEQUENCE: 53

Glu Ile Asp Lys Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: intervening sequence between formula 1 and
      formula 2

<400> SEQUENCE: 54

Glu Ile Asp Thr Val Ala Ala
1               5

<210> SEQ ID NO 55
<211> LENGTH: 6
<212> TYPE: PRT
<213> ORGANISM: Artificial Sequence
<220> FEATURE:
<223> OTHER INFORMATION: intervening sequence between formula 1 and
      formula 2
```

```
<400> SEQUENCE: 55

Glu Ile Asp Val Ala Ala
1               5

<210> SEQ ID NO 56
<211> LENGTH: 5
<212> TYPE: PRT
<213> ORGANISM: Artificial Sequence
<220> FEATURE:
<223> OTHER INFORMATION: intervening sequence between formula 1 and
      formula 2

<400> SEQUENCE: 56

Glu Ile Asp Ala Ala
1               5

<210> SEQ ID NO 57
<211> LENGTH: 4
<212> TYPE: PRT
<213> ORGANISM: Artificial Sequence
<220> FEATURE:
<223> OTHER INFORMATION: intervening sequence between formula 1 and
      formula 2
<221> NAME/KEY: misc_feature
<222> LOCATION: (4)..(4)
<223> OTHER INFORMATION: "Xaa" may be any amino acid

<400> SEQUENCE: 57

Glu Ile Asp Xaa
1

<210> SEQ ID NO 58
<211> LENGTH: 6
<212> TYPE: PRT
<213> ORGANISM: Artificial Sequence
<220> FEATURE:
<223> OTHER INFORMATION: intervening sequence between formula 1 and
      formula 2

<400> SEQUENCE: 58

Glu Ile Thr Val Ala Ala
1               5

<210> SEQ ID NO 59
<211> LENGTH: 4
<212> TYPE: PRT
<213> ORGANISM: Artificial Sequence
<220> FEATURE:
<223> OTHER INFORMATION: intervening sequence between formula 1 and
      formula 2

<400> SEQUENCE: 59

Glu Ile Ala Ala
1

<210> SEQ ID NO 60
<211> LENGTH: 5
<212> TYPE: PRT
<213> ORGANISM: Artificial Sequence
<220> FEATURE:
<223> OTHER INFORMATION: intervening sequence between formula 1 and
      formula 2

<400> SEQUENCE: 60

Glu Thr Val Ala Ala
1               5
```

```
<210> SEQ ID NO 61
<211> LENGTH: 4
<212> TYPE: PRT
<213> ORGANISM: Artificial Sequence
<220> FEATURE:
<223> OTHER INFORMATION: intervening sequence between formula 1 and
      formula 2

<400> SEQUENCE: 61

Glu Val Ala Ala
1

<210> SEQ ID NO 62
<211> LENGTH: 89
<212> TYPE: PRT
<213> ORGANISM: Homo sapiens
<220> FEATURE:
<221> NAME/KEY: misc_feature
<223> OTHER INFORMATION: residues 43-131 of the ATF domain of uPA

<400> SEQUENCE: 62

Glu Ile Asp Lys Ser Lys Thr Cys Tyr Glu Gly Asn Gly His Phe Tyr
1               5                   10                  15

Arg Gly Lys Ala Ser Thr Asp Thr Met Gly Arg Pro Cys Leu Pro Trp
            20                  25                  30

Asn Ser Ala Thr Val Leu Gln Gln Thr Tyr His Ala His Arg Ser Asp
        35                  40                  45

Ala Leu Gln Leu Gly Leu Gly Lys His Asn Tyr Cys Arg Asn Pro Asp
    50                  55                  60

Asn Arg Arg Arg Pro Trp Cys Tyr Val Gln Val Gly Leu Lys Pro Leu
65                  70                  75                  80

Val Gln Glu Cys Met Val His Asp Cys
                85

<210> SEQ ID NO 63
<211> LENGTH: 5
<212> TYPE: PRT
<213> ORGANISM: Artificial Sequence
<220> FEATURE:
<223> OTHER INFORMATION: intervening sequence between formula 1 and
      formula 2

<400> SEQUENCE: 63

Glu Ile Val Ala Ala
1               5

<210> SEQ ID NO 64
<211> LENGTH: 11
<212> TYPE: PRT
<213> ORGANISM: Homo sapiens
<220> FEATURE:
<221> NAME/KEY: misc_feature
<223> OTHER INFORMATION: residues 56-66 of the HI-8 domain of UTI

<400> SEQUENCE: 64

Gly Val Pro Gly Asp Gly Asp Glu Glu Leu Leu
1               5                   10

<210> SEQ ID NO 65
<211> LENGTH: 10
<212> TYPE: PRT
<213> ORGANISM: Homo sapiens
<220> FEATURE:
<221> NAME/KEY: misc_feature
<223> OTHER INFORMATION: residues 56-65 of the HI-8 domain of UTI
```

```
<400> SEQUENCE: 65

Gly Val Pro Gly Asp Gly Asp Glu Glu Leu
1               5                   10

<210> SEQ ID NO 66
<211> LENGTH: 9
<212> TYPE: PRT
<213> ORGANISM: Homo sapiens
<220> FEATURE:
<221> NAME/KEY: misc_feature
<223> OTHER INFORMATION: residues 56-64 of the HI-8 domain of UTI

<400> SEQUENCE: 66

Gly Val Pro Gly Asp Gly Asp Glu Glu
1               5

<210> SEQ ID NO 67
<211> LENGTH: 8
<212> TYPE: PRT
<213> ORGANISM: Homo sapiens
<220> FEATURE:
<221> NAME/KEY: misc_feature
<223> OTHER INFORMATION: residues 56-63 of the HI-8 domain of UTI

<400> SEQUENCE: 67

Gly Val Pro Gly Asp Gly Asp Glu
1               5

<210> SEQ ID NO 68
<211> LENGTH: 7
<212> TYPE: PRT
<213> ORGANISM: Homo sapiens
<220> FEATURE:
<221> NAME/KEY: misc_feature
<223> OTHER INFORMATION: residues 56-62 of the HI-8 domain of UTI

<400> SEQUENCE: 68

Gly Val Pro Gly Asp Gly Asp
1               5

<210> SEQ ID NO 69
<211> LENGTH: 6
<212> TYPE: PRT
<213> ORGANISM: Homo sapiens
<220> FEATURE:
<221> NAME/KEY: misc_feature
<223> OTHER INFORMATION: residues 56-61 of the HI-8 domain of UTI

<400> SEQUENCE: 69

Gly Val Pro Gly Asp Gly
1               5

<210> SEQ ID NO 70
<211> LENGTH: 5
<212> TYPE: PRT
<213> ORGANISM: Homo sapiens
<220> FEATURE:
<221> NAME/KEY: misc_feature
<223> OTHER INFORMATION: residues 56-60 of the HI-8 domain of UTI

<400> SEQUENCE: 70

Gly Val Pro Gly Asp
1               5

<210> SEQ ID NO 71
<211> LENGTH: 4
<212> TYPE: PRT
```

<210> SEQ ID NO 72
<211> LENGTH: 600
<212> TYPE: DNA
<213> ORGANISM: Homo sapiens
<220> FEATURE:
<221> NAME/KEY: misc_feature
<223> OTHER INFORMATION: residues 56-59 of the HI-8 domain of UTI

<400> SEQUENCE: 71

Gly Val Pro Gly
1

<210> SEQ ID NO 72
<211> LENGTH: 600
<212> TYPE: DNA
<213> ORGANISM: Homo sapiens
<220> FEATURE:
<221> NAME/KEY: misc_feature
<223> OTHER INFORMATION: ATF domain of uPA
<221> NAME/KEY: CDS
<222> LOCATION: (1)..(600)
<223> OTHER INFORMATION:
<221> NAME/KEY: mat_peptide
<222> LOCATION: (61)..()
<223> OTHER INFORMATION:

<400> SEQUENCE: 72

| | | | | | | | | | | | | | | | | |
|---|---|---|---|---|---|---|---|---|---|---|---|---|---|---|---|---|
| atg | aga | gcc | ctg | ctg | gcg | cgc | ctg | ctt | ctc | tgc | gtc | ctg | gtc | gtg | agc | 48 |
| Met | Arg | Ala | Leu | Leu | Ala | Arg | Leu | Leu | Leu | Cys | Val | Leu | Val | Val | Ser | |
| -20 | | | | -15 | | | | -10 | | | | | -5 | | | |

| gac | tcc | aaa | ggc | agc | aat | gaa | ctt | cat | caa | gtt | cca | tcg | aac | tgt | gac | 96 |
|---|---|---|---|---|---|---|---|---|---|---|---|---|---|---|---|---|
| Asp | Ser | Lys | Gly | Ser | Asn | Glu | Leu | His | Gln | Val | Pro | Ser | Asn | Cys | Asp | |
| | | | -1 | 1 | | | | 5 | | | | | | 10 | | |

| tgt | cta | aat | gga | gga | aca | tgt | gtg | tcc | aac | aag | tac | ttc | tcc | aac | att | 144 |
|---|---|---|---|---|---|---|---|---|---|---|---|---|---|---|---|---|
| Cys | Leu | Asn | Gly | Gly | Thr | Cys | Val | Ser | Asn | Lys | Tyr | Phe | Ser | Asn | Ile | |
| | | | | 15 | | | | | 20 | | | | | 25 | | |

| cac | tgg | tgc | aac | tgc | cca | aag | aaa | ttc | gga | ggg | cag | cac | tgt | gaa | ata | 192 |
|---|---|---|---|---|---|---|---|---|---|---|---|---|---|---|---|---|
| His | Trp | Cys | Asn | Cys | Pro | Lys | Lys | Phe | Gly | Gly | Gln | His | Cys | Glu | Ile | |
| | 30 | | | | | 35 | | | | | 40 | | | | | |

| gat | aag | tca | aaa | acc | tgc | tat | gag | ggg | aat | ggt | cac | ttt | tac | cga | gga | 240 |
|---|---|---|---|---|---|---|---|---|---|---|---|---|---|---|---|---|
| Asp | Lys | Ser | Lys | Thr | Cys | Tyr | Glu | Gly | Asn | Gly | His | Phe | Tyr | Arg | Gly | |
| 45 | | | | | 50 | | | | | 55 | | | | | 60 | |

| aag | gcc | agc | act | gac | acc | atg | ggc | cgg | ccc | tgc | ctg | ccc | tgg | aac | tct | 288 |
|---|---|---|---|---|---|---|---|---|---|---|---|---|---|---|---|---|
| Lys | Ala | Ser | Thr | Asp | Thr | Met | Gly | Arg | Pro | Cys | Leu | Pro | Trp | Asn | Ser | |
| | | | | 65 | | | | | 70 | | | | | 75 | | |

| gcc | act | gtc | ctt | cag | caa | acg | tac | cat | gcc | cac | aga | tct | gat | gct | ctt | 336 |
|---|---|---|---|---|---|---|---|---|---|---|---|---|---|---|---|---|
| Ala | Thr | Val | Leu | Gln | Gln | Thr | Tyr | His | Ala | His | Arg | Ser | Asp | Ala | Leu | |
| | | | 80 | | | | | 85 | | | | | 90 | | | |

| cag | ctg | ggc | ctg | ggg | aaa | cat | aat | tac | tgc | agg | aac | cca | gac | aac | cgg | 384 |
|---|---|---|---|---|---|---|---|---|---|---|---|---|---|---|---|---|
| Gln | Leu | Gly | Leu | Gly | Lys | His | Asn | Tyr | Cys | Arg | Asn | Pro | Asp | Asn | Arg | |
| | | | 95 | | | | | 100 | | | | | 105 | | | |

| agg | cga | ccc | tgg | tgc | tat | gtg | cag | gtg | ggc | cta | aag | ccg | ctt | gtc | caa | 432 |
|---|---|---|---|---|---|---|---|---|---|---|---|---|---|---|---|---|
| Arg | Arg | Pro | Trp | Cys | Tyr | Val | Gln | Val | Gly | Leu | Lys | Pro | Leu | Val | Gln | |
| 110 | | | | | 115 | | | | | 120 | | | | | | |

| gag | tgc | atg | gtg | cat | gac | tgc | gca | gat | gga | aaa | aag | ccc | tcc | tct | cct | 480 |
|---|---|---|---|---|---|---|---|---|---|---|---|---|---|---|---|---|
| Glu | Cys | Met | Val | His | Asp | Cys | Ala | Asp | Gly | Lys | Lys | Pro | Ser | Ser | Pro | |
| 125 | | | | 130 | | | | | 135 | | | | | 140 | | |

| cca | gaa | gaa | tta | aaa | ttt | cag | tgt | ggc | caa | aag | act | ctg | agg | ccc | cgc | 528 |
|---|---|---|---|---|---|---|---|---|---|---|---|---|---|---|---|---|
| Pro | Glu | Glu | Leu | Lys | Phe | Gln | Cys | Gly | Gln | Lys | Thr | Leu | Arg | Pro | Arg | |
| | | | | 145 | | | | | 150 | | | | | 155 | | |

| ttt | aag | att | att | ggg | gga | gaa | ttc | acc | acc | atc | gag | aac | cag | ccc | tgg | 576 |
|---|---|---|---|---|---|---|---|---|---|---|---|---|---|---|---|---|
| Phe | Lys | Ile | Ile | Gly | Gly | Glu | Phe | Thr | Thr | Ile | Glu | Asn | Gln | Pro | Trp | |
| | | | | 160 | | | | | 165 | | | | | 170 | | |

| ttt | gcg | gcc | atc | tac | agg | agg | cac | | | | | | | | | 600 |
|---|---|---|---|---|---|---|---|---|---|---|---|---|---|---|---|---|
| Phe | Ala | Ala | Ile | Tyr | Arg | Arg | His | | | | | | | | | |
| | | | 175 | | | | 180 | | | | | | | | | |

<210> SEQ ID NO 73
<211> LENGTH: 200
<212> TYPE: PRT
<213> ORGANISM: Homo sapiens
<220> FEATURE:
<221> NAME/KEY: misc_feature
<223> OTHER INFORMATION: ATF domain of uPA

<400> SEQUENCE: 73

```
Met Arg Ala Leu Leu Ala Arg Leu Leu Leu Cys Val Leu Val Val Ser
-20             -15                 -10                 -5

Asp Ser Lys Gly Ser Asn Glu Leu His Gln Val Pro Ser Asn Cys Asp
            -1  1                5                   10

Cys Leu Asn Gly Gly Thr Cys Val Ser Asn Lys Tyr Phe Ser Asn Ile
            15                  20                  25

His Trp Cys Asn Cys Pro Lys Lys Phe Gly Gln His Cys Glu Ile
        30                  35                  40

Asp Lys Ser Lys Thr Cys Tyr Glu Gly Asn Gly His Phe Tyr Arg Gly
45                  50                  55                  60

Lys Ala Ser Thr Asp Thr Met Gly Arg Pro Cys Leu Pro Trp Asn Ser
                65                  70                  75

Ala Thr Val Leu Gln Gln Thr Tyr His Ala His Arg Ser Asp Ala Leu
            80                  85                  90

Gln Leu Gly Leu Gly Lys His Asn Tyr Cys Arg Asn Pro Asp Asn Arg
            95                  100                 105

Arg Arg Pro Trp Cys Tyr Val Gln Val Gly Leu Lys Pro Leu Val Gln
        110                 115                 120

Glu Cys Met Val His Asp Cys Ala Asp Gly Lys Lys Pro Ser Ser Pro
125                 130                 135                 140

Pro Glu Glu Leu Lys Phe Gln Cys Gly Gln Lys Thr Leu Arg Pro Arg
                145                 150                 155

Phe Lys Ile Ile Gly Gly Glu Phe Thr Thr Ile Glu Asn Gln Pro Trp
                160                 165                 170

Phe Ala Ala Ile Tyr Arg Arg His
                175                 180
```

<210> SEQ ID NO 74
<211> LENGTH: 7
<212> TYPE: PRT
<213> ORGANISM: Homo sapiens
<220> FEATURE:
<221> NAME/KEY: misc_feature
<223> OTHER INFORMATION: residues 43-49 of ATF domain of uPA
      (sequence II-1)

<400> SEQUENCE: 74

```
Glu Ile Asp Lys Ser Lys Thr
1               5
```

<210> SEQ ID NO 75
<211> LENGTH: 240
<212> TYPE: DNA
<213> ORGANISM: Homo sapiens
<220> FEATURE:
<221> NAME/KEY: misc_feature
<223> OTHER INFORMATION: HI-8 domain of UTI
<221> NAME/KEY: exon
<222> LOCATION: (1)..(198)
<223> OTHER INFORMATION:

<400> SEQUENCE: 75

```
acg gtt gct gct tgc aac ctg ccg gtt atc cgt ggt ccg tgc cgt gct      48
Thr Val Ala Ala Cys Asn Leu Pro Val Ile Arg Gly Pro Cys Arg Ala
1               5                   10                  15 ttc atc cag ctg tgg gct ttc gac gct gtt aaa ggt aaa tgc gtt ctg      96
Phe Ile Gln Leu Trp Ala Phe Asp Ala Val Lys Gly Lys Cys Val Leu
                20                  25                  30 ttc ccg tat ggt ggt tgc cag ggt aac ggt aac aaa ttc tat tct gaa     144
Phe Pro Tyr Gly Gly Cys Gln Gly Asn Gly Asn Lys Phe Tyr Ser Glu
            35                  40                  45 aaa gaa tgc cgt gaa tat tgc ggt gtt ccg ggt gac gaa gac gaa gaa     192
Lys Glu Cys Arg Glu Tyr Cys Gly Val Pro Gly Asp Glu Asp Glu Glu
        50                  55                  60 ctg ctg tgatgatcta gagcccagcc cgcctaatga gcgggctttt tt             240
Leu Leu
65
```

<210> SEQ ID NO 76
<211> LENGTH: 4
<212> TYPE: PRT
<213> ORGANISM: Homo sapiens
<220> FEATURE:
<221> NAME/KEY: misc_feature
<223> OTHER INFORMATION: residues 1-4 of the HI-8 domain of UTI
      (sequence II-2)

<400> SEQUENCE: 76

Thr Val Ala Ala
1

<210> SEQ ID NO 77
<211> LENGTH: 9
<212> TYPE: PRT
<213> ORGANISM: Homo sapiens
<220> FEATURE:
<221> NAME/KEY: misc_feature
<223> OTHER INFORMATION: residues 135-143 of the ATF domain of uPA

<400> SEQUENCE: 77

Lys Lys Pro Ser Ser Pro Pro Glu Glu
1               5

<210> SEQ ID NO 78
<211> LENGTH: 14
<212> TYPE: PRT
<213> ORGANISM: Artificial Sequence
<220> FEATURE:
<223> OTHER INFORMATION: residues 1-14 of ATFHI

<400> SEQUENCE: 78

Ser Asn Glu Leu His Gln Val Pro Ser Asn Cys Asp Cys Leu
1               5                   10

<210> SEQ ID NO 79
<211> LENGTH: 624
<212> TYPE: DNA
<213> ORGANISM: Artificial Sequence
<220> FEATURE:
<223> OTHER INFORMATION: ATFHI chimeric protein
<221> NAME/KEY: CDS
<222> LOCATION: (12)..(593)
<223> OTHER INFORMATION:
<221> NAME/KEY: mat_peptide
<222> LOCATION: (15)..()
<223> OTHER INFORMATION:

<400> SEQUENCE: 79
gatccaatca a atg agt aat gaa cta cat caa gta cca tcg aac tgt gac    50

```
            Met Ser Asn Glu Leu His Gln Val Pro Ser Asn Cys Asp
             -1  1               5                  10 tgt cta aat gga gga aca tgt gtg tcc aac aag tac ttc tcc aac att        98
Cys Leu Asn Gly Gly Thr Cys Val Ser Asn Lys Tyr Phe Ser Asn Ile
         15                  20                  25 cac tgg tgc aac tgc cca aag aaa ttc gga ggg cag cac tgt gaa ata        146
His Trp Cys Asn Cys Pro Lys Lys Phe Gly Gly Gln His Cys Glu Ile
     30                  35                  40 gat aag tca aaa acc tgc tat gag ggg aat ggt cac ttt tac cga gga        194
Asp Lys Ser Lys Thr Cys Tyr Glu Gly Asn Gly His Phe Tyr Arg Gly
45                  50                  55                  60 aag gcc agc act gac acc atg ggc cgg ccc tgc ctg ccc tgg aac tct        242
Lys Ala Ser Thr Asp Thr Met Gly Arg Pro Cys Leu Pro Trp Asn Ser
                 65                  70                  75 gcc act gtc ctt cag caa acg tac cat gcc cac aga tct gat gct ctt        290
Ala Thr Val Leu Gln Gln Thr Tyr His Ala His Arg Ser Asp Ala Leu
             80                  85                  90 cag ctg ggc ctg ggg aaa cat aat tac tgc agg aac cca gac aac cgg        338
Gln Leu Gly Leu Gly Lys His Asn Tyr Cys Arg Asn Pro Asp Asn Arg
         95                  100                 105 agg cga ccc tgg tgc tat gtg cag gtg ggc cta aag ccg ctt gtc caa        386
Arg Arg Pro Trp Cys Tyr Val Gln Val Gly Leu Lys Pro Leu Val Gln
     110                 115                 120 gag tgc atg gtg cat gac tgc gca gat ggt acc gtt gct gct tgc aac        434
Glu Cys Met Val His Asp Cys Ala Asp Gly Thr Val Ala Ala Cys Asn
125                 130                 135                 140 ctg ccg att gtc cgt ggt ccg tgc cgt gct ttc atc cag ctg tgg gct        482
Leu Pro Ile Val Arg Gly Pro Cys Arg Ala Phe Ile Gln Leu Trp Ala
                 145                 150                 155 ttc gac gct gtt aaa ggt aaa tgc gtt ctg ttc ccg tat ggt ggt tgc        530
Phe Asp Ala Val Lys Gly Lys Cys Val Leu Phe Pro Tyr Gly Gly Cys
             160                 165                 170 cag ggt aac ggt aac aaa ttc tat tct gaa aaa gaa tgc cgt gaa tat        578
Gln Gly Asn Gly Asn Lys Phe Tyr Ser Glu Lys Glu Cys Arg Glu Tyr
         175                 180                 185 tgc ggt gtt ccg ggt tgatcctcta gagtcgacct gcaggcatgc a                 624
Cys Gly Val Pro Gly
    190
```

<210> SEQ ID NO 80
<211> LENGTH: 194
<212> TYPE: PRT
<213> ORGANISM: Artificial Sequence
<220> FEATURE:
<223> OTHER INFORMATION: ATFHI chimeric protein

<400> SEQUENCE: 80

```
Met Ser Asn Glu Leu His Gln Val Pro Ser Asn Cys Asp Cys Leu Asn
 -1  1               5                  10                  15

Gly Gly Thr Cys Val Ser Asn Lys Tyr Phe Ser Asn Ile His Trp Cys
                 20                  25                  30

Asn Cys Pro Lys Lys Phe Gly Gly Gln His Cys Glu Ile Asp Lys Ser
             35                  40                  45

Lys Thr Cys Tyr Glu Gly Asn Gly His Phe Tyr Arg Gly Lys Ala Ser
         50                  55                  60

Thr Asp Thr Met Gly Arg Pro Cys Leu Pro Trp Asn Ser Ala Thr Val
     65                  70                  75

Leu Gln Gln Thr Tyr His Ala His Arg Ser Asp Ala Leu Gln Leu Gly
80                  85                  90                  95
```

```
Leu Gly Lys His Asn Tyr Cys Arg Asn Pro Asp Asn Arg Arg Pro
                100                 105                 110

Trp Cys Tyr Val Gln Val Gly Leu Lys Pro Leu Val Gln Glu Cys Met
            115                 120                 125

Val His Asp Cys Ala Asp Gly Thr Val Ala Ala Cys Asn Leu Pro Ile
        130                 135                 140

Val Arg Gly Pro Cys Arg Ala Phe Ile Gln Leu Trp Ala Phe Asp Ala
    145                 150                 155

Val Lys Gly Lys Cys Val Leu Phe Pro Tyr Gly Gly Cys Gln Gly Asn
160                 165                 170                 175

Gly Asn Lys Phe Tyr Ser Glu Lys Glu Cys Arg Glu Tyr Cys Gly Val
                180                 185                 190

Pro Gly

<210> SEQ ID NO 81
<211> LENGTH: 11
<212> TYPE: DNA
<213> ORGANISM: Homo sapiens
<220> FEATURE:
<221> NAME/KEY: misc_feature
<223> OTHER INFORMATION: 5' end of TaqI-KpnI ATF uPA DNA fragment
      (coding strand)

<400> SEQUENCE: 81
cgaactgtga c                                                          11

<210> SEQ ID NO 82
<211> LENGTH: 9
<212> TYPE: DNA
<213> ORGANISM: Homo sapiens
<220> FEATURE:
<221> NAME/KEY: misc_feature
<223> OTHER INFORMATION: 3' end of TaqI-KpnI ATF uPA DNA fragment
      (non-coding strand)

<400> SEQUENCE: 82 gtcacagtt                                                              9

<210> SEQ ID NO 83
<211> LENGTH: 23
<212> TYPE: DNA
<213> ORGANISM: Homo sapiens
<220> FEATURE:
<221> NAME/KEY: misc_feature
<223> OTHER INFORMATION: 3' end of TaqI-KpnI ATF uPA DNA fragment
      (coding strand)

<400> SEQUENCE: 83
gtgcatgact gcgcagatgg tac                                             23

<210> SEQ ID NO 84
<211> LENGTH: 19
<212> TYPE: DNA
<213> ORGANISM: Homo sapiens
<220> FEATURE:
<221> NAME/KEY: misc_feature
<223> OTHER INFORMATION: 5' end of TaqI-KpnI ATF uPA DNA fragment
      (non-coding strand)

<400> SEQUENCE: 84
catctgcgca gtcatgcac                                                  19

<210> SEQ ID NO 85
<211> LENGTH: 30
```

```
<212> TYPE: DNA
<213> ORGANISM: Homo sapiens
<220> FEATURE:
<221> NAME/KEY: misc_feature
<223> OTHER INFORMATION: 5' end of KpnI-BclI HI-8 UTI DNA fragment
      (coding strand)

<400> SEQUENCE: 85
cgttgctgct tgcaacctgc cgattgtccg                               30

<210> SEQ ID NO 86
<211> LENGTH: 34
<212> TYPE: DNA
<213> ORGANISM: Homo sapiens
<220> FEATURE:
<221> NAME/KEY: misc_feature
<223> OTHER INFORMATION: 3' end of KpnI-BclI HI-8 UTI DNA fragment
      (non-coding strand)

<400> SEQUENCE: 86
cggacaatcg gcaggttgca agcagcaacg gtac                          34

<210> SEQ ID NO 87
<211> LENGTH: 13
<212> TYPE: DNA
<213> ORGANISM: Homo sapiens
<220> FEATURE:
<221> NAME/KEY: misc_feature
<223> OTHER INFORMATION: 3' end of KpnI-BclI HI-8 UTI DNA fragment
      (coding strand)

<400> SEQUENCE: 87
ggtgttccgg gtt                                                 13

<210> SEQ ID NO 88
<211> LENGTH: 17
<212> TYPE: DNA
<213> ORGANISM: Homo sapiens
<220> FEATURE:
<221> NAME/KEY: misc_feature
<223> OTHER INFORMATION: 5' end of KpnI-BclI HI-8 UTI DNA fragment
      (non-coding strand)

<400> SEQUENCE: 88
gatcaacccg gaacacc                                             17

<210> SEQ ID NO 89
<211> LENGTH: 11
<212> TYPE: DNA
<213> ORGANISM: Homo sapiens
<220> FEATURE:
<221> NAME/KEY: misc_feature
<223> OTHER INFORMATION: 3' end of ATF uPA DNA fragment (coding strand)

<400> SEQUENCE: 89
gcagatggta c                                                   11

<210> SEQ ID NO 90
<211> LENGTH: 7
<212> TYPE: DNA
<213> ORGANISM: Homo sapiens
<220> FEATURE:
<221> NAME/KEY: misc_feature
<223> OTHER INFORMATION: 3' end of ATF uPA DNA fragment
      (non-coding strand)

<400> SEQUENCE: 90 catctgc                                                         7
```

<210> SEQ ID NO 91
<211> LENGTH: 10
<212> TYPE: DNA
<213> ORGANISM: Homo sapiens
<220> FEATURE:
<221> NAME/KEY: misc_feature
<223> OTHER INFORMATION: 5' end of HI-8 UTI DNA fragment (coding strand)

<400> SEQUENCE: 91
cgttgctgct                                                              10

<210> SEQ ID NO 92
<211> LENGTH: 14
<212> TYPE: DNA
<213> ORGANISM: Homo sapiens
<220> FEATURE:
<221> NAME/KEY: misc_feature
<223> OTHER INFORMATION: 5' end of HI-8 UTI DNA fragment
      (non-coding strand)

<400> SEQUENCE: 92
agcagcaacg gtac                                                         14

<210> SEQ ID NO 93
<211> LENGTH: 45
<212> TYPE: DNA
<213> ORGANISM: Artificial Sequence
<220> FEATURE:
<223> OTHER INFORMATION: 3' end of HI-8 UTI DNA fragment with Xba I
      cleavage site (coding strand)

<400> SEQUENCE: 93
aaagaatgcc gtgaatattg cggtgttccg ggttgatcct ctaga                       45

<210> SEQ ID NO 94
<211> LENGTH: 45
<212> TYPE: DNA
<213> ORGANISM: Artificial Sequence
<220> FEATURE:
<223> OTHER INFORMATION: 3' end of HI-8 UTI DNA fragment with Xba I
      cleavage site (non-coding strand)

<400> SEQUENCE: 94
tctagaggat caacccggaa caccgcaata ttcacggcat tcttt                       45

<210> SEQ ID NO 95
<211> LENGTH: 645
<212> TYPE: DNA
<213> ORGANISM: Artificial Sequence
<220> FEATURE:
<223> OTHER INFORMATION: ATFHI-CL chimeric protein
<221> NAME/KEY: CDS
<222> LOCATION: (12)..(614)
<223> OTHER INFORMATION:
<221> NAME/KEY: mat_peptide
<222> LOCATION: (15)..()
<223> OTHER INFORMATION:

<400> SEQUENCE: 95
gatccaatca a atg agt aat gaa cta cat caa gta cca tcg aac tgt gac        50
            Met Ser Asn Glu Leu His Gln Val Pro Ser Asn Cys Asp
             -1  1               5                  10 tgt cta aat gga gga aca tgt gtg tcc aac aag tac ttc tcc aac att         98
Cys Leu Asn Gly Gly Thr Cys Val Ser Asn Lys Tyr Phe Ser Asn Ile
         15                  20                  25 cac tgg tgc aac tgc cca aag aaa ttc gga ggg cag cac tgt gaa ata        146

-continued

```
His Trp Cys Asn Cys Pro Lys Lys Phe Gly Gly Gln His Cys Glu Ile
         30                  35                  40 gat aag tca aaa acc tgc tat gag ggg aat ggt cac ttt tac cga gga          194
Asp Lys Ser Lys Thr Cys Tyr Glu Gly Asn Gly His Phe Tyr Arg Gly
 45                  50                  55                  60 aag gcc agc act gac acc atg ggc cgg ccc tgc ctg ccc tgg aac tct          242
Lys Ala Ser Thr Asp Thr Met Gly Arg Pro Cys Leu Pro Trp Asn Ser
                 65                  70                  75 gcc act gtc ctt cag caa acg tac cat gcc cac aga tct gat gct ctt          290
Ala Thr Val Leu Gln Gln Thr Tyr His Ala His Arg Ser Asp Ala Leu
                     80                  85                  90 cag ctg ggc ctg ggg aaa cat aat tac tgc agg aac cca gac aac cgg          338
Gln Leu Gly Leu Gly Lys His Asn Tyr Cys Arg Asn Pro Asp Asn Arg
             95                 100                 105 agg cga ccc tgg tgc tat gtg cag gtg ggc cta aag ccg ctt gtc caa          386
Arg Arg Pro Trp Cys Tyr Val Gln Val Gly Leu Lys Pro Leu Val Gln
110                 115                 120 gag tgc atg gtg cat gac tgc gca gat ggt acc gtt gct gct tgc aac          434
Glu Cys Met Val His Asp Cys Ala Asp Gly Thr Val Ala Ala Cys Asn
125                 130                 135                 140 ctg ccg att gtc cgt ggt ccg tgc cgt gct ttc atc cag ctg tgg gct          482
Leu Pro Ile Val Arg Gly Pro Cys Arg Ala Phe Ile Gln Leu Trp Ala
                145                 150                 155 ttc gac gct gtt aaa ggt aaa tgc gtt ctg ttc ccg tat ggt ggt tgc          530
Phe Asp Ala Val Lys Gly Lys Cys Val Leu Phe Pro Tyr Gly Gly Cys
                    160                 165                 170 cag ggt aac ggt aac aaa ttc tat tct gaa aaa gaa tgc cgt gaa tat          578
Gln Gly Asn Gly Asn Lys Phe Tyr Ser Glu Lys Glu Cys Arg Glu Tyr
                175                 180                 185 tgc ggt gtt ccg ggt gat ggt gat gaa gaa ctg ctg tgatcctcta              624
Cys Gly Val Pro Gly Asp Gly Asp Glu Glu Leu Leu
190                 195                 200 gagtcgacct gcaggcatgc a                                                  645
```

<210> SEQ ID NO 96
<211> LENGTH: 201
<212> TYPE: PRT
<213> ORGANISM: Artificial Sequence
<220> FEATURE:
<223> OTHER INFORMATION: ATFHI-CL chimeric protein

<400> SEQUENCE: 96

```
Met Ser Asn Glu Leu His Gln Val Pro Ser Asn Cys Asp Cys Leu Asn
 -1   1               5                  10                  15

Gly Gly Thr Cys Val Ser Asn Lys Tyr Phe Ser Asn Ile His Trp Cys
                 20                  25                  30

Asn Cys Pro Lys Lys Phe Gly Gly Gln His Cys Glu Ile Asp Lys Ser
                 35                  40                  45

Lys Thr Cys Tyr Glu Gly Asn Gly His Phe Tyr Arg Gly Lys Ala Ser
         50                  55                  60

Thr Asp Thr Met Gly Arg Pro Cys Leu Pro Trp Asn Ser Ala Thr Val
 65                  70                  75

Leu Gln Gln Thr Tyr His Ala His Arg Ser Asp Ala Leu Gln Leu Gly
 80                  85                  90                  95

Leu Gly Lys His Asn Tyr Cys Arg Asn Pro Asp Asn Arg Arg Pro
                100                 105                 110

Trp Cys Tyr Val Gln Val Gly Leu Lys Pro Leu Val Gln Glu Cys Met
             115                 120                 125
```

```
Val His Asp Cys Ala Asp Gly Thr Val Ala Ala Cys Asn Leu Pro Ile
        130                 135                 140

Val Arg Gly Pro Cys Arg Ala Phe Ile Gln Leu Trp Ala Phe Asp Ala
        145                 150                 155

Val Lys Gly Lys Cys Val Leu Phe Pro Tyr Gly Gly Cys Gln Gly Asn
160                 165                 170                 175

Gly Asn Lys Phe Tyr Ser Glu Lys Glu Cys Arg Glu Tyr Cys Gly Val
                180                 185                 190

Pro Gly Asp Gly Asp Glu Glu Leu Leu
            195                 200

<210> SEQ ID NO 97
<211> LENGTH: 666
<212> TYPE: DNA
<213> ORGANISM: Artificial Sequence
<220> FEATURE:
<223> OTHER INFORMATION: ATFHI-ML chimeric protein
<221> NAME/KEY: CDS
<222> LOCATION: (12)..(635)
<223> OTHER INFORMATION:
<221> NAME/KEY: mat_peptide
<222> LOCATION: (15)..()
<223> OTHER INFORMATION:

<400> SEQUENCE: 97
gatccaatca a atg agt aat gaa cta cat caa gta cca tcg aac tgt gac      50
           Met Ser Asn Glu Leu His Gln Val Pro Ser Asn Cys Asp
            -1  1               5                  10 tgt cta aat gga gga aca tgt gtg tcc aac aag tac ttc tcc aac att      98
Cys Leu Asn Gly Gly Thr Cys Val Ser Asn Lys Tyr Phe Ser Asn Ile
            15                  20                  25 cac tgg tgc aac tgc cca aag aaa ttc gga ggg cag cac tgt gaa ata     146
His Trp Cys Asn Cys Pro Lys Lys Phe Gly Gly Gln His Cys Glu Ile
        30                  35                  40 gat aag tca aaa acc tgc tat gag ggg aat ggt cac ttt tac cga gga     194
Asp Lys Ser Lys Thr Cys Tyr Glu Gly Asn Gly His Phe Tyr Arg Gly
 45                 50                  55                  60 aag gcc agc act gac acc atg ggc cgg ccc tgc ctg ccc tgg aac tct     242
Lys Ala Ser Thr Asp Thr Met Gly Arg Pro Cys Leu Pro Trp Asn Ser
                65                  70                  75 gcc act gtc ctt cag caa acg tac cat gcc cac aga tct gat gct ctt     290
Ala Thr Val Leu Gln Gln Thr Tyr His Ala His Arg Ser Asp Ala Leu
            80                  85                  90 cag ctg ggc ctg ggg aaa cat aat tac tgc agg aac cca gac aac cgg     338
Gln Leu Gly Leu Gly Lys His Asn Tyr Cys Arg Asn Pro Asp Asn Arg
        95                  100                 105 agg cga ccc tgg tgc tat gtg cag gtg ggc cta aag ccg ctt gtc caa     386
Arg Arg Pro Trp Cys Tyr Val Gln Val Gly Leu Lys Pro Leu Val Gln
    110                 115                 120 gag tgc atg gtg cat gac tgc gca gat gga aaa aag ccc tcc tct cct     434
Glu Cys Met Val His Asp Cys Ala Asp Gly Lys Lys Pro Ser Ser Pro
125                 130                 135                 140 cca gaa gaa tta aaa ttt cag ggt acc gtt gct gct tgc aac ctg ccg     482
Pro Glu Glu Leu Lys Phe Gln Gly Thr Val Ala Ala Cys Asn Leu Pro
                145                 150                 155 att gtc cgt ggt ccg tgc cgt gct ttc atc cag ctg tgg gct ttc gac     530
Ile Val Arg Gly Pro Cys Arg Ala Phe Ile Gln Leu Trp Ala Phe Asp
            160                 165                 170 gct gtt aaa ggt aaa tgc gtt ctg ttc ccg tat ggt ggt tgc cag ggt     578
Ala Val Lys Gly Lys Cys Val Leu Phe Pro Tyr Gly Gly Cys Gln Gly
        175                 180                 185
```

```
aac ggt aac aaa ttc tat tct gaa aaa gaa tgc cgt gaa tat tgc ggt      626
Asn Gly Asn Lys Phe Tyr Ser Glu Lys Glu Cys Arg Glu Tyr Cys Gly
    190             195             200 gtt ccg ggt tgatcctcta gagtcgacct gcaggcatgc a                        666
Val Pro Gly
205
```

<210> SEQ ID NO 98
<211> LENGTH: 208
<212> TYPE: PRT
<213> ORGANISM: Artificial Sequence
<220> FEATURE:
<223> OTHER INFORMATION: ATFHI-ML chimeric protein

<400> SEQUENCE: 98

```
Met Ser Asn Glu Leu His Gln Val Pro Ser Asn Cys Asp Cys Leu Asn
-1  1               5                   10                  15

Gly Gly Thr Cys Val Ser Asn Lys Tyr Phe Ser Asn Ile His Trp Cys
                20                  25                  30

Asn Cys Pro Lys Lys Phe Gly Gly Gln His Cys Glu Ile Asp Lys Ser
            35                  40                  45

Lys Thr Cys Tyr Glu Gly Asn Gly His Phe Tyr Arg Gly Lys Ala Ser
        50                  55                  60

Thr Asp Thr Met Gly Arg Pro Cys Leu Pro Trp Asn Ser Ala Thr Val
    65                  70                  75

Leu Gln Gln Thr Tyr His Ala His Arg Ser Asp Ala Leu Gln Leu Gly
80                  85                  90                  95

Leu Gly Lys His Asn Tyr Cys Arg Asn Pro Asp Asn Arg Arg Arg Pro
                100                 105                 110

Trp Cys Tyr Val Gln Val Gly Leu Lys Pro Leu Val Gln Glu Cys Met
            115                 120                 125

Val His Asp Cys Ala Asp Gly Lys Lys Pro Ser Ser Pro Pro Glu Glu
        130                 135                 140

Leu Lys Phe Gln Gly Thr Val Ala Ala Cys Asn Leu Pro Ile Val Arg
    145                 150                 155

Gly Pro Cys Arg Ala Phe Ile Gln Leu Trp Ala Phe Asp Ala Val Lys
160                 165                 170                 175

Gly Lys Cys Val Leu Phe Pro Tyr Gly Gly Cys Gln Gly Asn Gly Asn
                180                 185                 190

Lys Phe Tyr Ser Glu Lys Glu Cys Arg Glu Tyr Cys Gly Val Pro Gly
            195                 200                 205
```

<210> SEQ ID NO 99
<211> LENGTH: 9
<212> TYPE: PRT
<213> ORGANISM: Artificial Sequence
<220> FEATURE:
<223> OTHER INFORMATION: amino acids encoded by synthetic BamHI-TaqI DNA
      adaptor

<400> SEQUENCE: 99

```
Met Ser Asn Glu Leu His Gln Val Pro
1               5
```

<210> SEQ ID NO 100
<211> LENGTH: 3
<212> TYPE: PRT
<213> ORGANISM: Artificial Sequence
<220> FEATURE:
<223> OTHER INFORMATION: amino acids encoded by 5' portion of TaqI-KpnI
      ATF uPA DNA fragment

```
<400> SEQUENCE: 100

Asn Cys Asp
1

<210> SEQ ID NO 101
<211> LENGTH: 7
<212> TYPE: PRT
<213> ORGANISM: Artificial Sequence
<220> FEATURE:
<223> OTHER INFORMATION: amino acids encoded by 3' portion of TaqI-KpnI
      ATF uPA DNA fragment

<400> SEQUENCE: 101

Val His Asp Cys Ala Asp Gly
1               5

<210> SEQ ID NO 102
<211> LENGTH: 10
<212> TYPE: PRT
<213> ORGANISM: Artificial Sequence
<220> FEATURE:
<223> OTHER INFORMATION: amino acids encoded by 5' end of KpnI-BclI HI-8
      UTI DNA fragment

<400> SEQUENCE: 102

Thr Val Ala Ala Cys Asn Leu Pro Ile Val
1               5                   10

<210> SEQ ID NO 103
<211> LENGTH: 4
<212> TYPE: PRT
<213> ORGANISM: Artificial Sequence
<220> FEATURE:
<223> OTHER INFORMATION: amino acids encoded by 3' end of KpnI-BclI HI-8
      UTI DNA fragment

<400> SEQUENCE: 103

Gly Val Pro Gly
1

<210> SEQ ID NO 104
<211> LENGTH: 3
<212> TYPE: PRT
<213> ORGANISM: Artificial Sequence
<220> FEATURE:
<223> OTHER INFORMATION: amino acids encoded by 5' end of ATF uPA DNA
      fragment

<400> SEQUENCE: 104

Ala Asp Gly
1

<210> SEQ ID NO 105
<211> LENGTH: 4
<212> TYPE: PRT
<213> ORGANISM: Artificial Sequence
<220> FEATURE:
<223> OTHER INFORMATION: amino acids encoded by 3' end of ATF uPA DNA
      fragment

<400> SEQUENCE: 105

Thr Val Ala Ala
1

<210> SEQ ID NO 106
<211> LENGTH: 11
```

-continued

```
<212> TYPE: PRT
<213> ORGANISM: Artificial Sequence
<220> FEATURE:
<223> OTHER INFORMATION: amino acids encoded by HI-8 UTI DNA fragment
      with XbaI cleavage site

<400> SEQUENCE: 106

Lys Glu Cys Arg Glu Tyr Cys Gly Val Pro Gly
1               5                   10

<210> SEQ ID NO 107
<211> LENGTH: 14
<212> TYPE: PRT
<213> ORGANISM: Artificial Sequence
<220> FEATURE:
<223> OTHER INFORMATION: amino acids encoded by BsmI-XbaI HI-8 UTI
      adaptor

<400> SEQUENCE: 107

Glu Tyr Cys Gly Val Pro Gly Asp Gly Asp Glu Glu Leu Leu
1               5                   10
```